US012350034B2

(12) United States Patent  
Tiron et al.

(10) Patent No.: US 12,350,034 B2  
(45) Date of Patent: Jul. 8, 2025

(54) METHODS AND APPARATUS FOR DETECTION OF DISORDERED BREATHING

(71) Applicant: Resmed Sensor Technologies Limited, Sandyford (EC)

(72) Inventors: Roxana Tiron, Clonskeagh (IE); Graeme Lyon, Clonskeagh (IE); Redmond Shouldice, Clonskeagh (IE); Stephen McMahon, Dundrum (IE); Alberto Zaffaroni, Clonskeagh (IE); Stephen Dodd, Clonskeagh (IE)

(73) Assignee: Resmed Sensor Technologies Limited (IE)

( * ) Notice: Subject to any disclaimer, the term of this patent is extended or adjusted under 35 U.S.C. 154(b) by 803 days.

(21) Appl. No.: 17/293,253

(22) PCT Filed: Nov. 19, 2019

(86) PCT No.: PCT/EP2019/081818  
§ 371 (c)(1),  
(2) Date: May 12, 2021

(87) PCT Pub. No.: WO2020/104465  
PCT Pub. Date: May 28, 2020

(65) Prior Publication Data  
US 2022/0007965 A1    Jan. 13, 2022

Related U.S. Application Data

(60) Provisional application No. 62/784,491, filed on Dec. 23, 2018, provisional application No. 62/769,272, filed on Nov. 19, 2018.

(51) Int. Cl.  
*A61B 5/08* (2006.01)  
*A61B 5/00* (2006.01)  
(Continued)

(52) U.S. Cl.  
CPC .......... *A61B 5/0816* (2013.01); *A61B 5/0823* (2013.01); *A61B 5/113* (2013.01);  
(Continued)

(58) Field of Classification Search  
None  
See application file for complete search history.

(56) References Cited

U.S. PATENT DOCUMENTS 5,105,354 A * 4/1992 Nishimura ............. G16H 15/00  
600/511  
9,542,933 B2    1/2017 Mortensen  
(Continued)

FOREIGN PATENT DOCUMENTS

EP        1410759 A1    4/2004  
JP     2007517553 A    7/2007  
(Continued)

OTHER PUBLICATIONS

PCT International Search Report dated Jun. 25, 2020 for PCT/EP2019/081818.  
(Continued)

*Primary Examiner* — Aurelie H Tu  
(74) *Attorney, Agent, or Firm* — Botos Churchill IP Law LLP

(57) ABSTRACT

Methods and apparatus provide monitoring of a sleep disordered breathing state of a person such as for screening. One or more sensors may be configured for non-contact active and/or passive sensing. The processor(s) (7304, 7006) may extract respiratory effort signal(s) from one or more motion signals generated by active non-contact sensing with the sensor(s). The processor(s) may extract one or more energy band signals from an acoustic audio signal generated by passive non-contact sensing with the sensor(s). The processor(s) may assess the energy band signal(s) and/or the (Continued)

respiratory efforts signal(s) to generate intensity signal(s) representing sleep disorder breathing modulation. The processor(s) may classify feature(s) derived from the one or more intensity signals to generate measure(s) of sleep disordered breathing. The processor may generate a sleep disordered breathing indicator based on the measure(s) of sleep disordered breathing. Some versions may evaluate sensing signal(s) to generate indication(s) of cough event(s) and/or cough type.

25 Claims, 51 Drawing Sheets

(51) Int. Cl.
    *A61B 5/113*     (2006.01)
    *A61B 7/00*     (2006.01)
    *G16H 50/30*     (2018.01)

(52) U.S. Cl.
    CPC .......... *A61B 5/4812* (2013.01); *A61B 5/4815* (2013.01); *A61B 5/4818* (2013.01); *A61B 5/6898* (2013.01); *A61B 5/7221* (2013.01); *A61B 5/7225* (2013.01); *A61B 5/7228* (2013.01); *A61B 5/7257* (2013.01); *A61B 5/7264* (2013.01); *A61B 5/7275* (2013.01); *A61B 5/742* (2013.01); *A61B 7/003* (2013.01); *G16H 50/30* (2018.01); *A61B 2562/0204* (2013.01)

(56) References Cited

U.S. PATENT DOCUMENTS

| | | | |
|---|---|---|---|
| 2006/0212273 A1* | 9/2006 | Krausman | A61B 5/4818 702/189 |
| 2008/0004904 A1* | 1/2008 | Tran | G16H 40/67 340/286.07 |
| 2010/0018530 A1* | 1/2010 | Schindhelm | A61B 5/0873 128/204.23 |
| 2015/0250963 A1* | 9/2015 | Ramanan | A61M 16/0069 128/204.23 |
| 2016/0022204 A1 | 1/2016 | Mostov | |
| 2016/0361012 A1* | 12/2016 | Chen | A61B 5/7225 |

FOREIGN PATENT DOCUMENTS

| | | | |
|---|---|---|---|
| JP | 2012509155 A | 4/2012 | |
| JP | 2014008159 A | 1/2014 | |
| JP | 2015522314 A | 8/2015 | |
| WO | 2005067790 A1 | 7/2005 | |
| WO | 2010059839 A3 | 1/2012 | |
| WO | 2013177621 A1 | 12/2013 | |
| WO | 2018050913 A1 | 3/2018 | |
| WO | 2018122217 A1 | 7/2018 | |

OTHER PUBLICATIONS

JP Office Action issued Aug. 4, 2023 for Japanese Patent Application No. 2021-527983, 22 pages.
Second Office Action issued in corresponding Chinese Patent Application No. 2019800895775, mailed Aug. 31, 2024, 17 pages.

* cited by examiner

METHODS AND APPARATUS FOR DETECTION OF DISORDERED BREATHING

1 CROSS REFERENCE TO RELATED APPLICATIONS

The present application is a national phase entry under 35 U.S.C. § 371 of International Application No. PCT/EP2019/081818 filed Nov. 19, 2019, published in English, which claims priority from U.S. Provisional Patent Application Nos. 62/784,491 filed Dec. 23, 2018 and 62/769,272 filed Nov. 19, 2018, all of which are incorporated herein by reference.

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE TECHNOLOGY

5.1 Field of the Technology

The present technology relates to one or more of the detection, diagnosis, treatment, prevention and amelioration of disordered breathing such as sleep disordered breathing and/or coughing. The present technology also relates to medical devices or apparatus, and their use. In particular, the present technology relates to screening devices or apparatus, and their use, such as non-contact screening device.

5.2 Description of the Related Art

5.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition, published 2011.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production. COPD is the fourth leading cause of death worldwide, with greater than sixty-five million people being classified as moderate or severe, and impacts up to one quarter of all adults over forty years old (World Health Organization http://www.who.int/respiratory/copd/burden/en/).

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Heart failure (HF) is a relatively common and severe clinical condition, characterised by the inability of the heart to keep up with the oxygen demands of the body. Management of heart failure is a significant challenge to modern healthcare systems due to its high prevalence and severity. HF is a chronic condition, which is progressive in nature. The progression of HF is often characterized as relatively stable over long periods of time (albeit with reduced cardiovascular function) punctuated by episodes of an acute nature. In these acute episodes, the patient experiences worsening of symptoms such as dyspnea (difficulty breathing), gallop rhythms, increased jugular venous pressure, and orthopnea. This is typically accompanied by overt congestion (which is the buildup of fluid in the pulmonary cavity). This excess fluid often leads to measurable weight gain of several kilograms. In many cases, however, by the time overt congestion has occurred, there are limited options for the doctor to help restabilise the patients, and in many cases the patient requires hospitalization. In extreme cases, without timely treatment, the patient may undergo acute decompensated heart failure (ADHF) events, sometimes referred to as decompensations.

5.2.2 Therapy

Various therapies, such as Continuous Positive Airway Pressure (CPAP) therapy, Non-invasive ventilation (NIV), Invasive ventilation (IV) and High flow therapy (HFT) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

5.2.3 Treatment Systems

The above-mentioned therapies may be provided by a treatment system or device. Systems and devices may also be used to diagnose a condition without treating it.

A treatment system, such as a respiratory therapy device, may comprise a Respiratory Pressure Therapy Device (RPT device), an air circuit, a humidifier, a patient interface, and data management.

5.2.3.1 Patient Interface

A patient interface may be used to interface respiratory equipment to its user, for example by providing a flow of air. The flow of air may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 $cmH_2O$. For other forms of therapy, such as the delivery of oxygen, the patient interface may not include a seal sufficient to facilitate delivery to the airways of a supply of gas at a positive pressure of about 10 $cmH_2O$.

5.2.3.2 RPT Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, including one or more of comfort, noise, ease of use, efficacy, size, weight, manufacturability, cost, and reliability.

5.2.3.3 Humidifier

Delivery of a flow of air without humidification may cause drying of airways. The use of a humidifier with a RPT device and the patient interface produces humidified gas that minimizes drying of the nasal mucosa and increases patient airway comfort. In addition in cooler climates, warm air applied generally to the face area in and about the patient interface is more comfortable than cold air.

5.2.4 Diagnosis and Monitoring Systems

Diagnosis is the identification of a condition from its signs and symptoms. Diagnosis tends to be a one-off process, whereas monitoring the progress of a condition can continue indefinitely. Some diagnosis systems are suitable only for diagnosis, whereas some may also be used for monitoring. Screening typically involves a diagnostic process such as with monitoring of signs and systems over time that may be evaluated in relation to a particular condition for diagnosis.

It is of interest to be able to detect SDB and other sleeping disorders. Sleep-Disordered Breathing may be considered to be abnormal respiration during sleep, such as the cessation of breathing or "sleep suffocation". Most prevalent is obstructive sleep apnea—collapse of the upper airway despite ongoing effort. Other types include central sleep apnea with lack of breathing and lack of effort, and mixed apnea. As a condition related to sleep, screening for a diagnosis or even monitoring can be a difficult task. Sleep Apnea is more than 80% undiagnosed (Peppard P E et al. Am J Epidemiol 2013; Young T et al. Sleep 1997). For example, for every four people who have sleep apnoea, there are another twenty-two people that do not know they have the condition. Therefore, simple, easy to access means for screening for sleep disordered breathing or sleep apnea to detect the condition may have a significant societal benefit.

Polysomnography (PSG) is a conventional system for monitoring of patients. PSG typically involves the placement of 15 to 20 contact sensors on a person in order to record various bodily signals such as electroencephalography (EEG), electrocardiography (ECG), electrooculograpy (EOG), etc. Such numerous contact sensors and leads are prone to failure, can be costly, and have limited accessibly, such that it makes PSG an undesirable method for detection of sleep related conditions.

S+(pronounced ess-plus) (ResMed Sensor Technologies Ltd, Dublin, Ireland) is a contactless bedside monitor suitable for long-term monitoring of chronic diseases such as HF and COPD. S+ contains a biomotion transceiver sensor operating on radar principles in a licence-free band at 5.8 GHz or 10.5 GHz at ultra-low power (less than 1 mW). S+ is capable of measuring bodily movement over a distance ranging from 0.3 to 1.5 metres; in the case of two people in a bed, a combination of sophisticated sensor design and intelligent signal processing allows S+ to measure only the movement of the person nearest to the sensor. The S+ is suitable for long-term monitoring of SDB as it is unobtrusive and does not present significant compliance issues. However, processing the raw S+ signals to obtain information useful for SDB screening, monitoring or diagnosis is a difficult and complex task.

6 BRIEF SUMMARY OF THE TECHNOLOGY

The present technology is directed towards providing medical devices used in the diagnosis, monitoring, amelioration, treatment, or prevention of respiratory disordered breathing such as sleep disordered breathing and/or coughing having one or more of improved comfort, cost, efficacy, ease of use and manufacturability.

An aspect of the present technology relates to apparatus used in the screening, diagnosis or monitoring of sleep-disordered breathing (including, for example, different types of apneas, hypopneas, flow limitation, snore) and/or coughing.

Another aspect of the present technology relates to methods used in the screening, diagnosis or monitoring of sleep-disordered breathing and/or coughing using non-contact sensors.

Some versions of the present technology may include a method of one or more processors for monitoring a sleep disordered breathing state of a person. The method in the one or more processors may include extracting one or more respiratory signals from one or more motion signals, the one or more motion signals generated by active non-contact sensing. The method in the one or more processors may include extracting one or more energy band signals from a passive signal, the passive signal generated by passive non-contact sensing. The passive signal may represent acoustic information detected by a sound sensor. The method in the one or more processors may include assessing the one or more energy band signals and/or the one or more respiratory signals to generate one or more intensity signals representing intensity of sleep disorder breathing modulation. The method in the one or more processors may include classifying one or more features derived from the one or more intensity signals to generate one or more measures of sleep disordered breathing. Any one of the classification of features and the generation of measures of sleep disorder breathing, can be generated or processed remotely—by one or more remote processing device(s) or server(s). Thus, in some embodiments, the method may include transmitting to remote device/s or server/s either data for classification or classified features for generation of measure/s of sleep disorder breathing.

In some versions, the method in the one or more processors may include generating a sleep disordered breathing indicator based on the one or more measures of sleep disordered breathing. The method in the one or more processors may include displaying or controlling of displaying, on a display, and/or forwarding the sleep disordered breathing indicator. The method in the one or more processors may include displaying or controlling of displaying, on a display, and/or forwarding the one or more measures of sleep disordered breathing. The one or more respiratory signals may include a respiratory effort signal. The one or more measures of sleep disordered breathing may include a probability of sleep disordered breathing. The classifying may include identifying one of an affirmation and a negation of a presence of a number of sleep disordered breathing events exceeding a threshold for a sleep session, and wherein the one or more measures of sleep disordered breathing may include a binary flag representing a result of the identifying. The binary flag may represent the affirmation when the probability exceeds a threshold. The sleep disordered breathing events may include at least one of apnea and hypopnea events. The one or more measures of sleep disordered breathing may include an apnea-hypopnea index representing an estimate of a total number of apnea events and hypopnea events.

In some versions, the method of the one or more processors may include generating a sleep stage adjustment factor based on the probability. The method of the one or more processors may include adjusting a sleep stage time as a function of the sleep stage adjustment factor. The method of the one or more processors may include generating a cluster flag signal based one or more intensity signals. The cluster flag signal may represent a time series identifying presence and absence of SDB modulation. The cluster flag signal may be generated based on comparisons between values of the one or more intensity signals and a threshold. A flag of the cluster flag signal may be set to true when a value the one or more intensity signals is greater than a first intensity threshold. The cluster flag signal may be further set according to an evaluation of values of a filtered signal when compared to a second intensity threshold. The filtered signal may be derived by filtering the one or more intensity signals. The one or more features may include one or more proportions of total sleep time having SDB clusters. The one or more features may include a peak intensity or peak mean intensity.

In some versions, the method of the one or more processors may include generating a sleep-wake correction mask signal based on a generated cluster flag signal that characterizes a presence of detected SDB clusters. The method of the one or more processors may include applying the sleep-wake correction mask signal to a sleep staging process wherein instances of wake classification may be corrected to instances of sleep according to the sleep-wake correction mask signal. The generated sleep disordered breathing indicator may include a graphic risk-o-meter displayed on a display device, the graphic risk-o-meter comprising a pointer and scale. The scale may be presented with indications of discrete ranges of sleep disordered breathing risk. The assessing the one or more respiratory signals to generate one or more intensity signals representing intensity of sleep disorder breathing modulation may include any one, more or all of: (a) generating an envelope signal; (b) normalizing the envelope signal; and (c) generating spectral characteristics from the normalized envelope signal. The spectral characteristics may include peak frequencies of power spectral density operations in a sleep disordered breathing frequency range. The spectral characteristics may include an in-band metric that may include a ratio of: (a) a peak frequency of a power spectral density operation or power in a narrow band around the peak frequency, and (b) power in the sleep disordered breathing frequency range from the power spectral density operation. The spectral characteristics may include an in-band metric that may include a ratio of: (a) power in a narrow band around a peak frequency of a power spectral density operation, and (b) a difference between a total power of the spectrum of the power spectral density operation and the power in the narrow band around the peak frequency. The in-band metric may be an average metric derived from in-band metric values from an I channel motion signal and a Q channel motion signal.

In some versions, the assessing the one or more energy band signals to generate one or more intensity signals representing intensity of sleep disorder breathing modulation may include any one, more or all of: (a) combining the one or more energy band signals; (b) generating an envelope signal from the combined energy band signals; (c) filtering and normalizing the envelope signal from the combined energy band signals; and (d) generating spectral characteristics from the filtered and normalized envelope signal. The spectral characteristics from the filtered and normalized envelope signal may include an in-band metric comprising a ratio of: (a) a peak frequency of a power spectral density operation, and (b) power in a sleep disordered breathing frequency range from the power spectral density operation. The spectral characteristics from the filtered and normalized envelope signal may include an in-band metric comprising a ratio of: (a) power in a narrow band around a peak frequency of a power spectral density operation, and (b) a difference between a total power of the spectrum of the power spectral density operation and the power in the narrow band around the peak frequency.

In some versions, the extracting one or more respiratory signals from one or more motion signals may include combining a plurality of motion signals. Each of the motion signals of the plurality of motion signals may be a motion signal representing motion from a detection range that may be different from a detection range from other motion signals of the plurality of motion signals. The combining may include computing weights according to respiratory frequencies from a power spectral density for each of the plurality of motion signals and determining a weighted average of absolute values of the plurality of motion signals. The extracting of one or more energy band signals from a passive signal may include any one, more or all of: (a) separating sound frequencies of the passive signal into band signals by computing transformations of the passive signal; (b) computing energy values of the band signals; and (c) averaging computed energy values for each band signal.

In some versions, the active non-contact sensing may include SONAR sensing with a microphone and speaker. The active non-contact sensing may include RADAR sensing with a radio frequency transmitter and receiver. The active non-contact sensing may include frequency modulated continuous wave (FMCW) sensing. The passive non-contact sensing may include acoustic sensing of breathing related sounds with a microphone. The method of the one or more processors may include pre-processing a sound signal generated by the microphone to produce the passive signal. The pre-processing may include any one, more or all of: (a) filtering with an infinite impulse response filter; (b) baseline removal comprising subtraction of a minimum over a sliding window; (c) artefact removal employing a percentile limit; (d) normalization with a standard deviation over a sliding window; and (e) integration and high-pass filtering. The method of the one or more processors may include autocorrelating the pre-processed sound signal. The method of the one or more processors may include detecting a peak with a pre-defined respiration range of the autocorrelated, pre-processed sound signal. The method of the one or more processors may include determining a respiration rate estimate from peaks of a plurality of signals. Each of the signals of the plurality of signals may be a sound signal of a discrete frequency band and processed by the pre-processing and the autocorrelating. The one or more features may be a plurality of features derived from a plurality of intensity signals from the one or more energy band signals and the one or more respiratory signals, and the generated one or more measures of sleep disordered breathing may be generated by classification of the plurality of features.

In some versions, the one or more processors may be in a processing device, the processing device may include any of a smart phone, a tablet computer, a general computing device, a smart speaker, a smart TV, a smart watch and a respiratory therapy device. The method of the one or more processors may include controlling, with the one or more processors, a change to a setting of a therapy of a respiratory therapy device based on the one or more measures of sleep disordered breathing.

In some versions, where at least some of the processing is performed on one or more remote device(s), the method may further include, in the one or more processors, receiving back from the remote device(s) the generated one or more measures of sleep disordered breathing. The method may further include (a) displaying the received one or more measures of sleep disordered breathing on a display, or (b) transmitting, via data communications transmission, the received one or more measures of sleep disordered breathing to a local processing/displaying device.

Some versions of the present technology may include a processor-readable medium, having stored thereon processor-executable instructions which, when executed by one or more processors, cause the one or more processors to monitor a sleep disordered breathing state of a person, the processor-executable instructions may be configured to execute the method of any one of methods described herein.

Some versions of the present technology may include a server with access to the processor-readable medium of claim, wherein the server may be configured to receive requests for downloading the processor-executable instructions of the processor-readable medium to a processing device over a network.

Some versions of the present technology may include a processing device comprising: one or more processors; a speaker coupled to the one or more processors; a microphone coupled to the one or more processors; and a processor-readable medium as described herein. The processing device may include any of a smart phone, a tablet computer, a general computing device, a smart speaker, a smart TV, a smart watch and a respiratory therapy device.

Some versions of the present technology may include a processing device including one or more processors; a microphone coupled to the one or more processors; a radio frequency sensor coupled to the one or more processors; and a processor-readable medium of as described herein.

Some versions of the present technology may include a method of a server having access to the processor-readable medium as described herein. The method may include receiving, at the server, a request for downloading the processor-executable instructions of the processor-readable medium to a processing device over a network. The method may include transmitting the processor-executable instructions to the processing device in response to the request.

Some versions of the present technology may include apparatus for monitoring a sleep disordered breathing state of a person. The apparatus may include one or more processors. The one or more processors may be configured to extract one or more respiratory signals from one or more motion signals, the one or more motion signals generated by active non-contact sensing with one or more sensors. The one or more processors may be configured to extract one or more energy band signals from a passive signal, the passive signal generated by passive non-contact sensing with the one or more sensors. The passive signal may represent acoustic information detected by a sound sensor of the one or more sensors. The one or more processors may be configured to assess the one or more energy band signals and/or the one or more respiratory signals to generate one or more intensity signals representing intensity of sleep disorder breathing modulation. The one or more processors may be configured to classify, or transmit for classification, one or more features derived from the one or more intensity signals to generate one or more measures of sleep disordered breathing. The one or more processors may be further configured to generate a sleep disordered breathing indicator based on the one or more measures of sleep disordered breathing.

In some versions, the apparatus may include the one or more sensors configured for active non-contact sensing and passive non-contact sensing. Alternatively, the apparatus may be arranged to communicate with, and utilise data from, external sensors already positioned in the surroundings of the apparatus (such as smart speakers etc.) The one or more processors, may be communicatively coupled with one or more sensors. The one or more sensors may be configured for active non-contact sensing and passive non-contact sensing. The one or more processors may be further configured to display, on a display, and/or to forward the sleep disordered breathing indicator. The one or more processors may be further configured to display, on a display, and/or to forward the one or more measures of sleep disordered breathing. The one or more respiratory signal may include a respiratory effort signal. The one or more measures of sleep disordered breathing may include a probability of sleep disordered breathing. The classifying may include identifying one of an affirmation and a negation of a presence of a number of sleep disordered breathing events exceeding a threshold for a sleep session. The one or more measures of sleep disordered breathing may include a binary flag representing a result of the identifying. The binary flag may represent the affirmation when the probability exceeds a threshold. The sleep disordered breathing events may include at least one of apnea and hypopnea events. The one or more measures of sleep disordered breathing may include an apnea-hypopnea index representing an estimate of a total number of apnea events and hypopnea events. The one or more processors may be further configured to generate a sleep stage adjustment factor based on the probability. The one or more processors may be further configured to adjust a sleep stage time as a function of the adjustment factor. The one or more processors may be further configured to generate a cluster flag signal based one or more intensity signals. The cluster flag signal may represent a time series identifying presence and absence of SDB modulation. The cluster flag signal may be generated based comparisons between values of the one or more intensity signals and a threshold. A flag of the cluster flag signal may be set to true when a value the one or more intensity signals is greater than a first intensity threshold. The cluster flag signal may be further set according to an evaluation of values of a filtered signal in comparison with a second intensity threshold. The filtered signal may be derived by filtering the one or more intensity signals. The one or more features may include one or more proportions of total sleep time having SDB clusters. The one or more features may include a peak intensity or peak mean intensity.

In some versions, the one or more processors may be further configured to generate a sleep-wake correction mask signal based on a generated cluster flag signal that characterizes a presence of detected SDB clusters. The one or more processors may be further configured to apply the sleep-wake correction mask signal to a sleep staging process wherein instances of wake classification are corrected to instances of sleep according to the sleep-wake correction mask signal. The generated sleep disordered breathing indicator may include a graphic risk-o-meter displayed on a display device. The graphic risk-o-meter may include a pointer and scale. The scale may be presented with indications of discrete ranges of sleep disordered breathing risk. To assess the one or more respiratory signals to generate one or more intensity signals representing intensity of sleep disorder breathing modulation, the one or more processors are configured to, or control any one, more or all of: (a) generate an envelope signal; (b) normalize the envelope signal; and (c) generate spectral characteristics from the normalized envelope signal. The spectral characteristics may include peak frequencies of power spectral density operations in a sleep disordered breathing frequency range. The spectral characteristics may include an in-band metric that may include a ratio of: (a) a peak frequency of a power spectral density operation, and (b) power in the sleep disordered breathing frequency range from the power spectral density operation. The spectral characteristics may include an in-band metric that may include a ratio of: (a) power in a narrow band around a peak frequency of a power spectral density operation, and (b) a difference between a total power of the spectrum of the power spectral density operation and the power in the narrow band around the peak frequency. The in-band metric may be an average metric derived from in-band metric values from an I channel motion signal and a Q channel motion signal.

In some versions, to assess the one or more energy band signals to generate one or more intensity signals representing intensity of sleep disorder breathing modulation, the one or more processors may be configured to, control or perform any one, more of all of: (a) combine the one or more energy band signals; (b)
    generate an envelope signal from the combined energy band signals; (c) filter and normalize the envelope signal from the combined energy band signals; and (d) generate spectral characteristics from the filtered and normalized envelope signal. The spectral characteristics from the filtered and normalized envelope signal may include an in-band metric comprising a ratio of: (a) a peak frequency of a power spectral density operation, and (b) power in a sleep disordered breathing frequency range from the power spectral density operation. The spectral characteristics from the filtered and normalized envelope signal may include an in-band metric comprising a ratio of: (a) power in a narrow band around a peak frequency of a power spectral density operation, and (b) a difference between a total power of the spectrum of the power spectral density operation and the power in the narrow band around the peak frequency.

In some versions, to extract one or more respiratory effort signals from one or more motion signals, the one or more processors may be configured to combine a plurality of motion signals, each of the motion signals of the plurality of motion signals being a motion signal representing motion from a detection range that may be different from a detection range from other motion signals of the plurality of motion signals. To combine the plurality of motion signals, the one or more processors may be configured to compute weights according to respiratory frequencies from a power spectral density for each of the plurality of motion signals and to determine a weighted average of absolute values of the plurality of motion signals. To extract the one or more energy band signals from a passive signal, the one or more processors are configured to control or perform any one, more or all of: (a) separate sound frequencies of the passive signal into band signals by computing transformations of the passive signal; (b) compute energy values of the band signals; and (c) average computed energy values for each band signal.

In some versions of the apparatus, the active non-contact sensing may include SONAR sensing wherein the one or more sensors may include a microphone and speaker. The active non-contact sensing may include RADAR sensing wherein the one or more sensors may include a radio frequency transmitter and receiver. The active non-contact sensing may include frequency modulated continuous wave (FMCW) sensing. The passive non-contact sensing may include acoustic sensing of breathing related sounds wherein the one or more sensors may include a microphone. The one or more processors may be configured to pre-process a sound signal generated by the microphone to produce the passive signal. The pre-processing may include any one, more or all of: filtering with an infinite impulse response filter; baseline removal comprising subtraction of a minimum over a sliding window; artefact removal employing a percentile limit; normalization with a standard deviation over a sliding window; and integration and high-pass filtering. The one or more processors may be configured to autocorrelate the pre-processed sound signal. The one or more processors may be configured to detect a peak with a pre-defined respiration range of the autocorrelated, pre-processed sound signal. The one or more processors may be configured to determine a respiration rate estimate from peaks of a plurality of signals, each of the plurality of signals being a sound signal of a discrete frequency band and processed by the pre-processing and the autocorrelating. The one or more features may be a plurality of features derived from a plurality of intensity signals from the one or more energy band signals and the one or more respiratory efforts signals, and the generated one or more measures of sleep disordered breathing may be generated by classification of the plurality of features. The one or more processors may be in a processing device, the processing device comprising any of a general computing device, a smart phone, a tablet computer, a smart speaker, a smart TV, a smart watch and a respiratory therapy device. The one or more processors may be configured to control a change to a setting of a therapy of a respiratory therapy device based on the one or more measures of sleep disordered breathing. The apparatus may include a processor-readable medium as described herein.

In some versions of the apparatus, the one or more processors may be further configured to receive the generated one or more measures of sleep disordered breathing, which have been derived by way of processing by one or more external device(s). The one or more processors may be further configured to (a) display the received one or more measures of sleep disordered breathing on a display; or (b) transmit, via data communications transmission, the received one or more measures of sleep disordered breathing to a local processing/displaying device.

Some versions of the present technology may include a method of one or more processors for identifying coughing by a person. The method in the one or more processors may include accessing an acoustic signal generated with a microphone. The acoustic signal generated by passive non-contact sensing in a vicinity of a person. The method in the one or more processors may include deriving one or more cough related features from the acoustic signal. The method in the one or more processors may include classifying, or transmitting for classification, the one or more cough related features to generate an indication of one or more events of coughing by the person.

In some versions, the one or more cough related features concern an absence or presence of coughing of the person. The classifying the one or more features may include identifying a cough type. The coughing type may include any one or more of (a) dry coughing type, (b) productive coughing type, (c) wheezing related coughing type, and (d) spasm related coughing type. Classifying the one or more features may include identifying a cough attribution type. The cough attribution type may include any one or more of (a) asthmatic coughing type, (b) Chronic obstructive pulmonary (COPD) coughing type, (c) bronchitis coughing type, (d) tuberculosis (TB) coughing type, (e) pneumonia coughing type, (f) lung cancer coughing type, (g) gastroesophageal reflux disease (GERD), and (h) upper airway cough syndrome. The one or more processors may be further configured to generate a coughing intensity metric indicative of a level of intensity of an event of the one or more events of coughing. The coughing intensity metric may include an acoustic amplitude value and/or a loudness value. The one or more processors may be further configured to determine variability of the coughing intensity metric. The one or more features derived from the acoustic signal may include any one, more or all of: a frequency feature, a temporal feature, a spectrogram feature and a wavelet feature.

In some versions, a frequency related feature of the one or more features derived from the acoustic signal may include any one, more or all of: (1) a local peak, (2) a ratio of a dominant peak to one or more surrounding peaks, (3) a local maxima, (4) a global maxima; (5) harmonics, (6) an integration of one or more frequency components, (8) a ratio of different frequency energy estimates, (7) one or more Mel-frequency cepstral coefficients (MFCCs), (9) spectral flux, (10) a spectral centroid, (11) a harmonic product spectrum, (12) a spectral spread, (13) one or more spectral autocorrelation coefficients, (14) a spectral kurtosis, and (15) a linear Predictive Coding (LPC). A temporal related feature of the one or more features derived from the acoustic signal may include any one, more or all of: (1) a root mean square (RMS) value, (2) a zero-crossing rate, (3) an envelope; and (4) a pitch based on an auto correlation function. The method may include processing the acoustic signal by voice activation detection to reject background noise in the acoustic signal. The method may further include estimating a cough rate from the acoustic signal. The method may further include estimating a variation of cough rate. The one or more processors may be configured to extract respiratory features from a detected breathing waveform. The classifying of the one or more features to generate an indication of one or more events of coughing by the person, may be based on one or more respiratory features extracted from the detected breathing waveform. The one or more respiratory features may include one, more or all of: (1) inspiration time, (2) inspiration depth, (3) expiration time, (4) expiration depth, (5) an inspiration-to-expiration ratio, (6) one or more notches in the breathing waveform due to cough, and (7) breathing rate. The one or more respiratory features may be derived with one or more of passive non-contact sensing and active non-contact sensing. The one or more processors may be configured to generate one or more motion signals by active non-contact sensing with active non-contact sensing apparatus. The one or more processors may be configured generates the indication of one or more events of coughing by the person based on an evaluation of the generated one or more motion signals.

In some versions, the method may include detection of body position of the person. The evaluation of the generated one or more motion signals may include detection of biometrics particular to the person. The evaluation of the generated one or more motion signals may include a detection of sleep stage information from the one or more motion signals. The one or more processors may be configured to reject an acoustically sensed cough event based on the detection of sleep stage information. The one or more processors may be configured to attribute an acoustically sensed cough event to the person based on the detection of sleep stage information. The active non-contact sensing may include one or more of an acoustic-type sensing, an optical-type sensing, and a RADAR-type sensing. The one or more processors may be configured to communicate data concerning the indication of the one or more events of coughing by the person to recommend further investigation of the condition and/or to control one or more of; an environmental parameter, a setting on a treatment device, a behavioural change and/or a treatment parameter. The one or more processors may be further configured to generate a reminder to change or wash bedclothes.

In some versions, the classifying involves a classifier derived by any one or more of supervised machine learning, deep learning, a convolutional neural network, and a recurrent neural network. The method may further include monitoring sound to detect user environmental interaction. The user environmental interaction may include detection of user environmental interaction signatures may include any one of more of a clicker, an appliance and a door. The monitoring sound to detect user environmental interaction may include assessing a pattern of activity of a monitored person to generate an indication of a need for contact with the monitored person.

The methods, systems, devices and apparatus described herein can provide improved functioning in a processor, such as of a processor of a processing device such as a specific purpose computer, and/or a sleep and/or sleep-disordered breathing diagnosis/monitoring apparatus. Moreover, in some cases they may communicate with or be integrated within a controller or processor of a treatment device such as a respiratory therapy device. Moreover, the described methods, systems, devices and apparatus can provide improvements in the technological field of automated management, screening, monitoring and/or treatment of sleep related conditions and/or respiratory conditions, including, for example, sleep disordered breathing.

Some versions of the present technology may include a processor-readable medium, having stored thereon processor-executable instructions which, when executed by one or more processors, cause the one or more processors to identify coughing by a person, according to any of the methods described herein. Some versions of the present technology may include server with access such a processor-readable medium and receive requests for downloading the processor-executable instructions of the processor-readable medium to a processing device over a network. Such a processing device may include: one or more processors; a speaker coupled to the one or more processors; a microphone coupled to the one or more processors; and a processor-readable medium as described herein or the one or more processors may be configured to access the processor-executable instructions with the server. The processing device may include any of a smart phone, a tablet computer, a general computing device, a smart speaker, a smart TV, a smart watch and a respiratory therapy device. The processing device may include one or more processors; a microphone coupled to the one or more processors; a radio frequency sensor coupled to the one or more processors; and such a processor-readable medium.

Some versions of the present technology may include a method of a server having access to such a processor-readable medium. The method may include receiving, at the server, a request for downloading the processor-executable instructions of the processor-readable medium to a processing device over a network; and transmitting the processor-executable instructions to the processing device in response to the request.

Some versions of the present technology may include a processing device for identifying coughing by a person. The device may include one or more microphones configured for passive non-contact sensing, wherein the one or more microphones generates an acoustic signal by passive non-contact sensing in a vicinity of a person. The device may include one or more processors coupled to the one or more microphones. The one or more processors may include a module configured to access the acoustic signal generated with the one or more microphones. The one or more processors may include a module configured to derive one or more features from the acoustic signal. The one or more features may concern an absence or presence of coughing of the person. The one or more processors may include a module configured to classify, or transmit for classification, the one or more features to generate an indication of one or more events of coughing by the person. The processing device may include any of a smart phone, a tablet computer, a general computing device, a smart speaker, a smart TV, a smart watch and a respiratory therapy device. The processors may be further arranged to display the generated event indicator(s) on a display of the device, or to forward the generated event indicator(s) to an external processing/displaying device.

The methods, systems, devices and apparatus described herein can provide improved functioning in a processor, such as of a processor of a processing device such as a specific purpose computer, and/or a sleep and/or sleep-disordered breathing diagnosis/monitoring apparatus. Moreover, in some cases they may communicate with or be integrated within a controller or processor of a treatment device such as a respiratory therapy device. Moreover, the described methods, systems, devices and apparatus can provide improvements in the technological field of automated management, screening, monitoring and/or treatment of sleep related conditions and/or respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7 BRIEF DESCRIPTION OF THE DRAWINGS

The present technology is illustrated by way of example, and not by way of limitation, in the figures of the accompanying drawings, in which like reference numerals refer to similar elements including:

7.1 Treatment Systems

FIG. 1 shows an example treatment system in accordance with one form of the present technology. A patient 1000 wearing a patient interface 3000 receives a supply of air at positive pressure from an RPT device 4000. Air from the RPT device 4000 is humidified in a humidifier 5000, and passes along an air circuit 4170 to the patient 1000.

7.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

7.3 Patient Interface

FIG. 3 shows a patient interface in the form of a nasal mask in accordance with one form of the present technology.

7.4 RPT Device

7.5 Humidifier

Figure 5A:
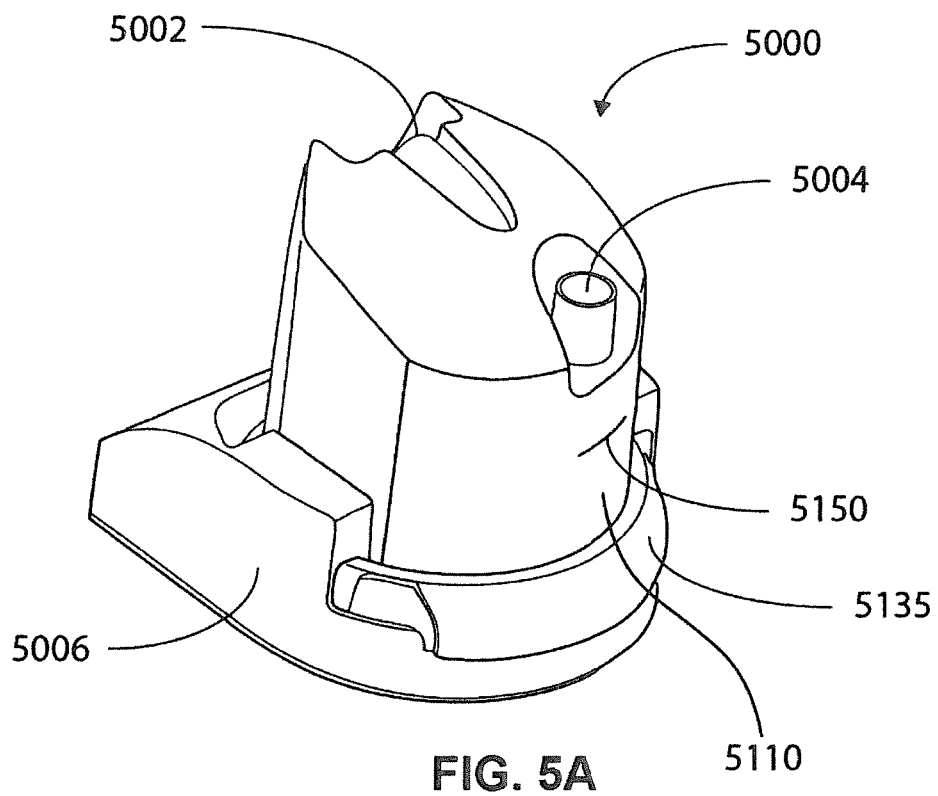
Figure 5B:
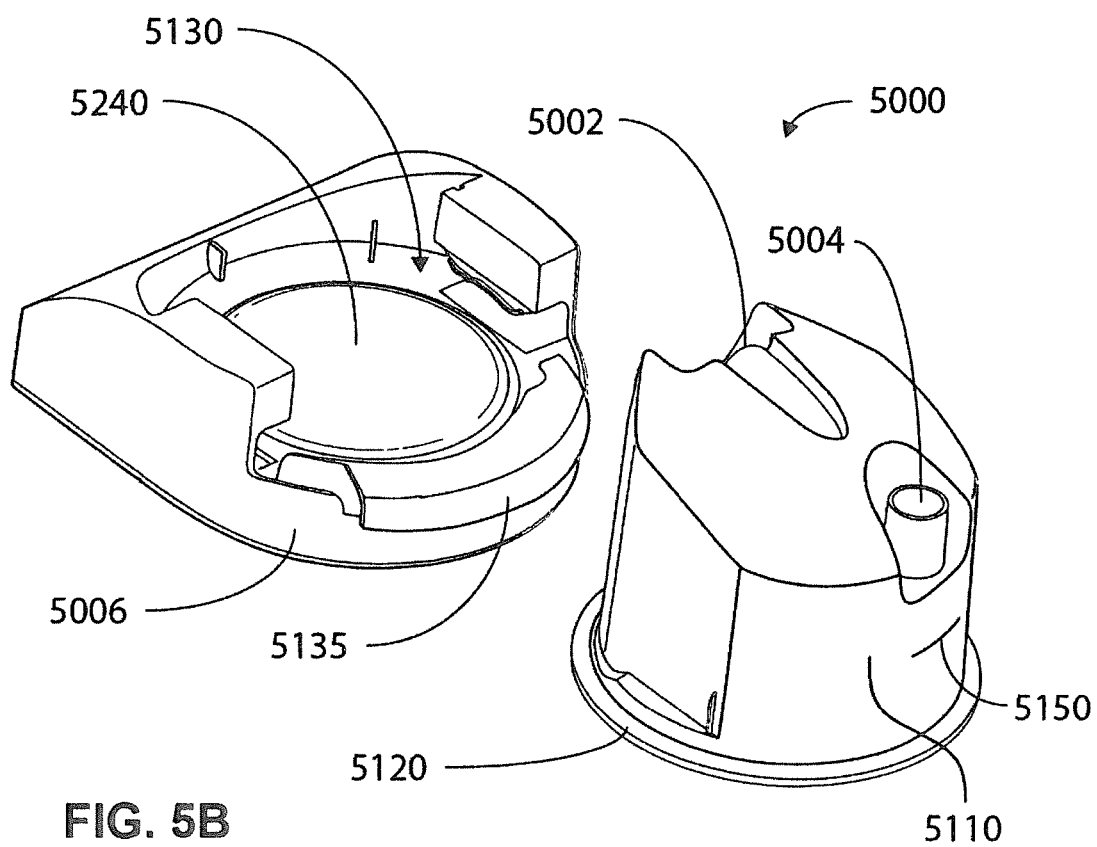

FIGS. 5A and 5B show isometric views of a humidifier in accordance with one aspect of the present technology.

7.6 Breathing Waveforms

Figure 6A:
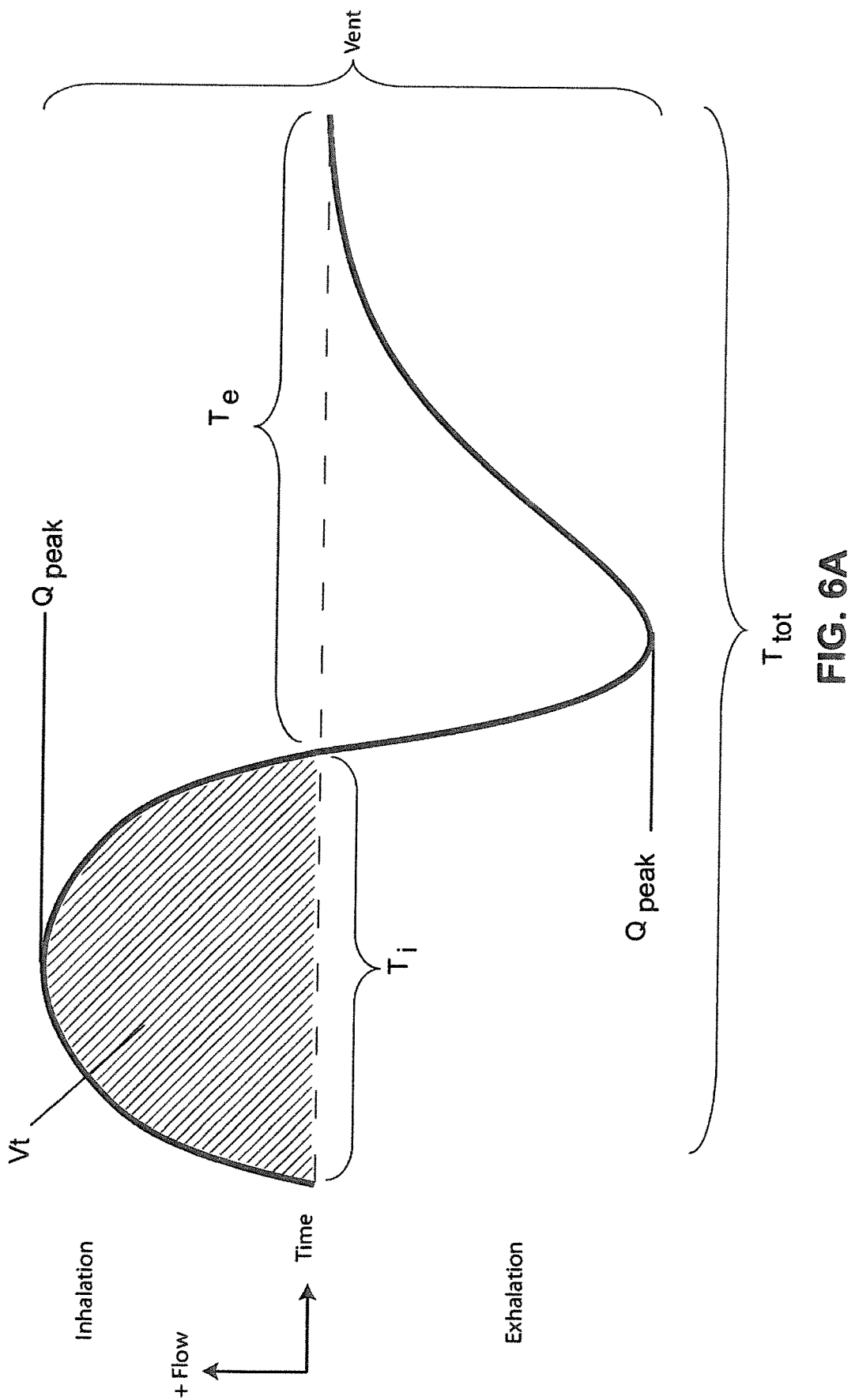

FIG. 6A shows a model typical breath waveform of a person while sleeping.

Figure 6B:
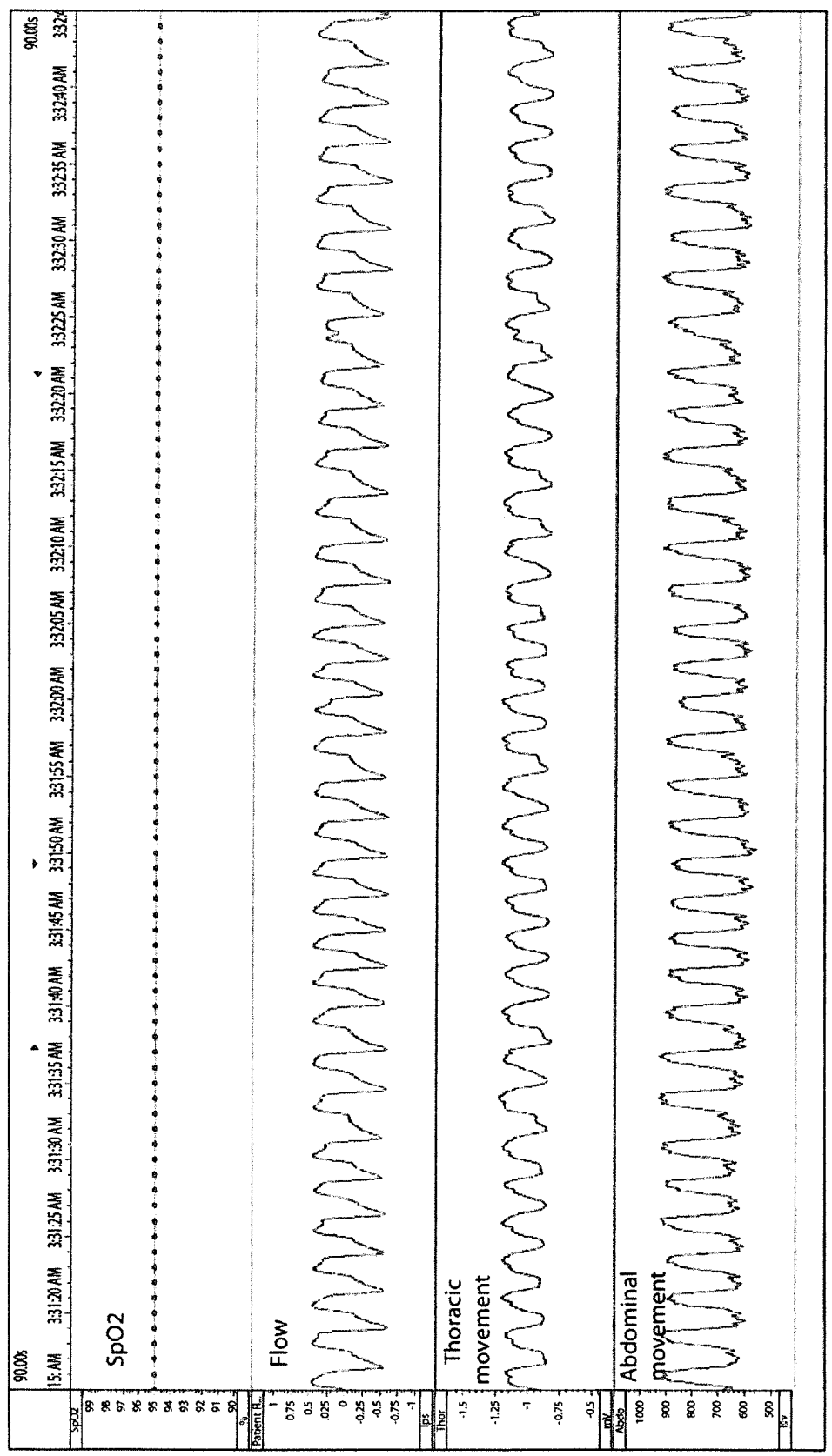

FIG. 6B shows polysomnography data of a patient during non-REM sleep breathing normally over a period of about ninety seconds.

Figure 6C:
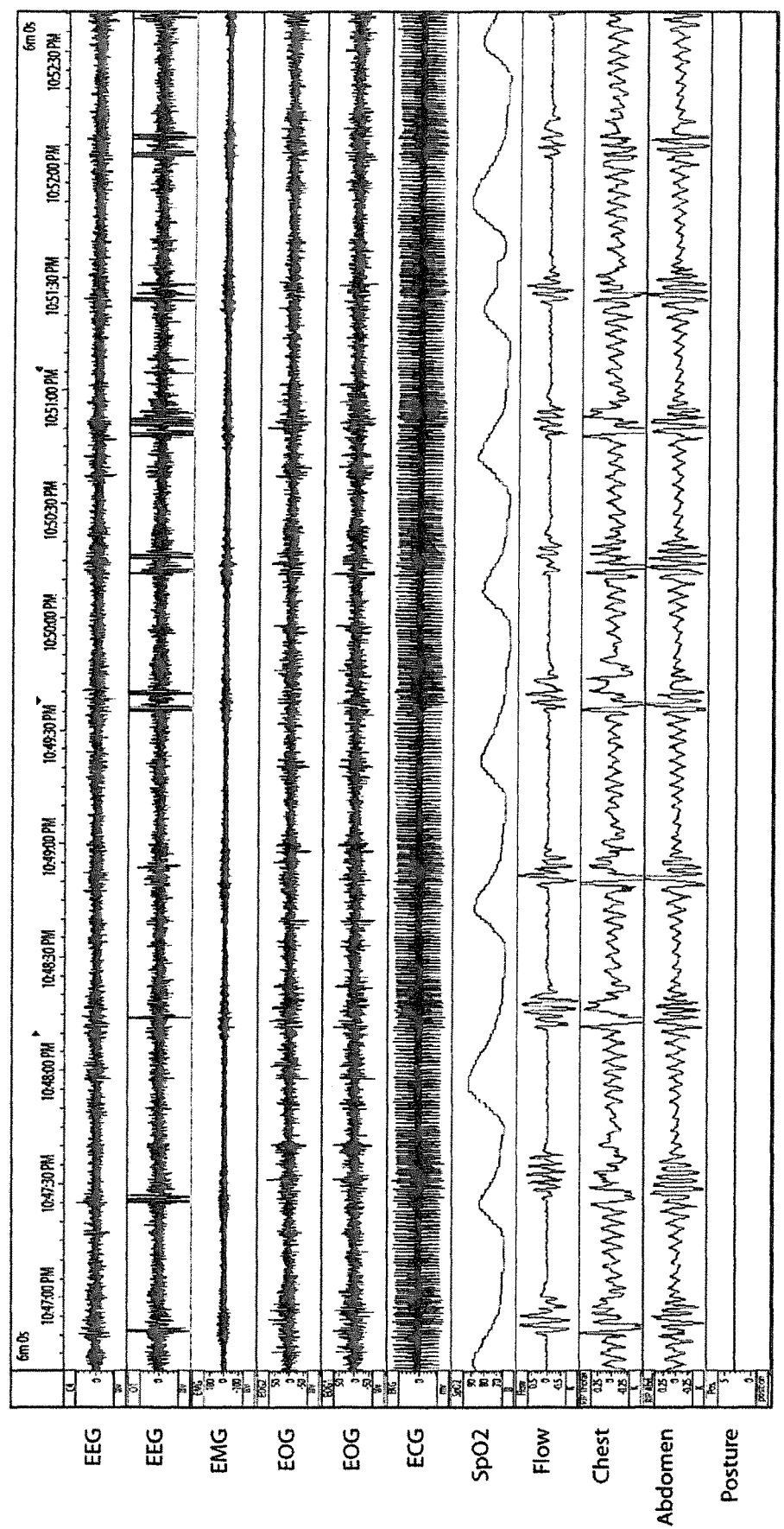

FIG. 6C shows polysomnography data of a patient with OSA.

Figure 6D:
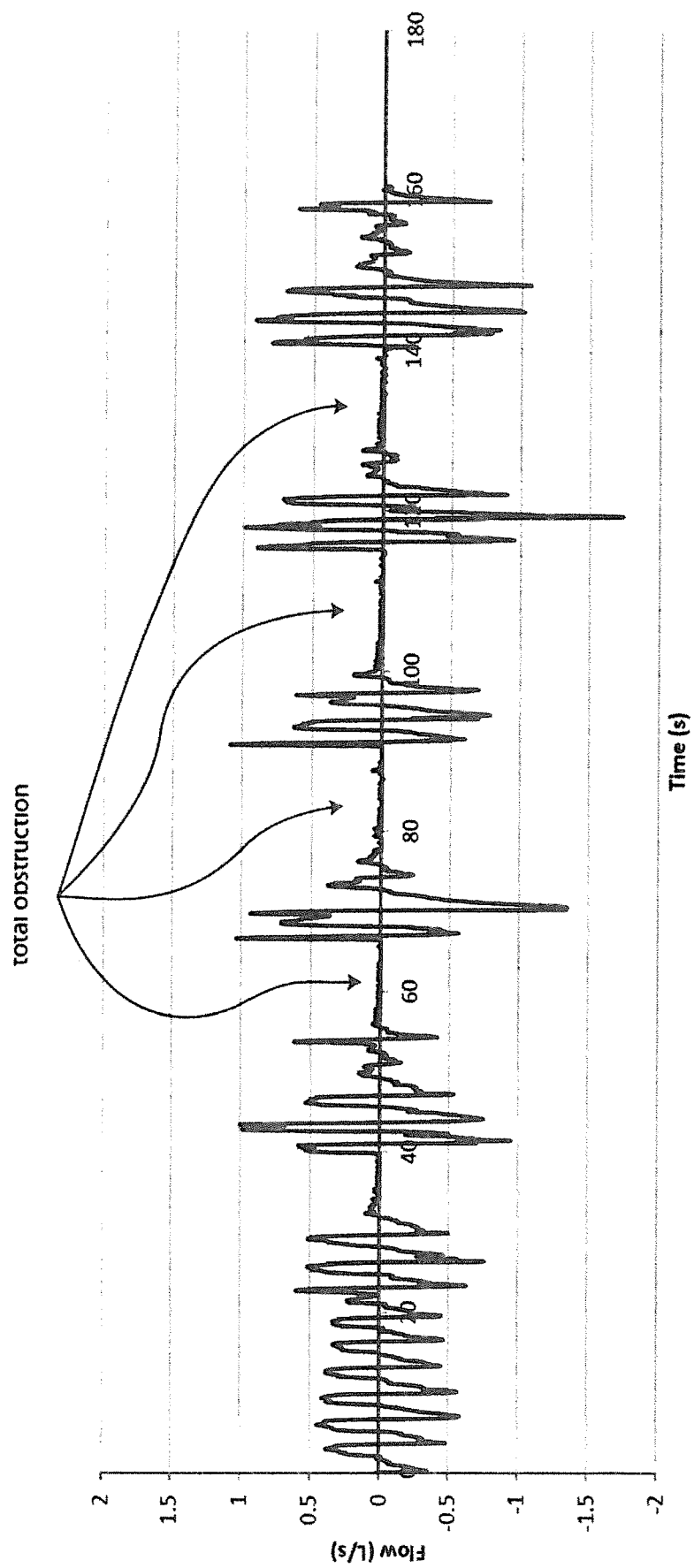

FIG. 6D shows patient flow rate data where the patient is experiencing a series of total obstructive apneas.

Figure 6E:
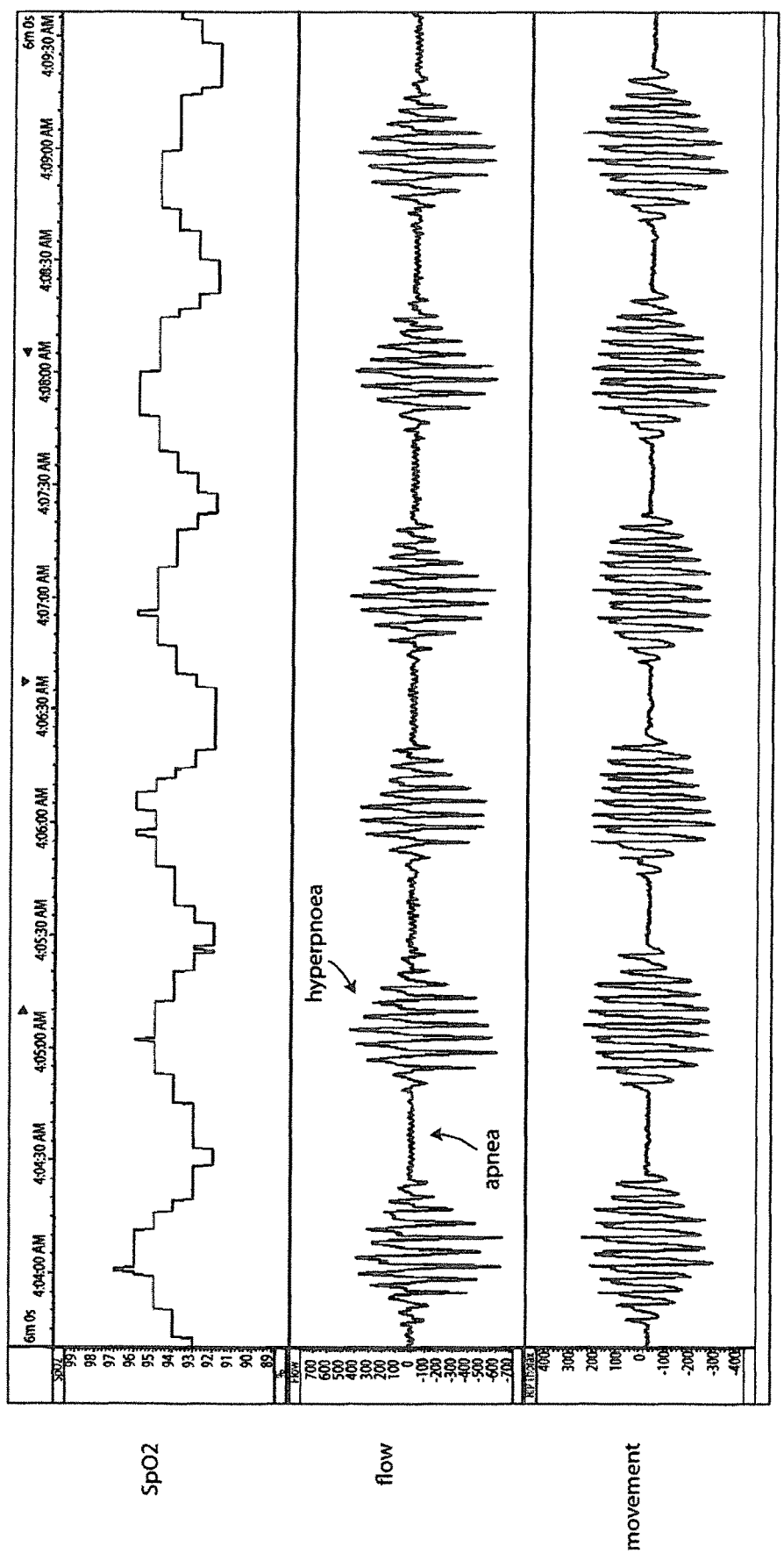

FIG. 6E shows polysomnography data of a patient with Cheyne-Stokes respiration with included apneas.

Figure 6F:
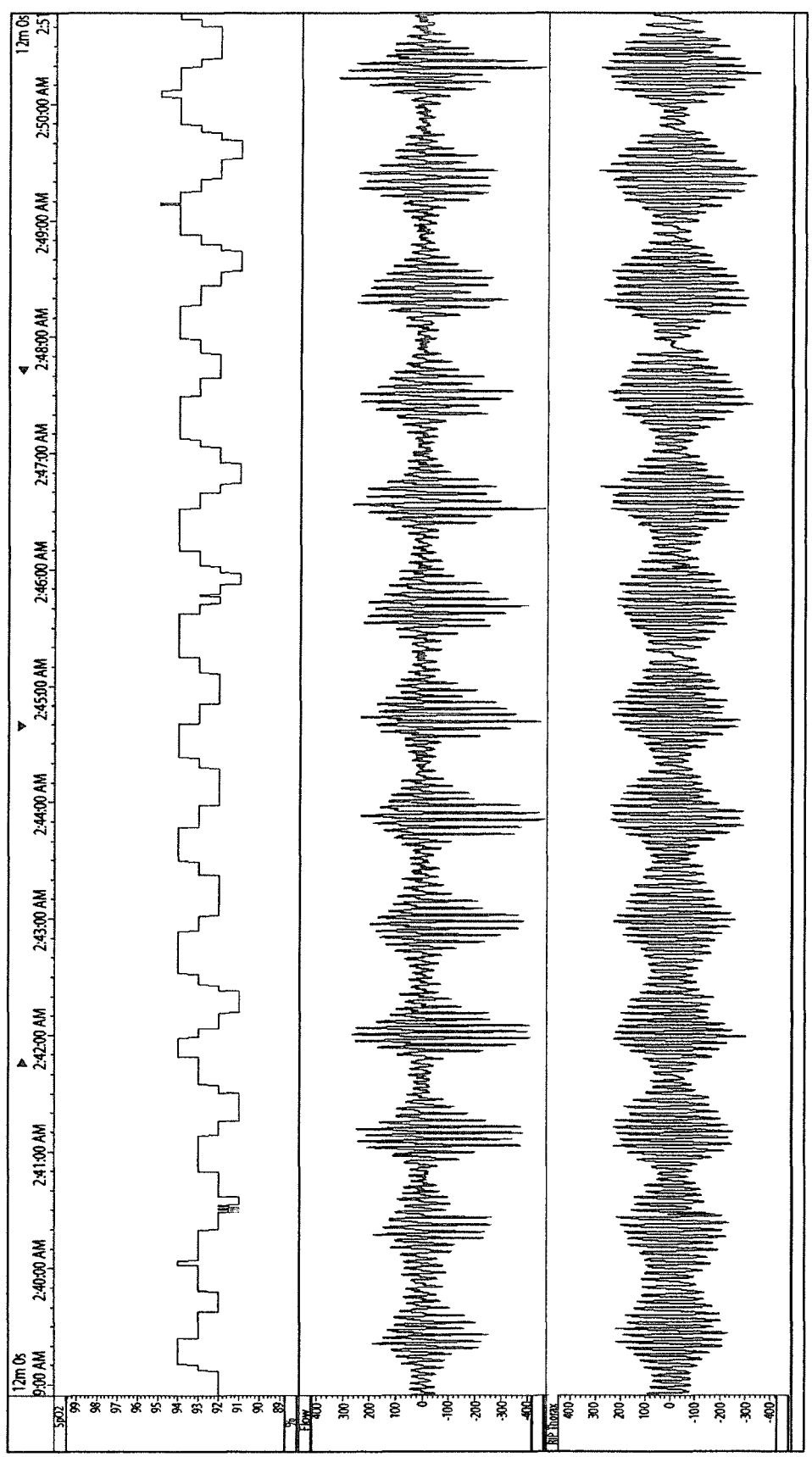

FIG. 6F shows polysomnography data of a patient with Cheyne-Stokes respiration with included hypopneas.

7.7 Monitoring Apparatus

Figure 7A:
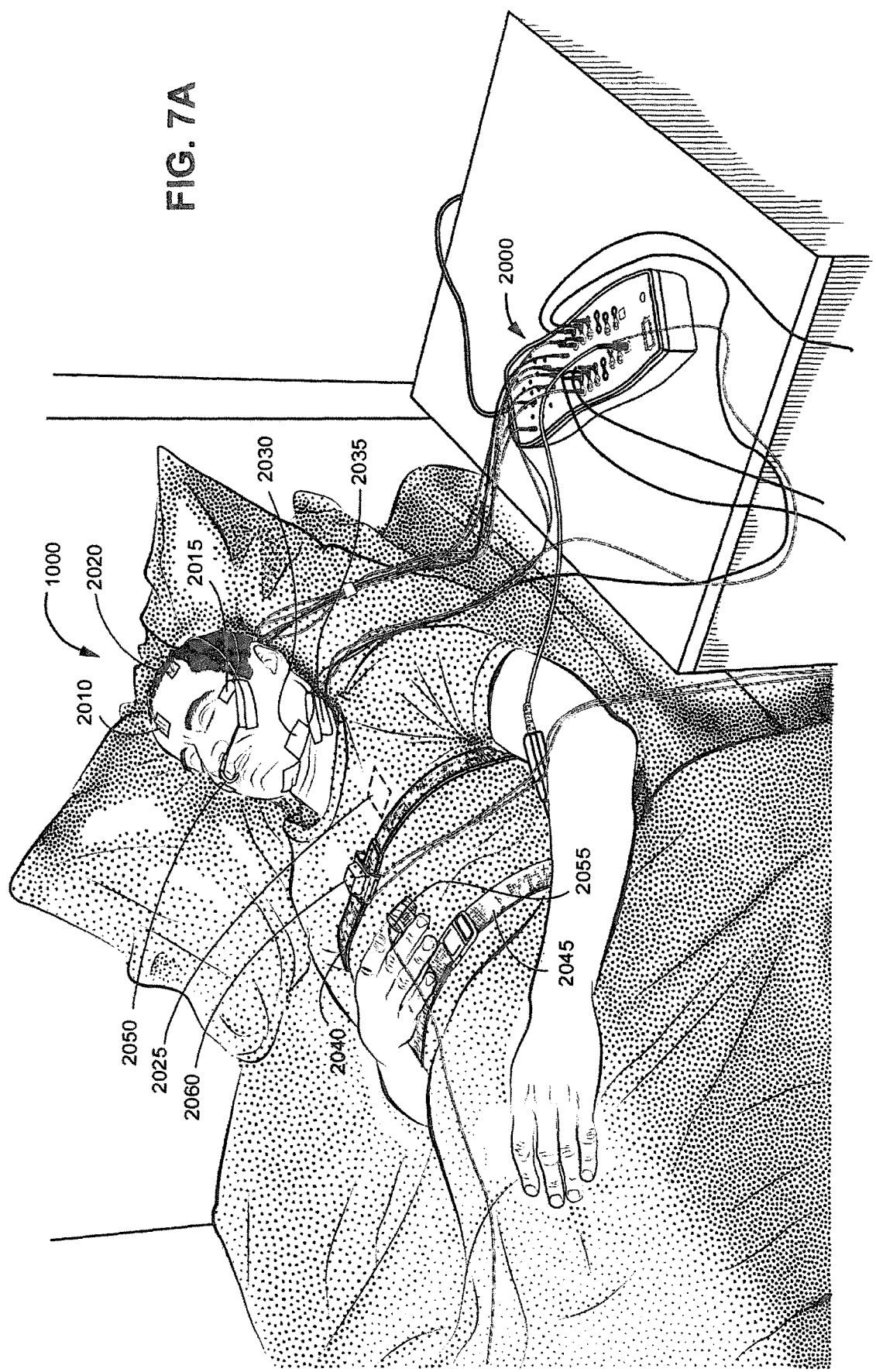

FIG. 7A shows a sleeping patient during sleeping during polysomnography.

Figure 1:
Figures 1, 7B:
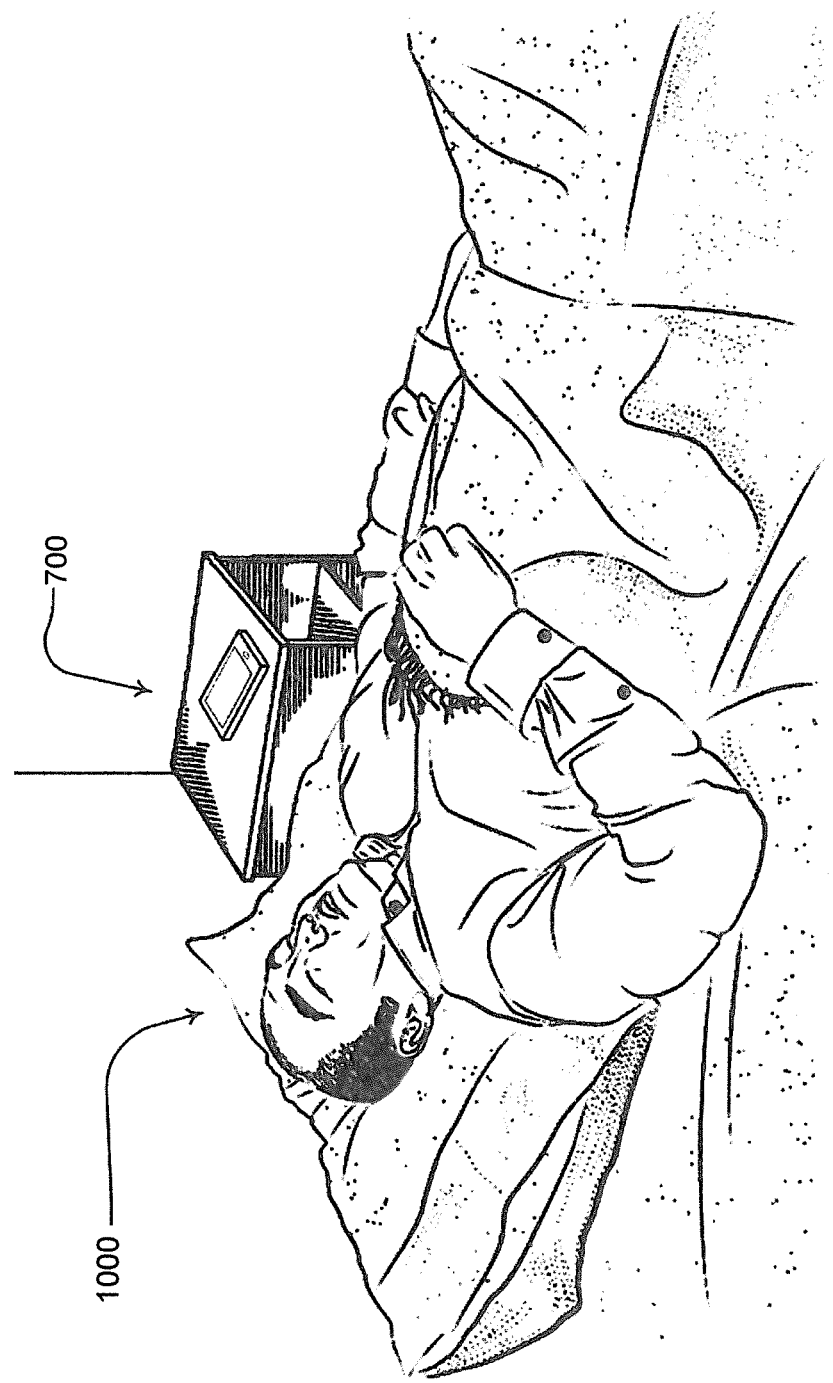
Figures 2, 7B:
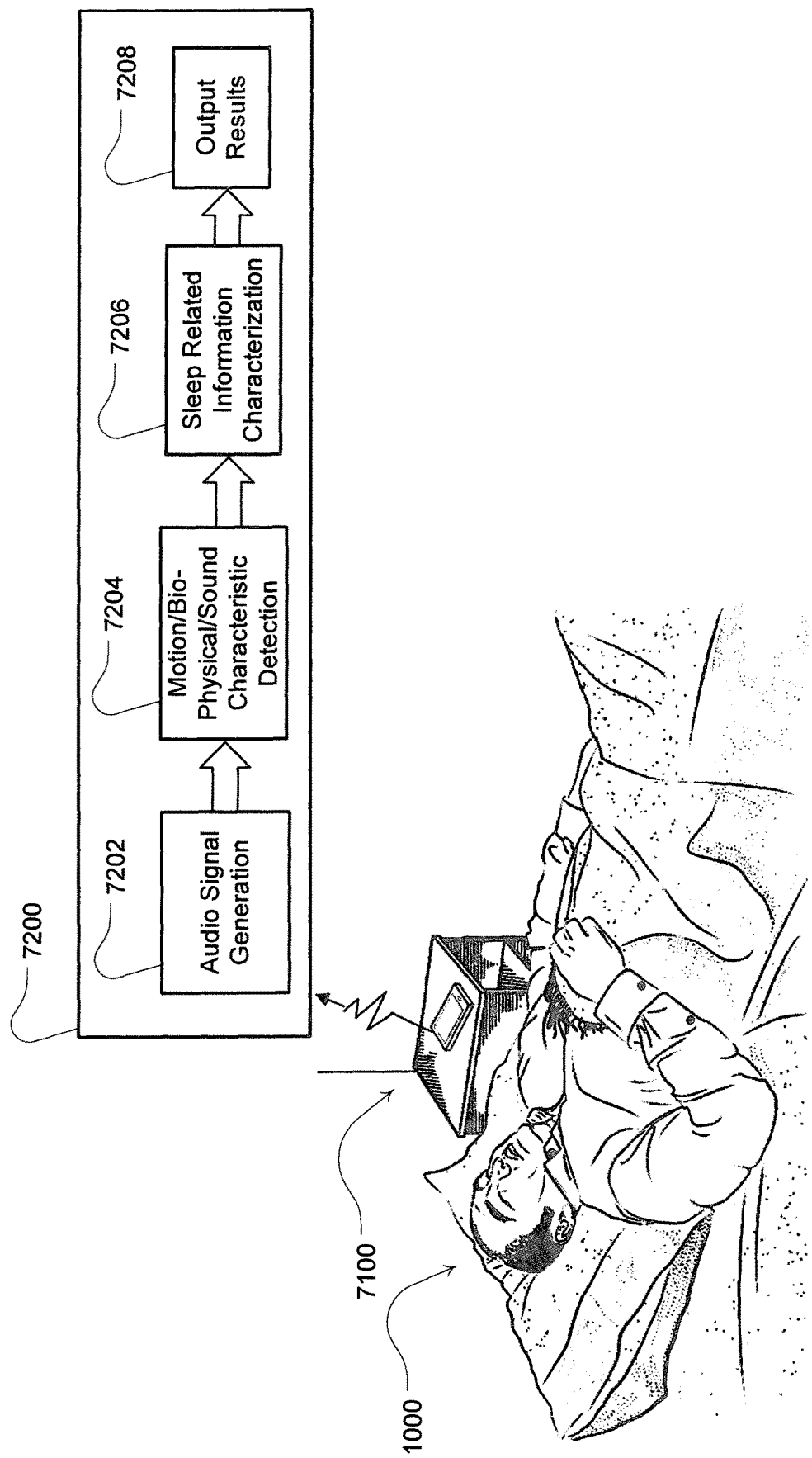
Figures 3, 7B:
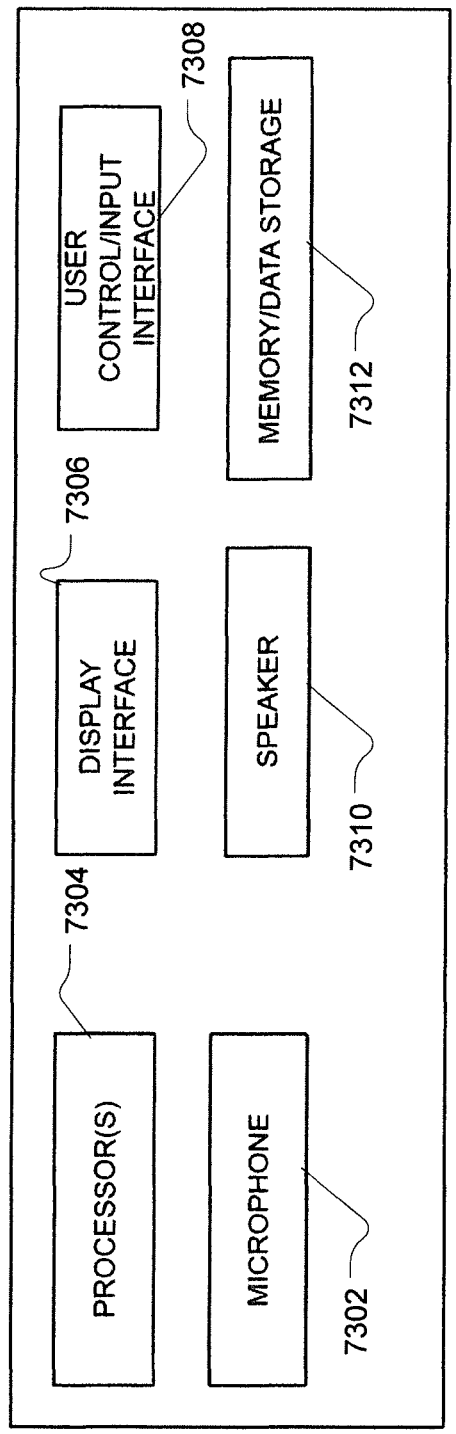

FIG. 7B-1 illustrates an example processing device, such as for acoustic sensing, for monitoring a sleeping person that may be suitable for implementation of the processes of the present technology for diagnosing, monitoring or screening of SDB.

Figure 2:
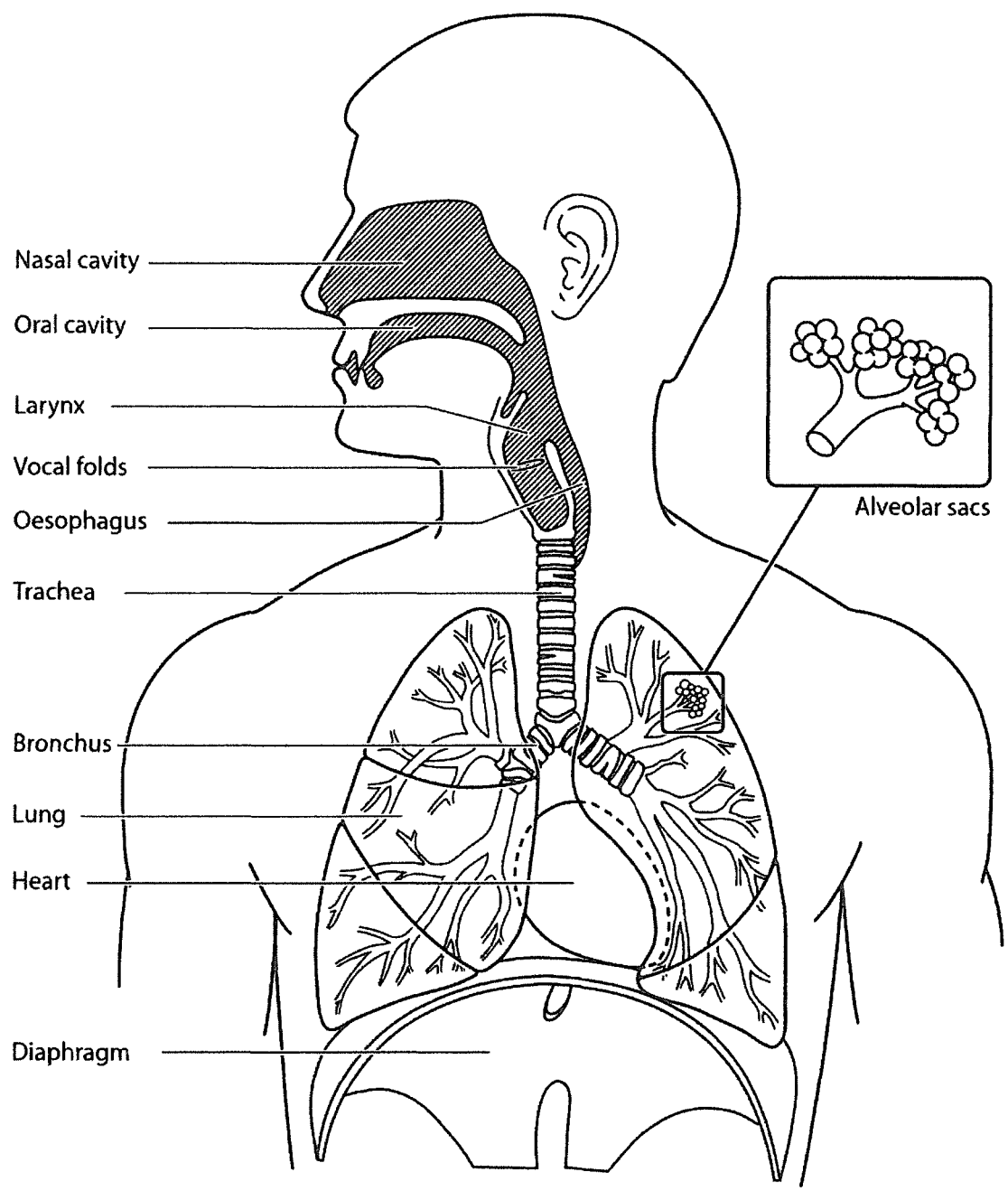

FIG. 7B-2 is a schematic illustration of an example processing device such as the processing device of FIG. 7B-1.

FIG. 7B-2 is conceptual diagram of a mobile computing device, or processing device, configured in accordance with some forms of the present technology, such as with the sensing and/or SDB screening technologies described herein.

Figures 1, 7C:
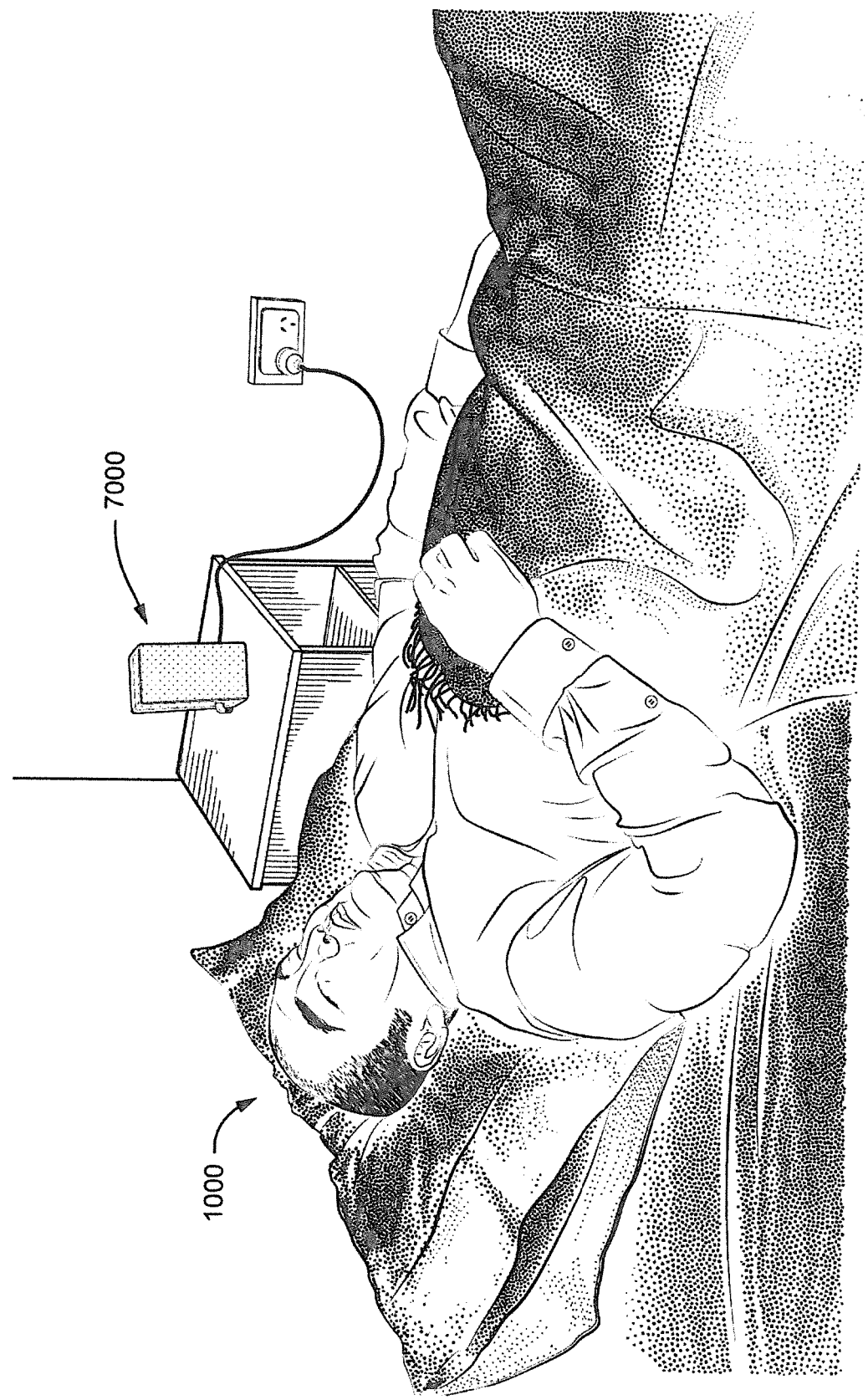
Figures 2, 7C:
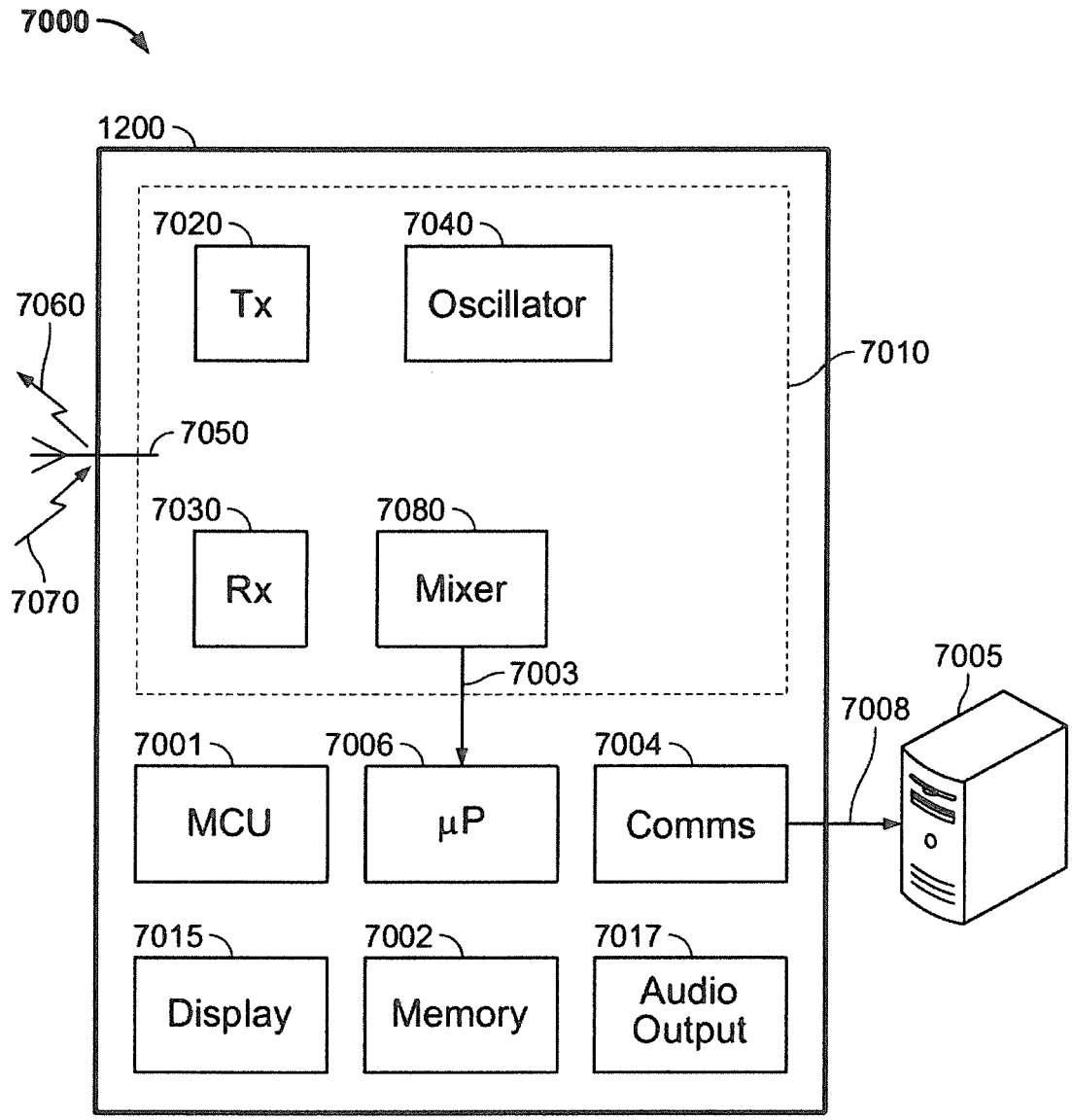

FIG. 7C-1 shows an example apparatus, such as with radio frequency sensing, for monitoring a sleeping patient in accordance with one form of the present technology.

FIG. 7C-2 is a block diagram illustrating the monitoring apparatus of FIG. 7C-1 in more detail.

Figure 8:
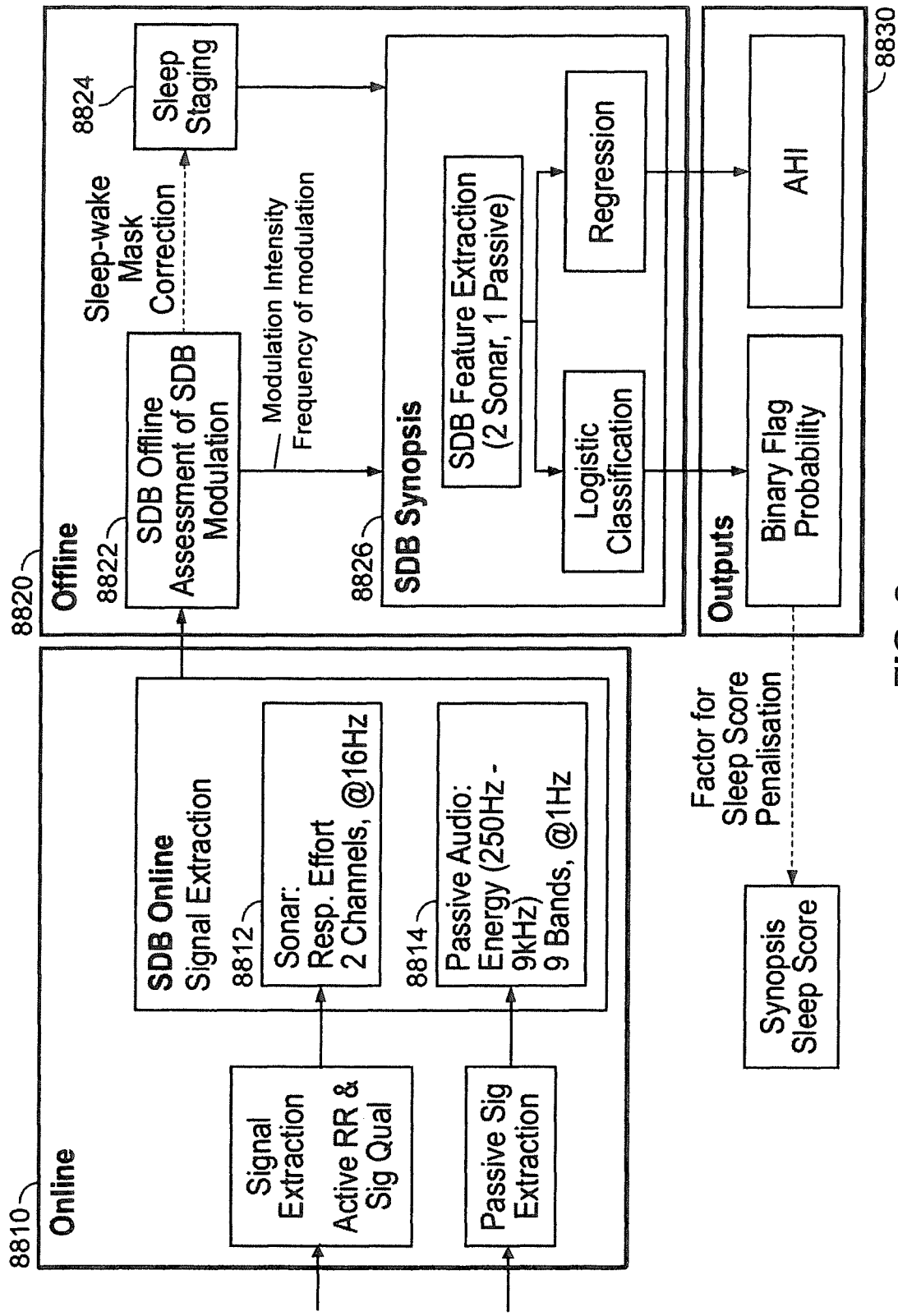

FIG. 8 illustrates example processes or modules for a processing device such as for processing of sensing signals to provide an output indication of a sleep disordered breathing condition in some versions of the present technology.

Figure 8A:
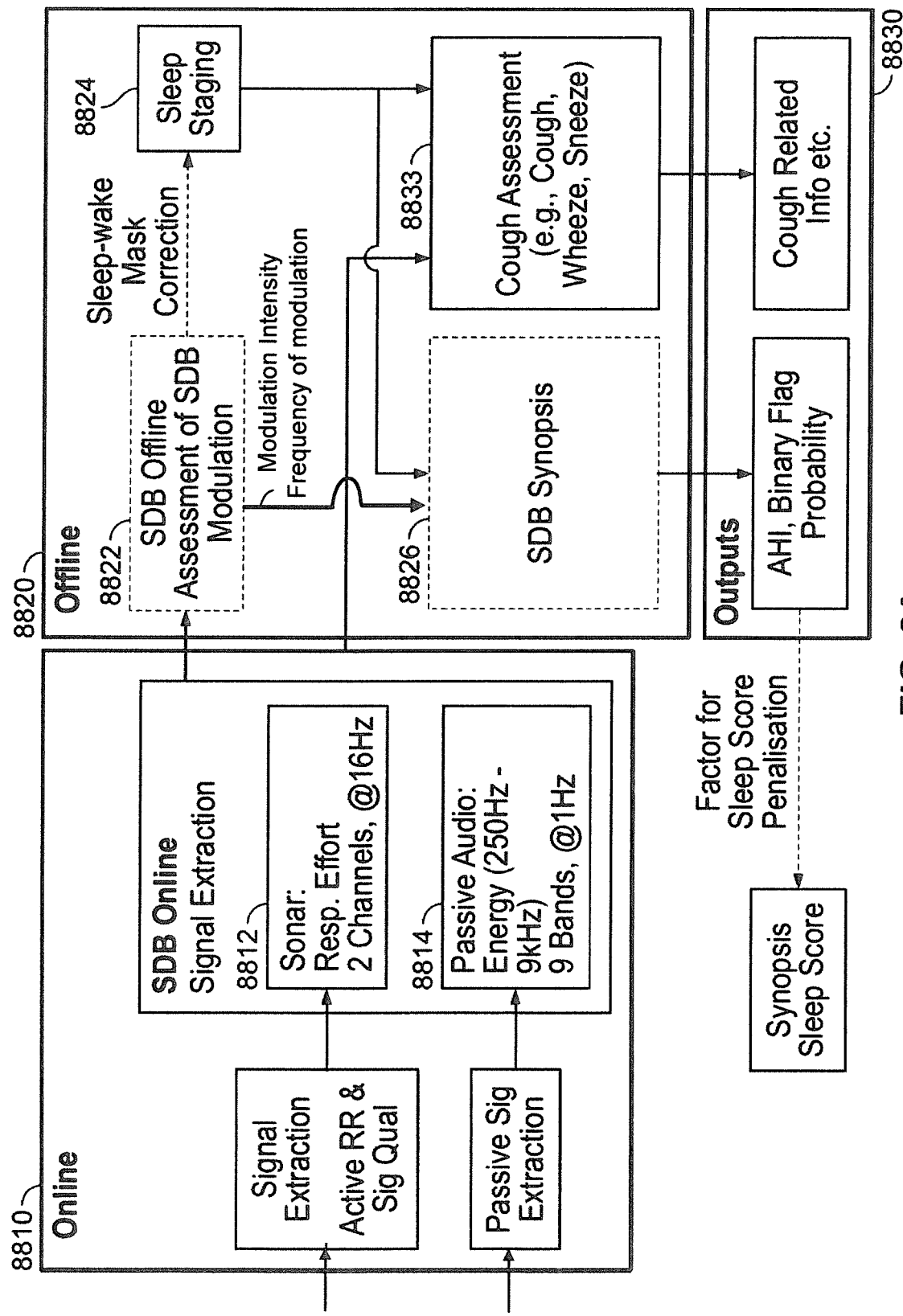

FIG. 8A illustrates example processes or modules for a processing device such as for processing of sensed signals to provide an output indication of cough condition, events and/or types in some versions of the present technology.

Figure 8B:
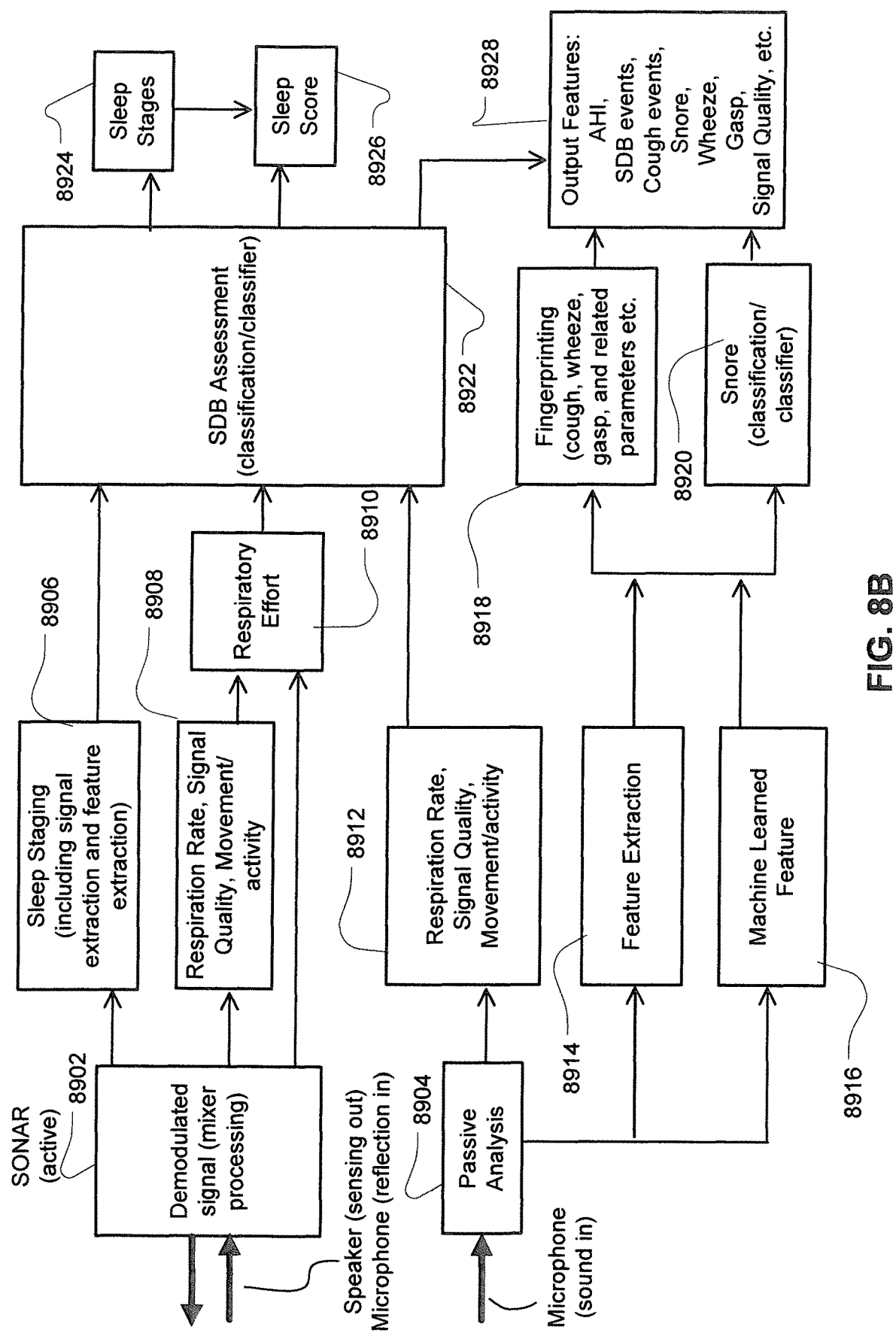

FIG. 8B illustrates further example processes or modules for a processing device such as for processing of sensed signals to provide an output indication of cough condition, events and/or types in some versions of the present technology, among others.

Figure 8C:
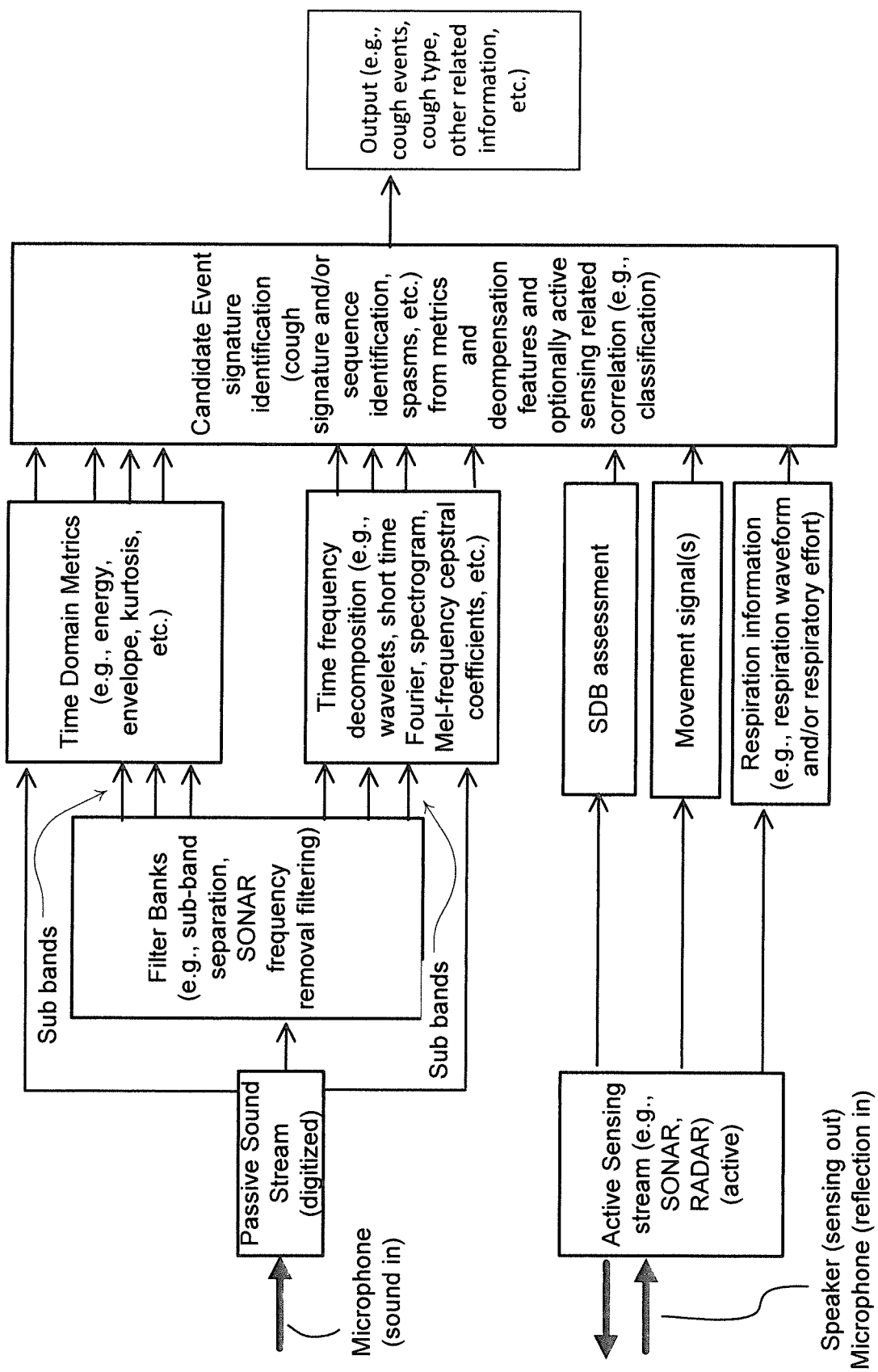

FIG. 8C illustrates example processes or modules to detect characteristic patterns of snoring, snuffling, coughing or breathing difficulties with passive and/or active sensing techniques described herein, such as for implementation in the cough assessment systems illustrated in FIG. 8A or 8B.

Figure 8D:
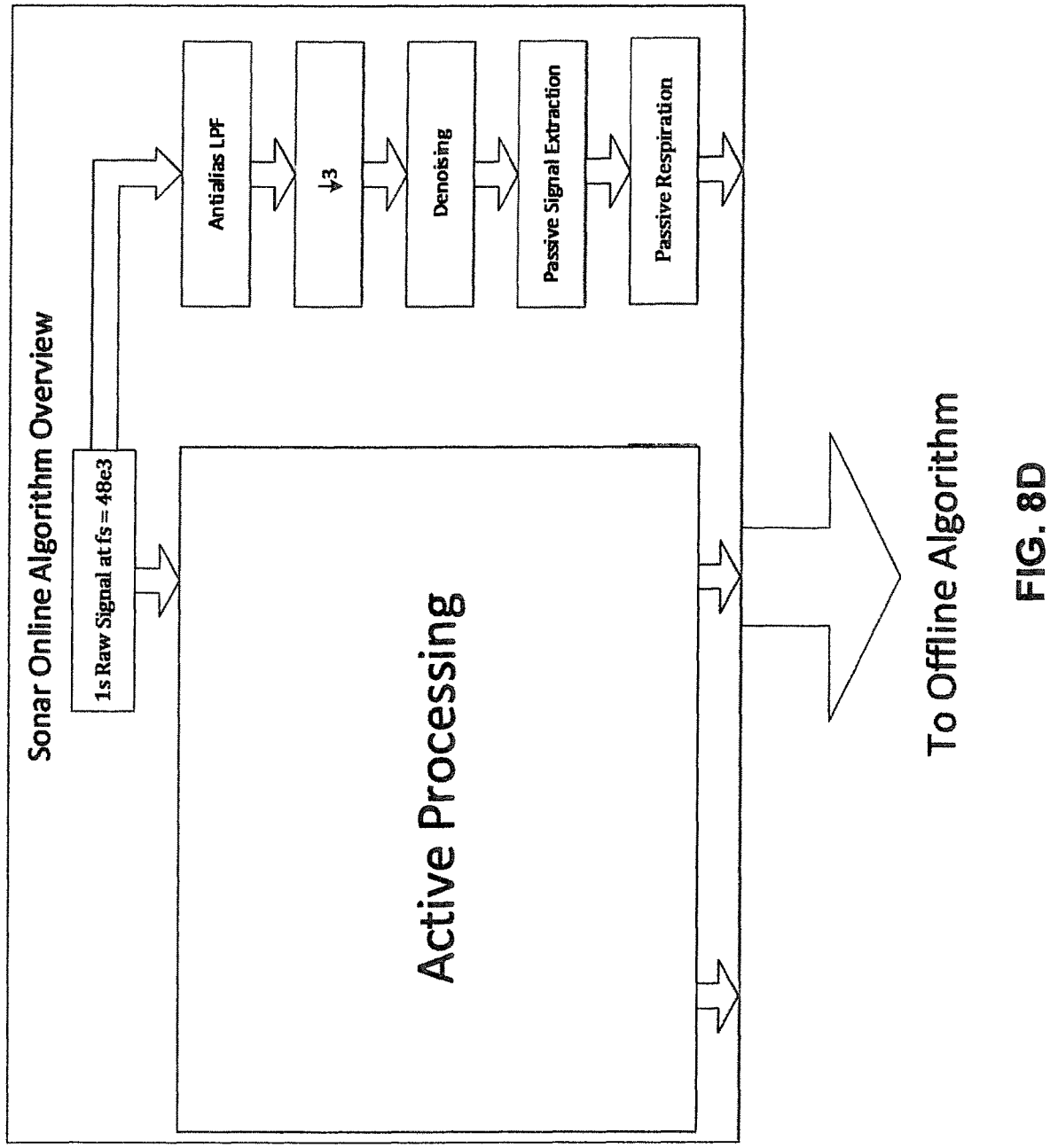

FIG. 8D illustrates example processes or modules for processing for active and passive sensing streams that may be suitable for implementation with the techniques illustrated in, for example, FIG. 8C; with particular emphasis on example processes or modules for processing of a passive sensing stream.

Figure 9:
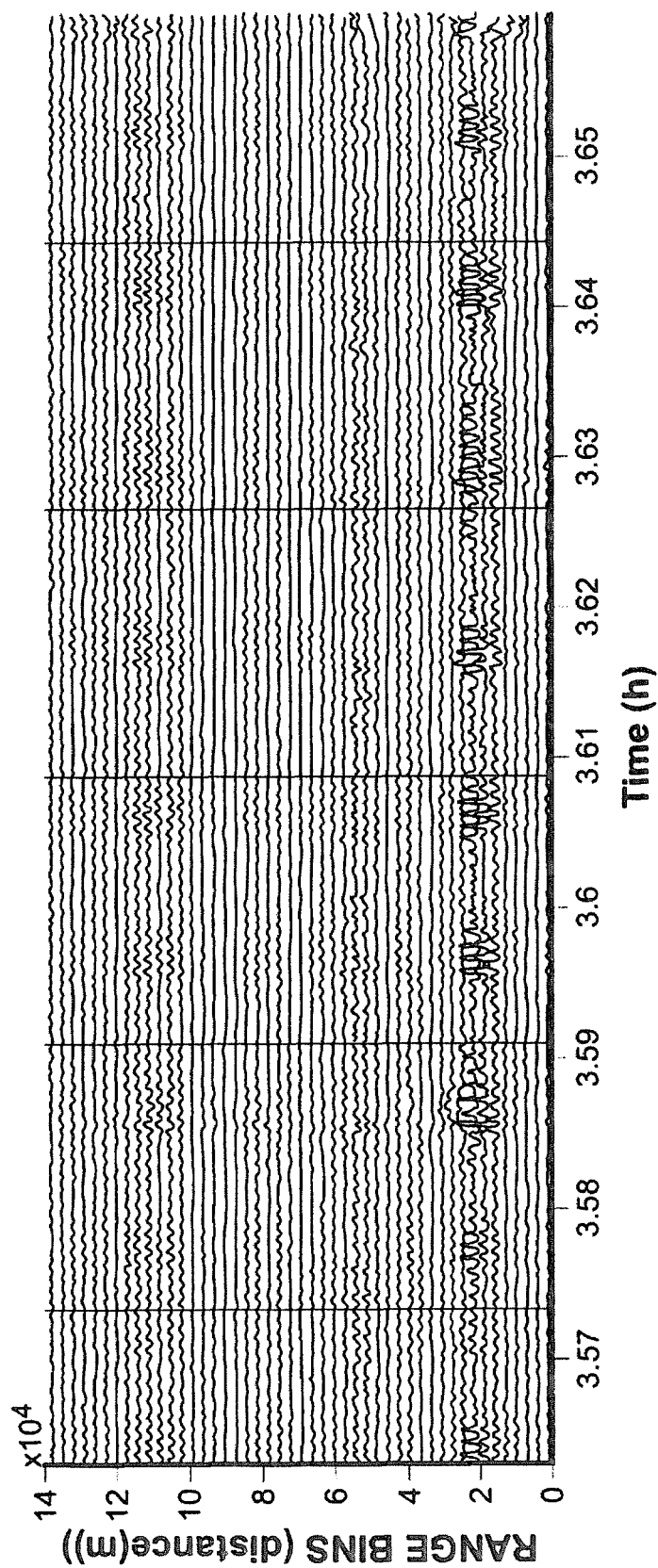

FIG. 9 illustrates various motion signals relating to respiratory effort in different range bins representing motion at different sensing distances from a sensor, such as by implementing range gating with an of the motion sensing devices of the present technology.

Figure 10:
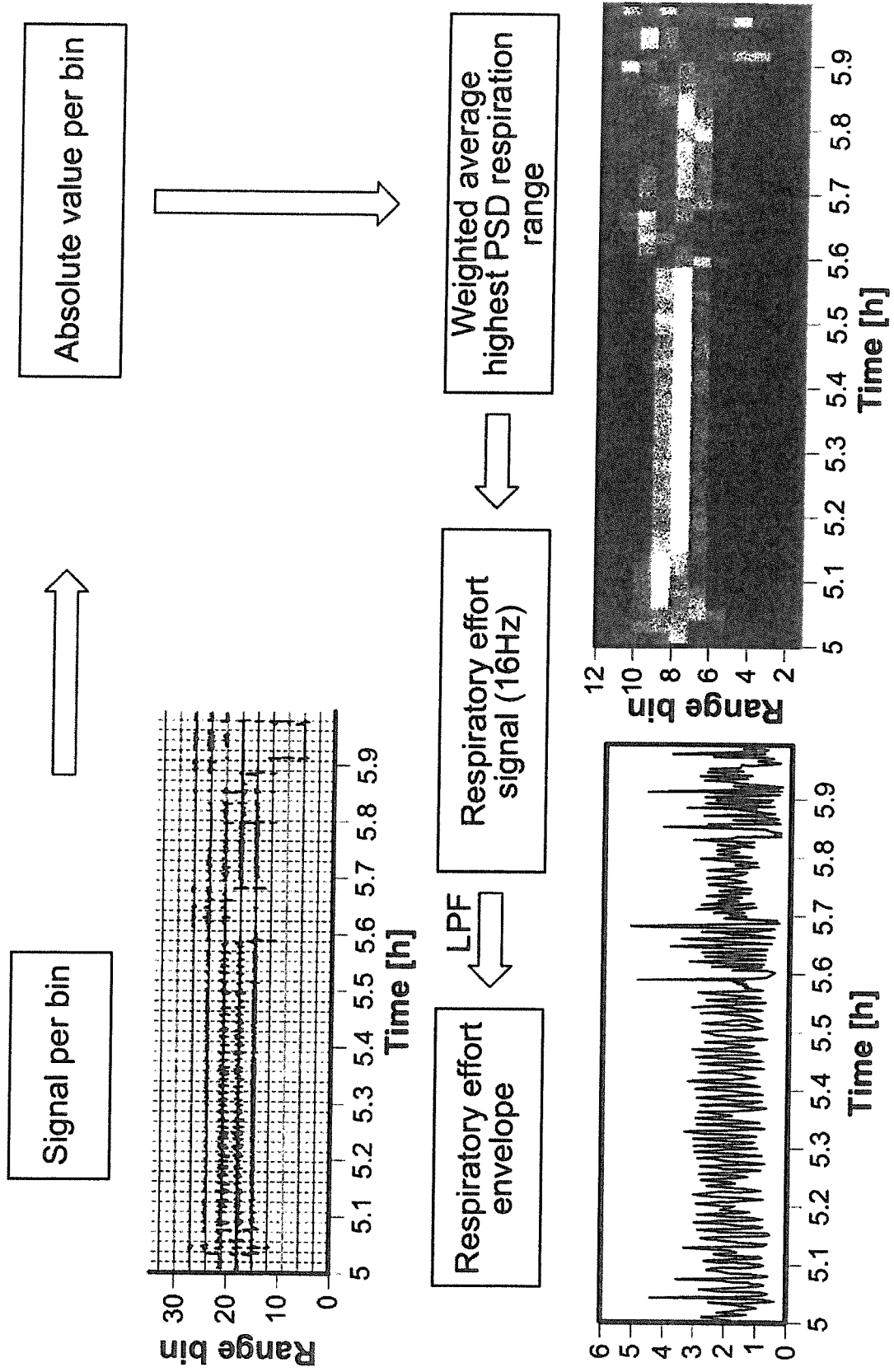

FIG. 10 illustrates a process for signal processing of the motion signals relating to different ranges for extraction of information concerning respiratory effort to produce a respiratory effort signal in some versions of the present technology.

Figure 11:
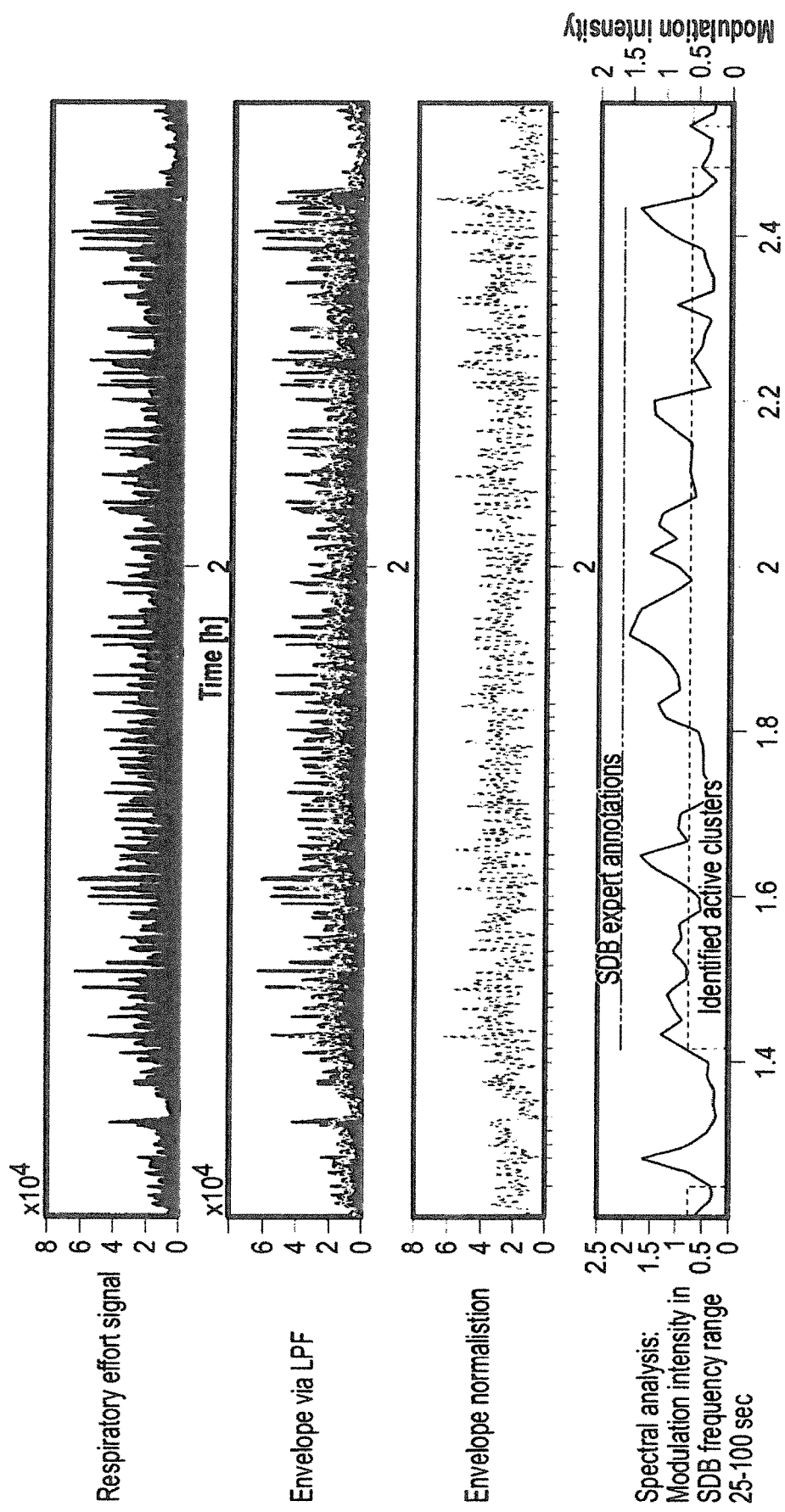

FIG. 11 illustrates a process for signal processing of a respiratory effort signal by spectral analysis in some versions of the present technology for identification of active clusters relating to SDB.

Figure 12:
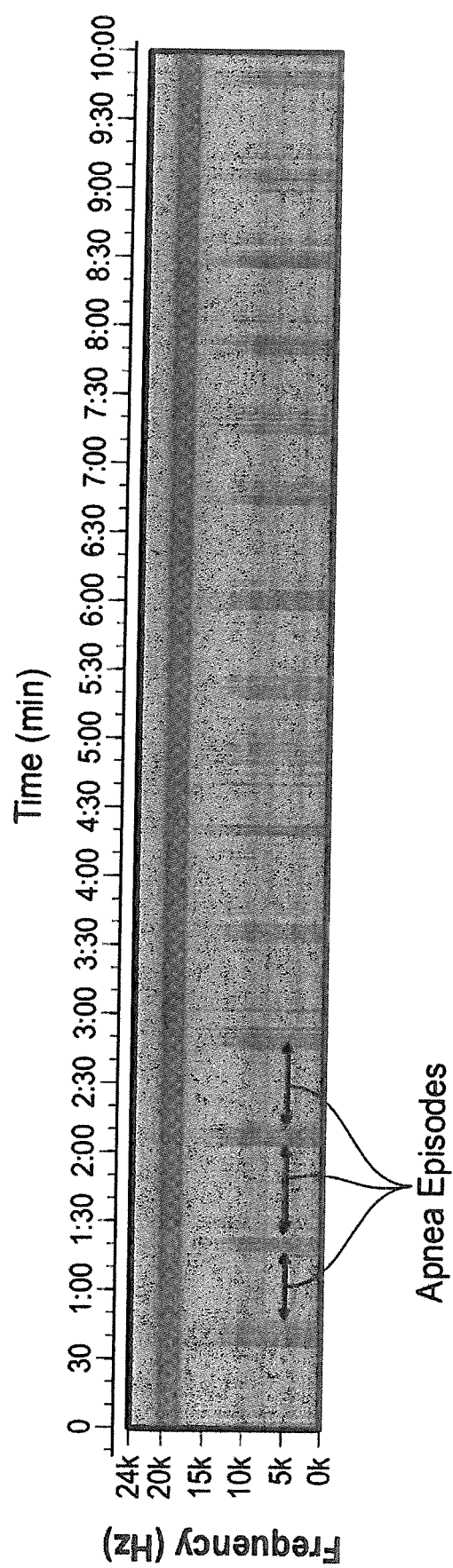

FIG. 12 illustrates a spectrogram of an example acoustic signal generated with sound sensor (e.g., microphone) such as with passive sound detection implemented by a processing device described herein.

Figure 13:
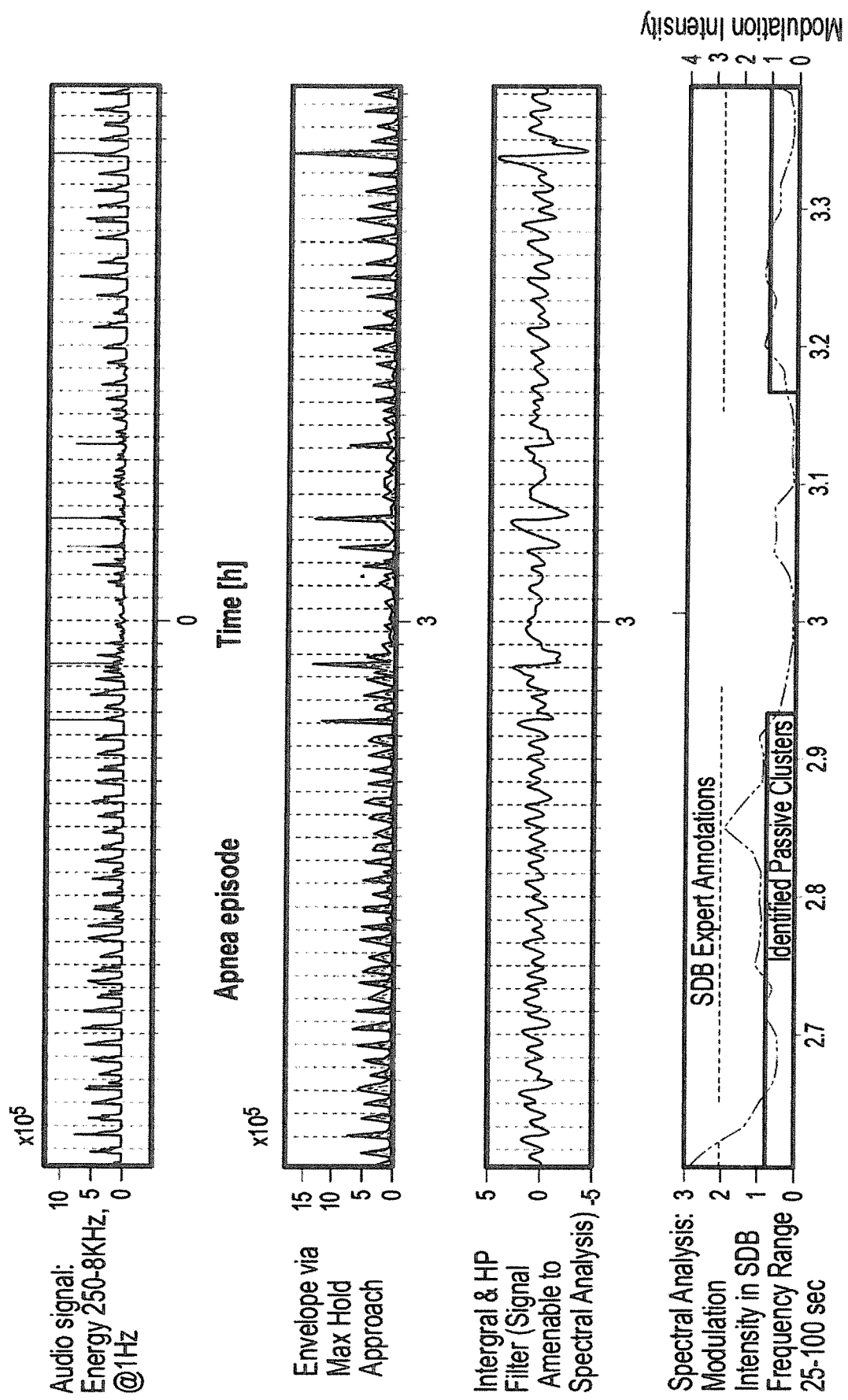

FIG. 13 illustrates a process for signal processing of an acoustic signal, such as an acoustic signal generated with sound sensor by passive sound detection, in some versions of the present technology for identification of passive clusters relating to SDB.

Figure 14:
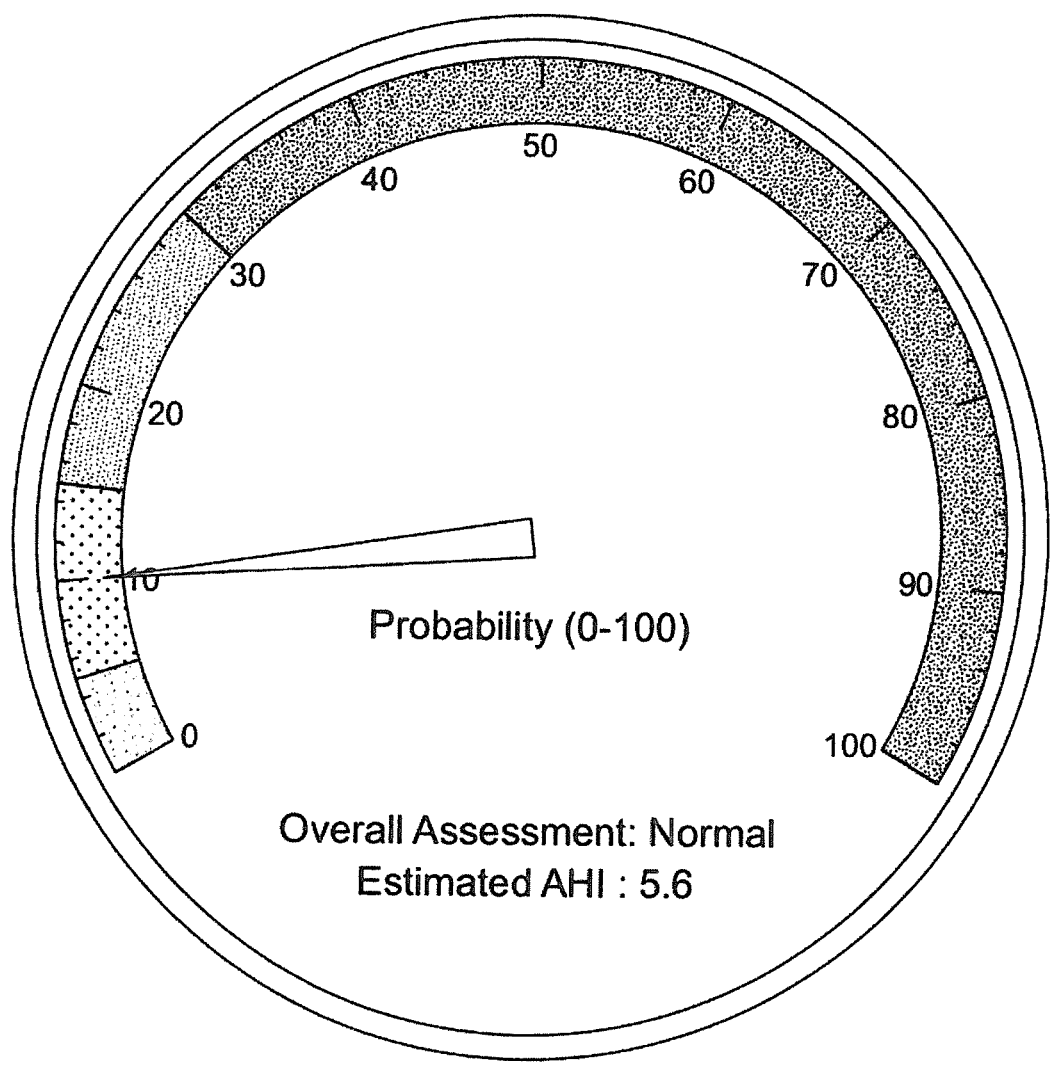

FIG. 14 illustrates a graphic SDB risk identifier that may be generated in some versions of the present technology, illustrating a normal assessment of SDB risk and an estimated count of apnea and/or hypopnea events.

Figure 15:
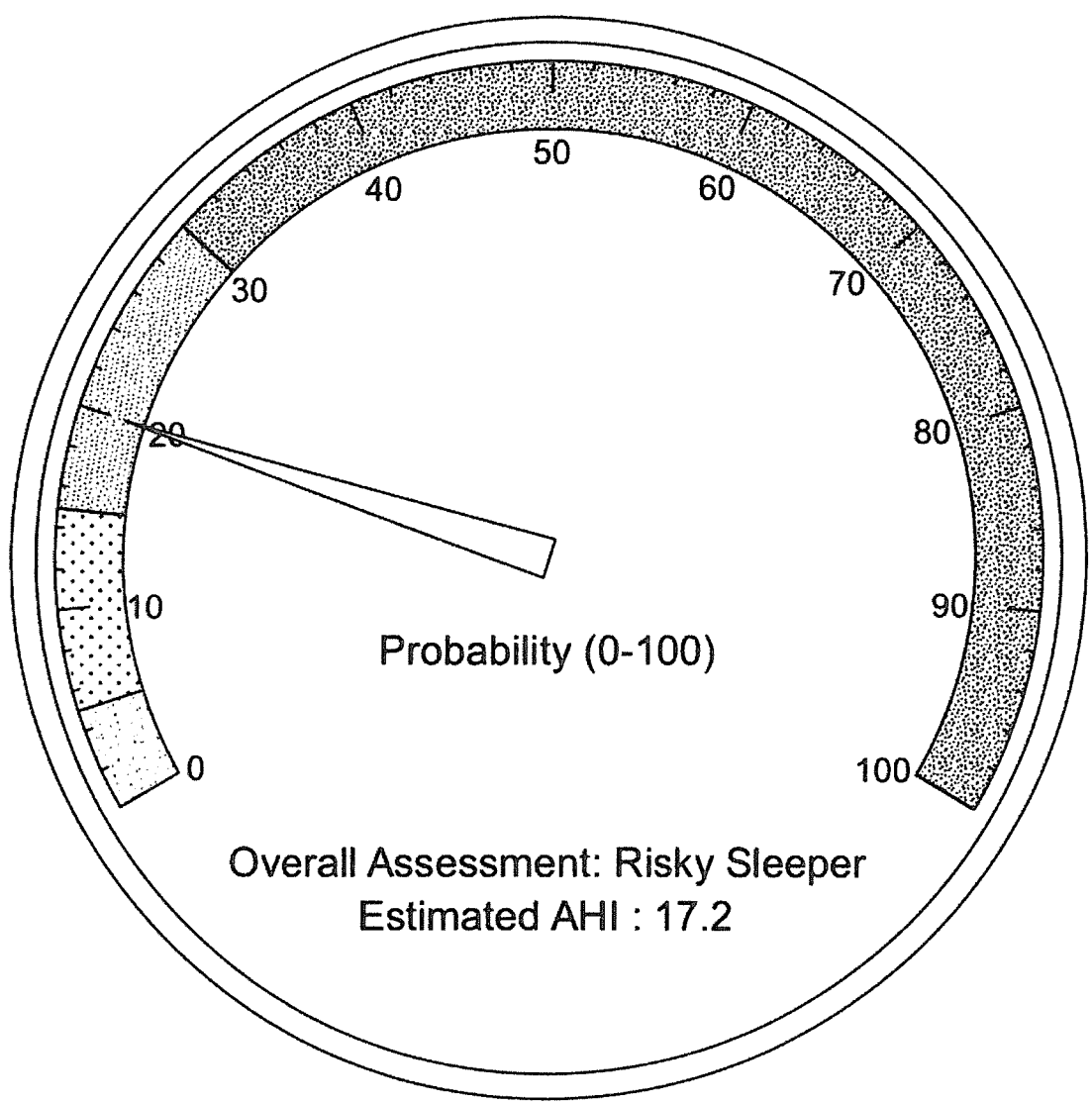

FIG. 15 illustrates a graphic SDB risk identifier that may be generated in some versions of the present technology, illustrating a risky sleeper assessment of SDB risk and an estimated count of apnea and/or hypopnea events. The meter shows a moderate risk with a calculated probability in an example range of 15 to 30 percent.

Figure 16:
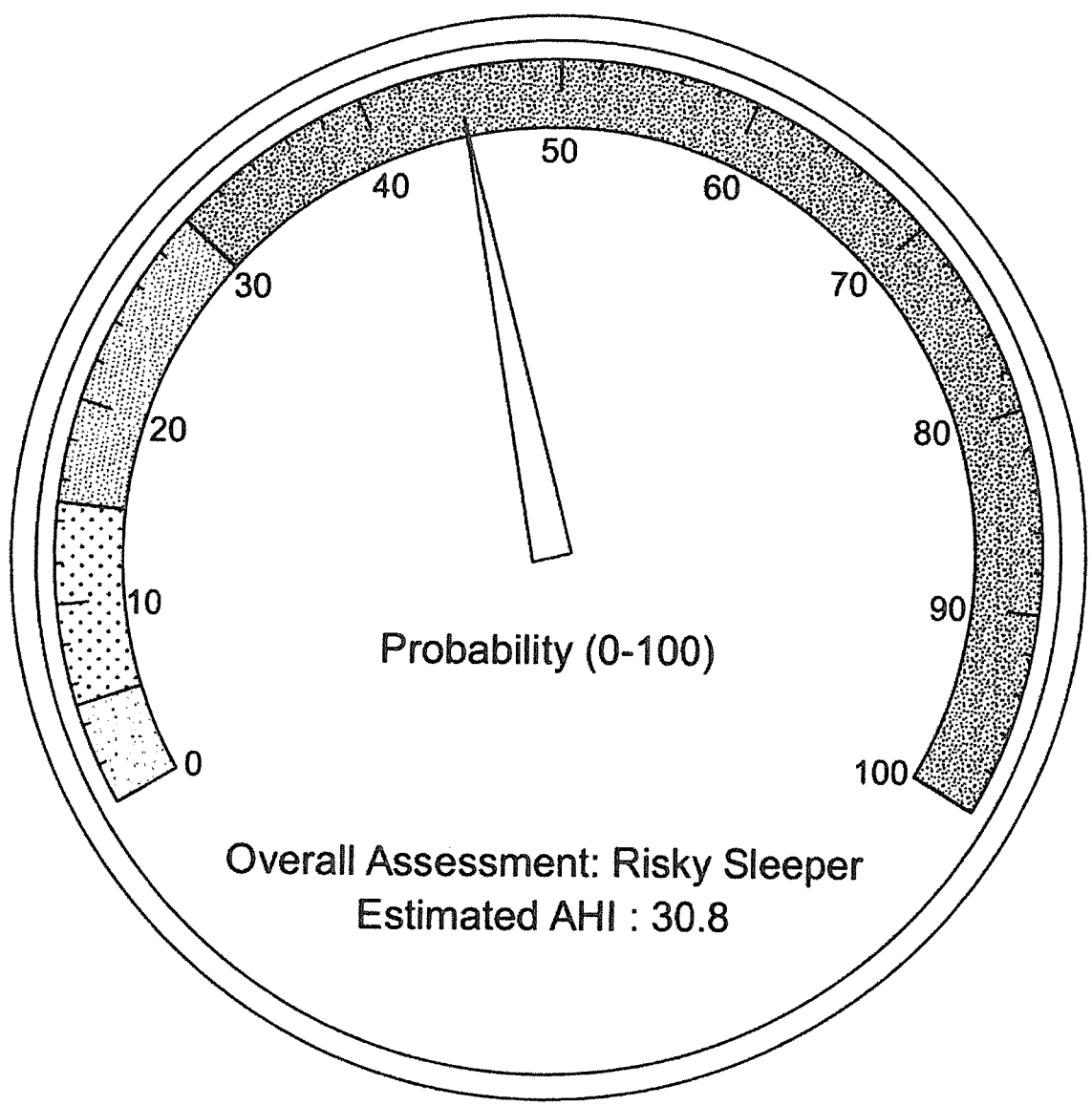

FIG. 16 illustrates a graphic SDB risk identifier that may be generated in some versions of the present technology, illustrating a risky sleeper assessment of SDB risk and an estimated count of apnea and/or hypopnea events. The meter shows a high risk with a calculated probability in an example range of 30 to 100 percent.

Figure 17:
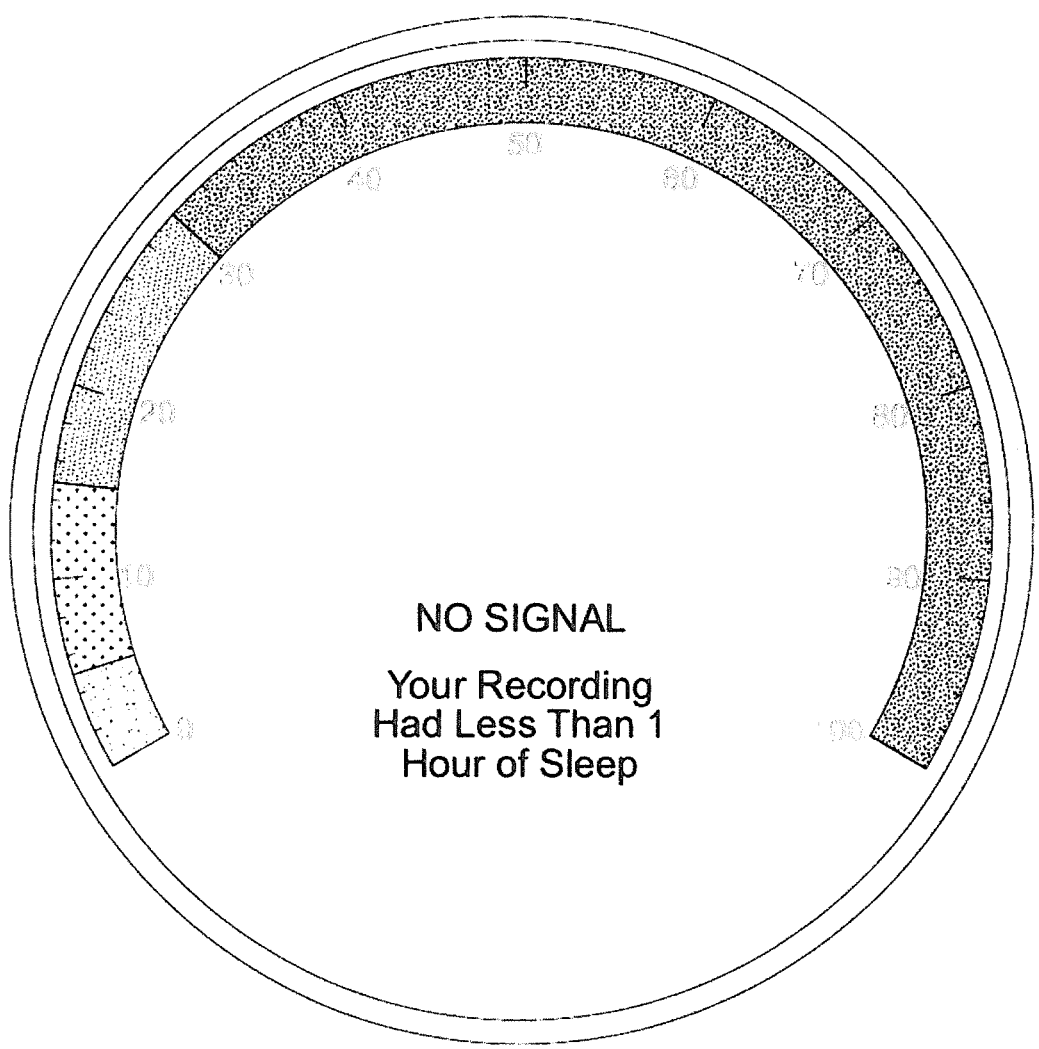
Figure 18:
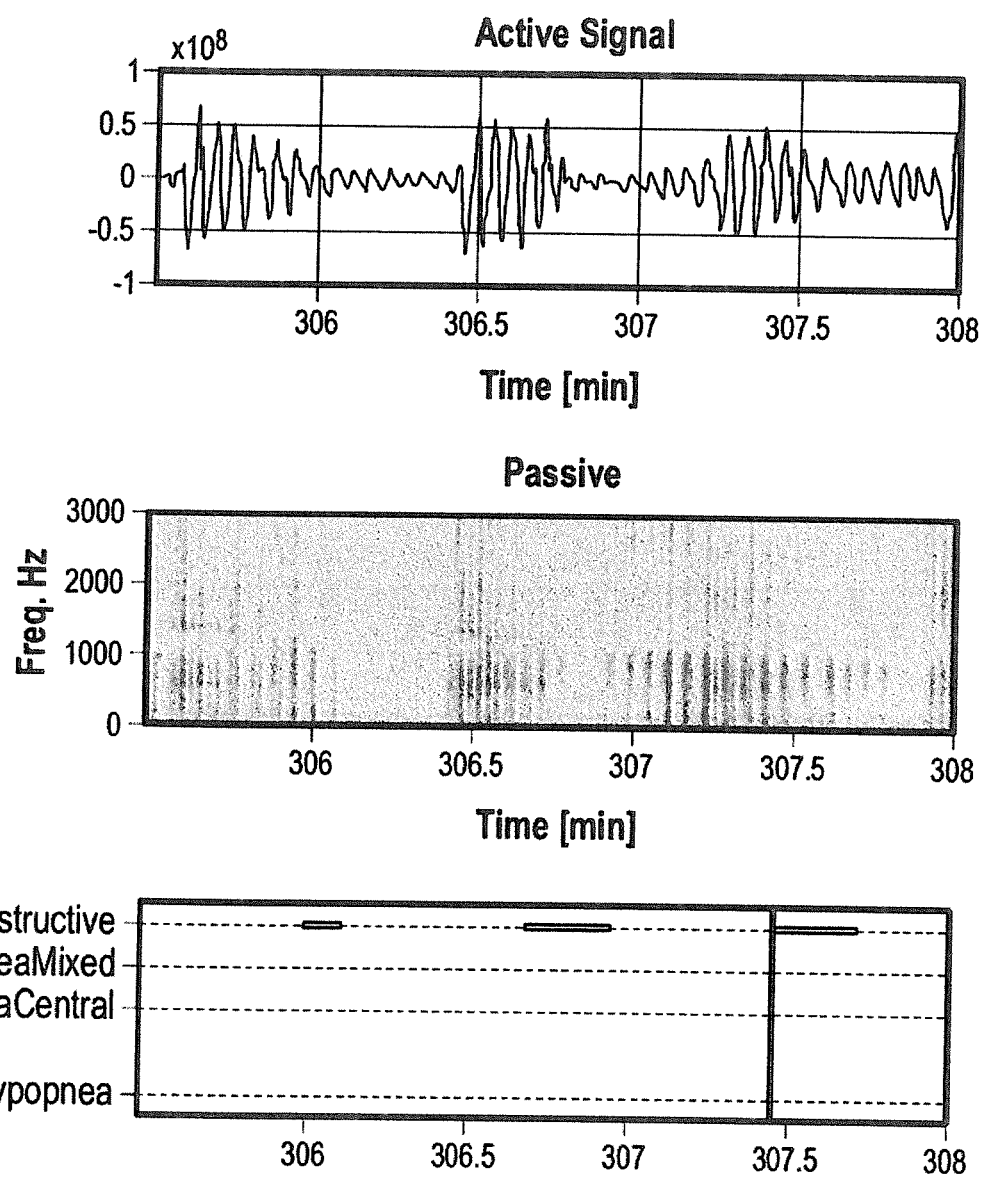
Figure 19:
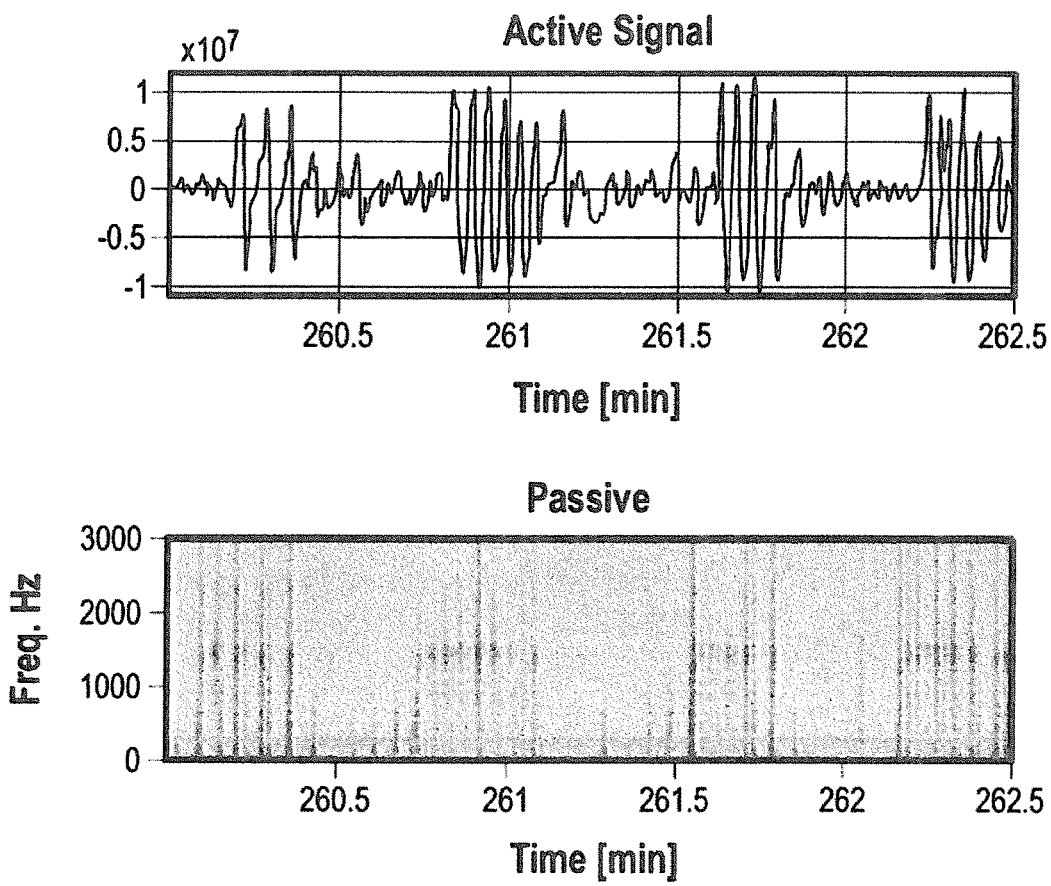
Figure 19:
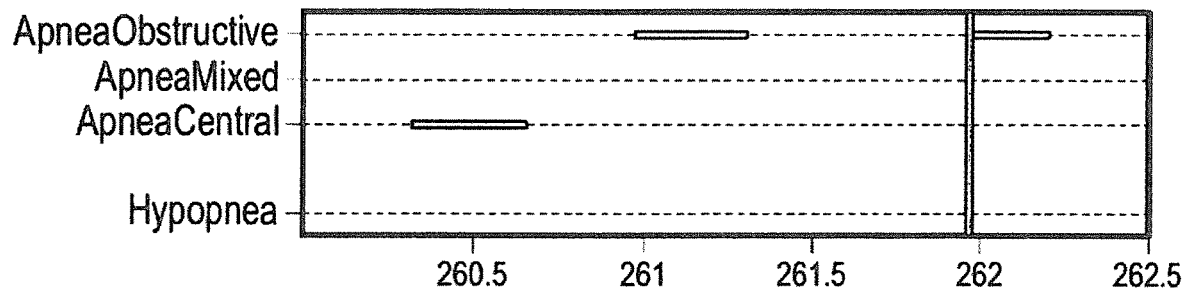
Figure 20:
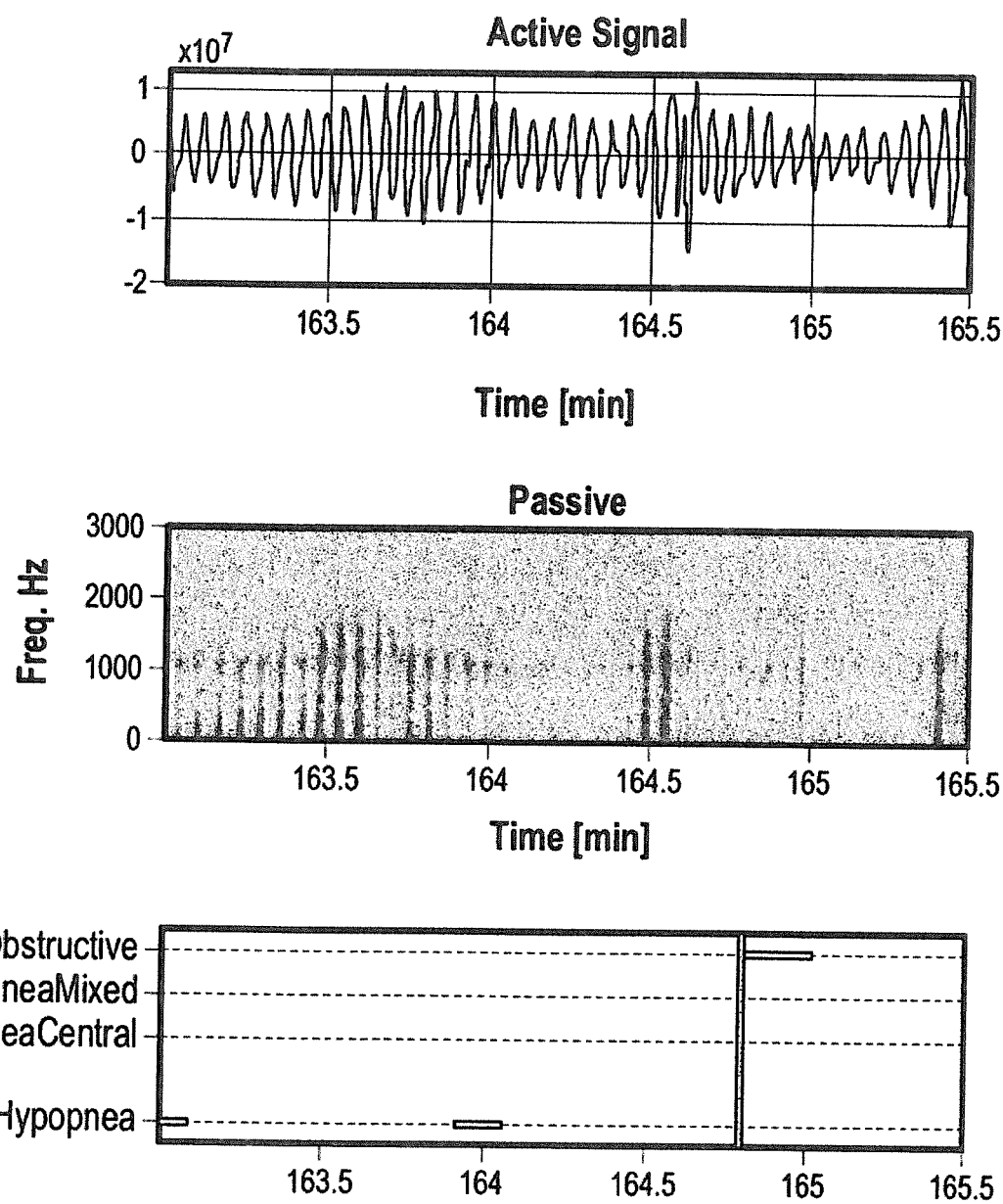
Figure 21:
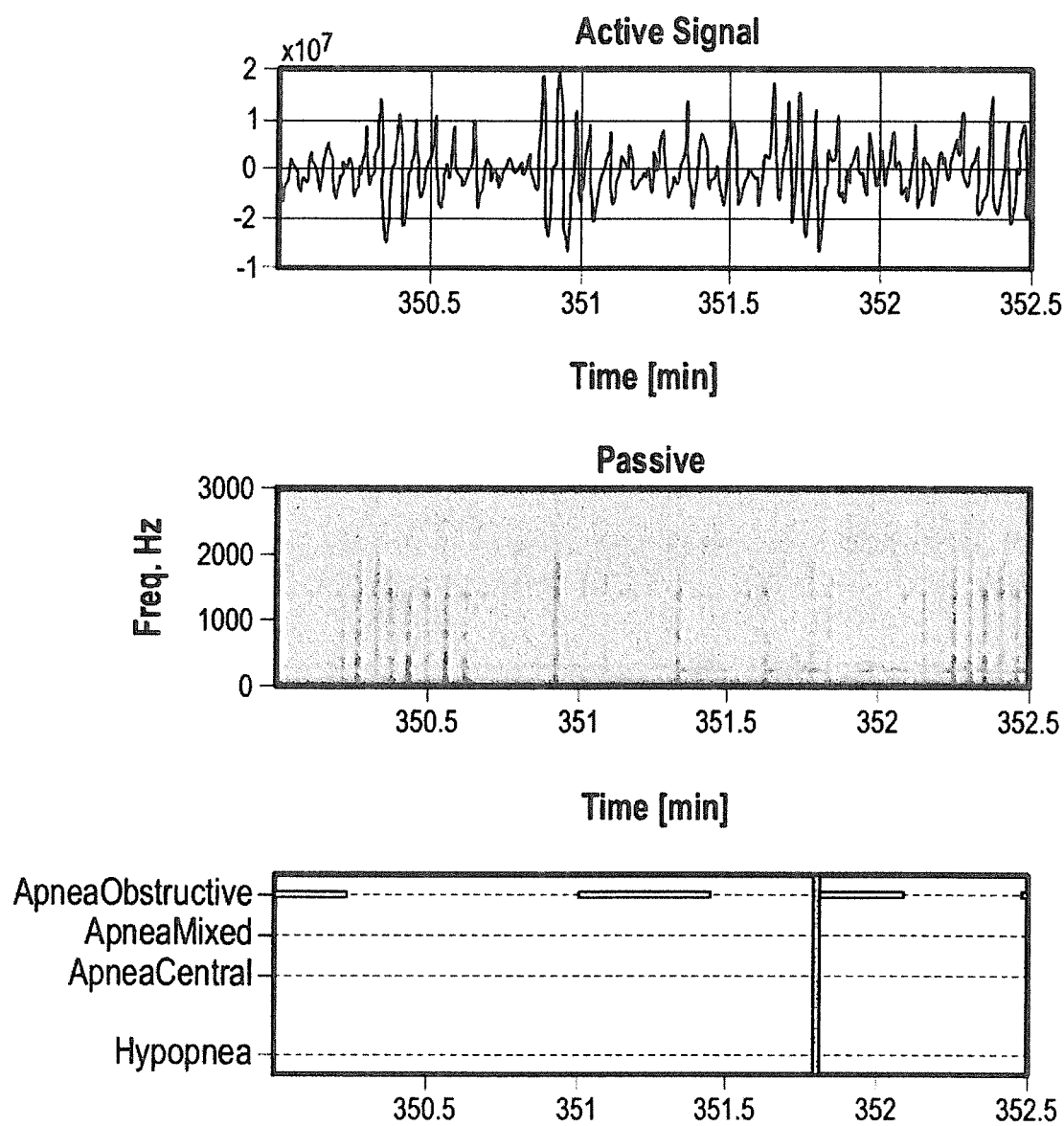
Figure 22:
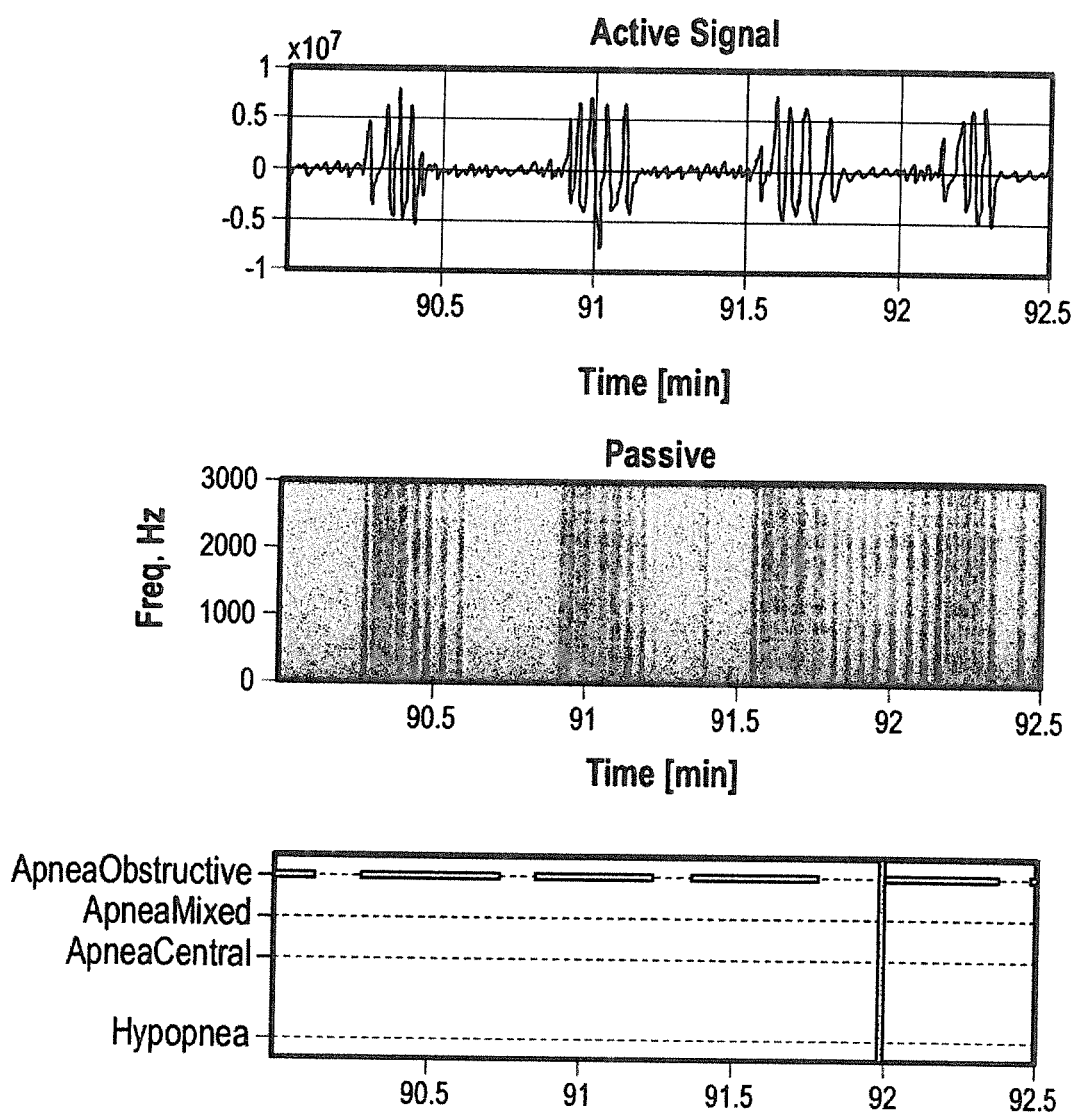
Figure 23:
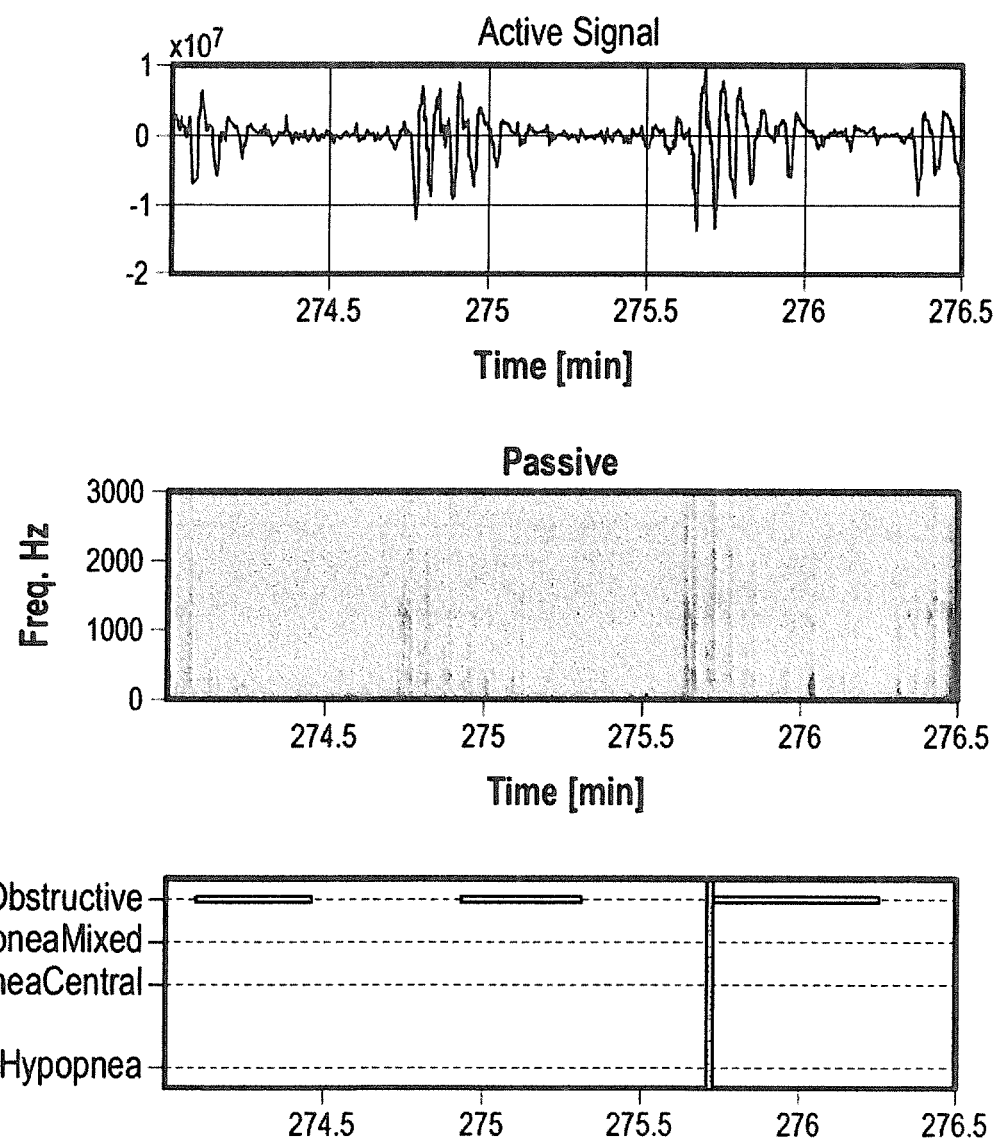
Figure 24:
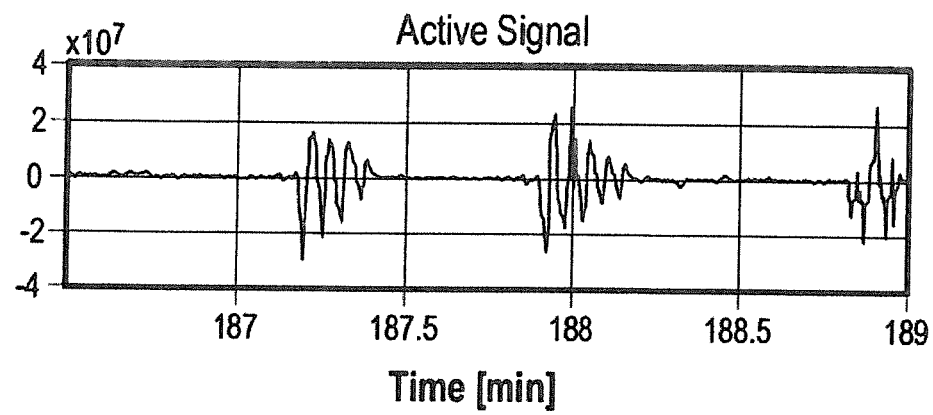
Figure 24:
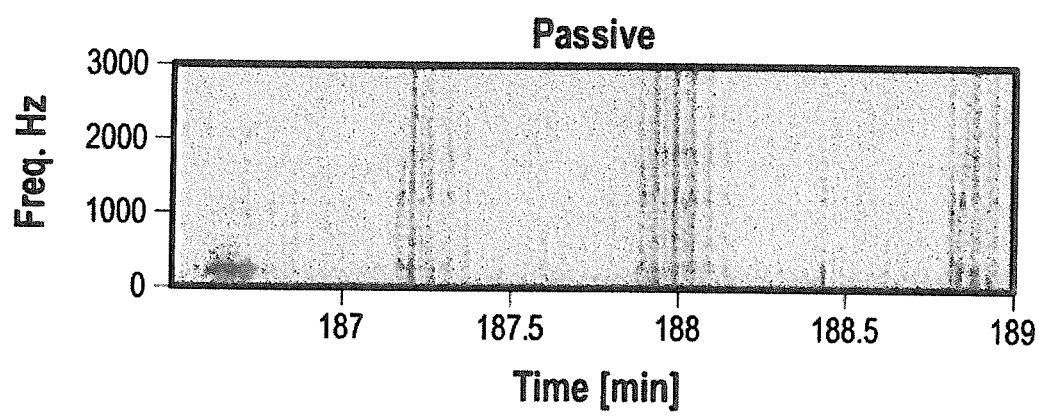
Figure 24:
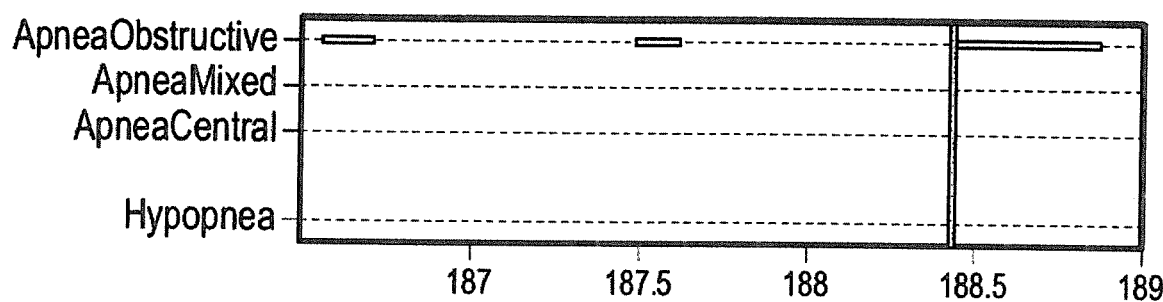
Figure 25:
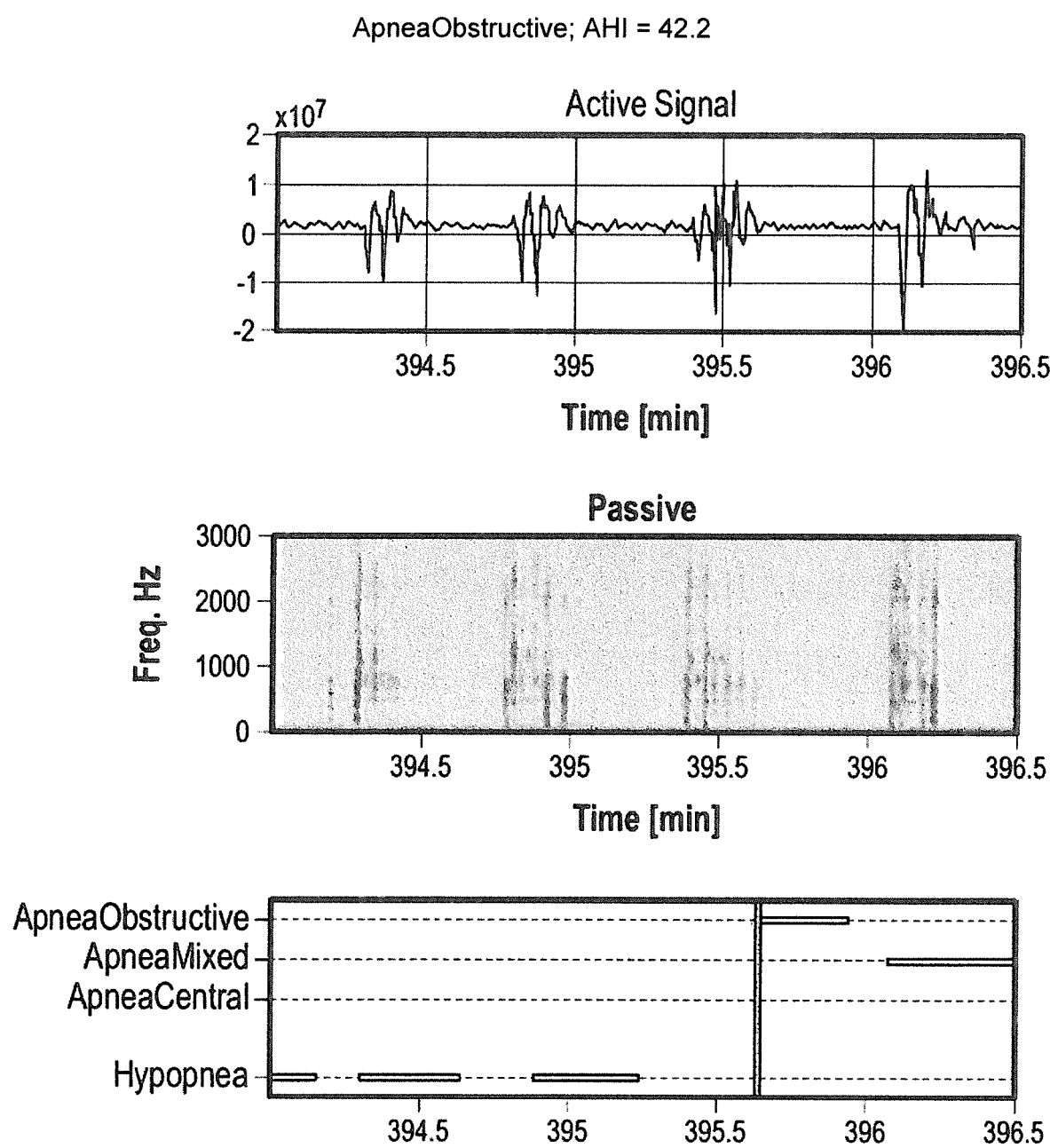
Figure 26:
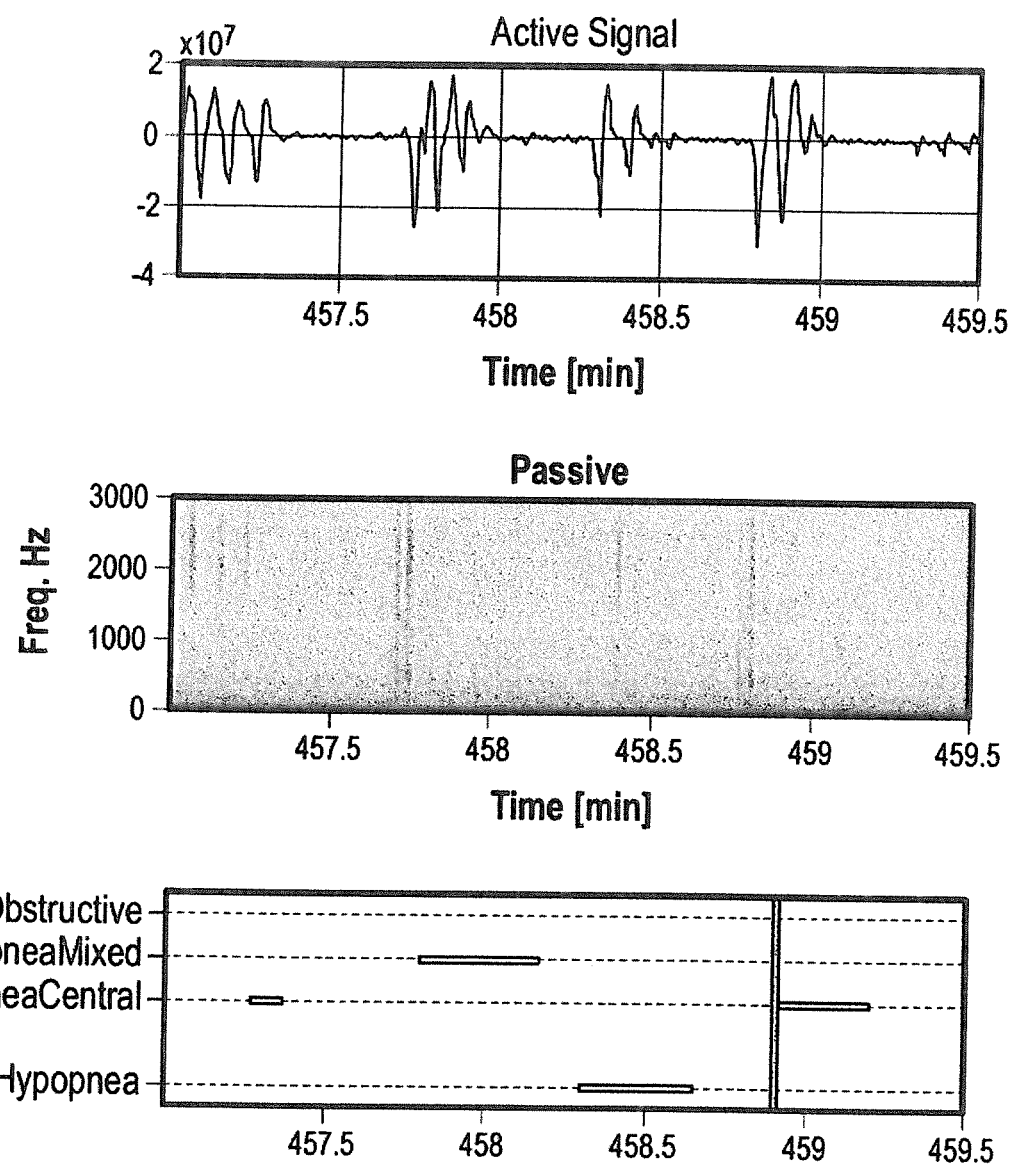
Figure 27:
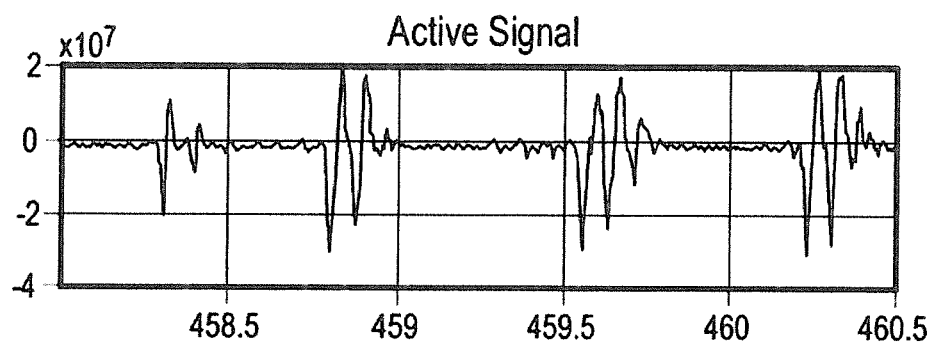
Figure 27:
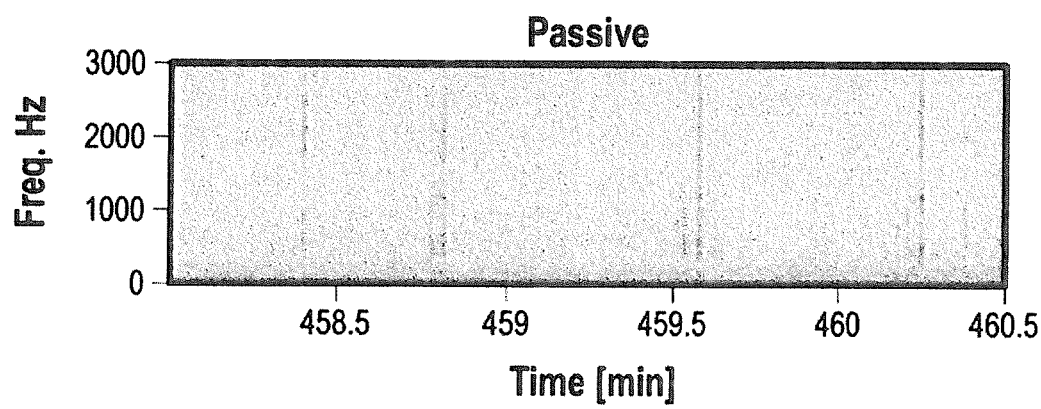
Figure 27:
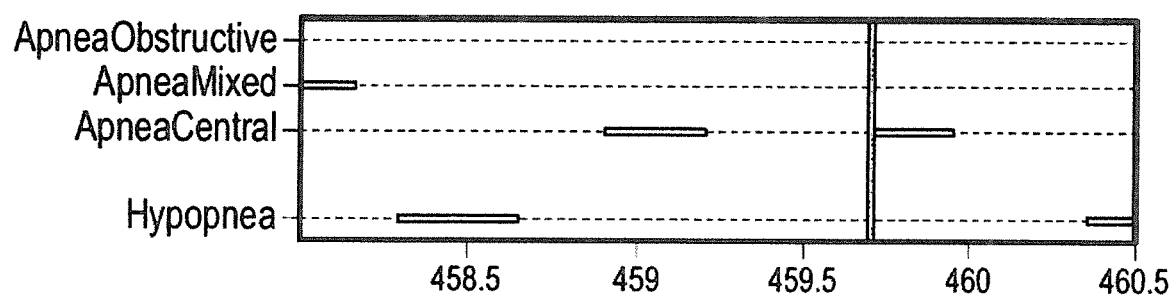
Figure 28:
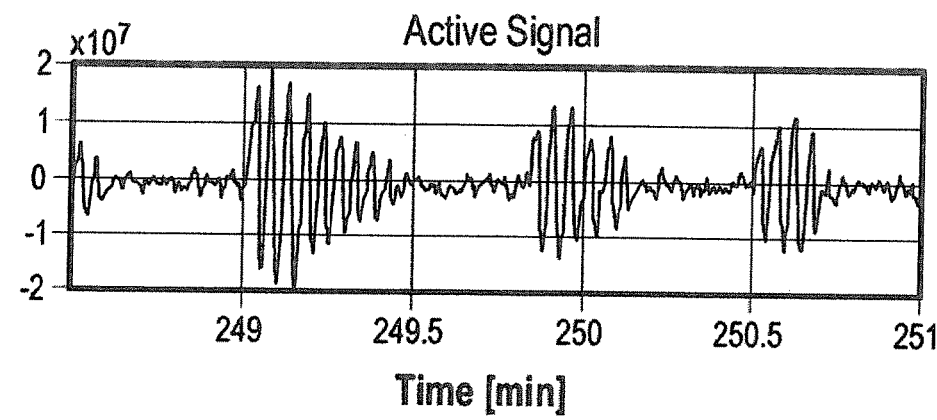
Figure 28:
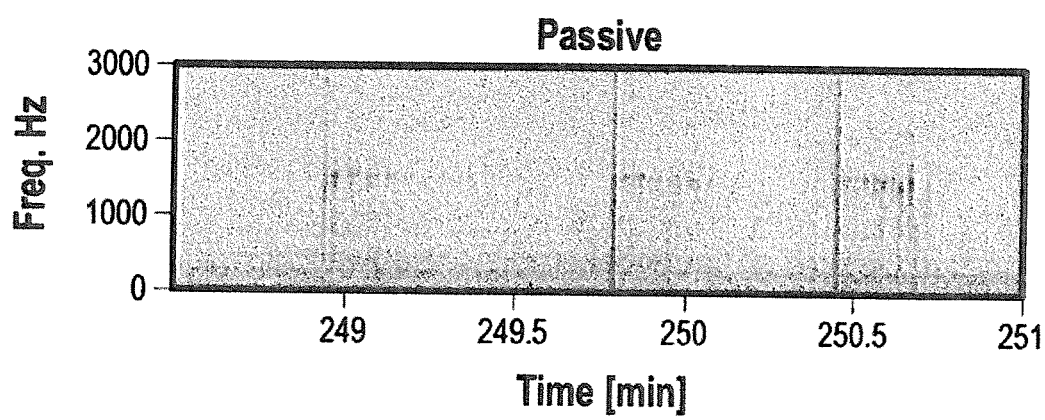
Figure 28:
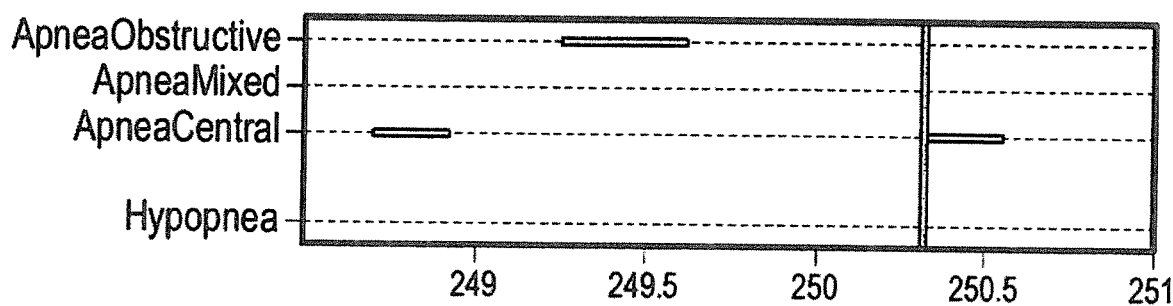
Figure 29:
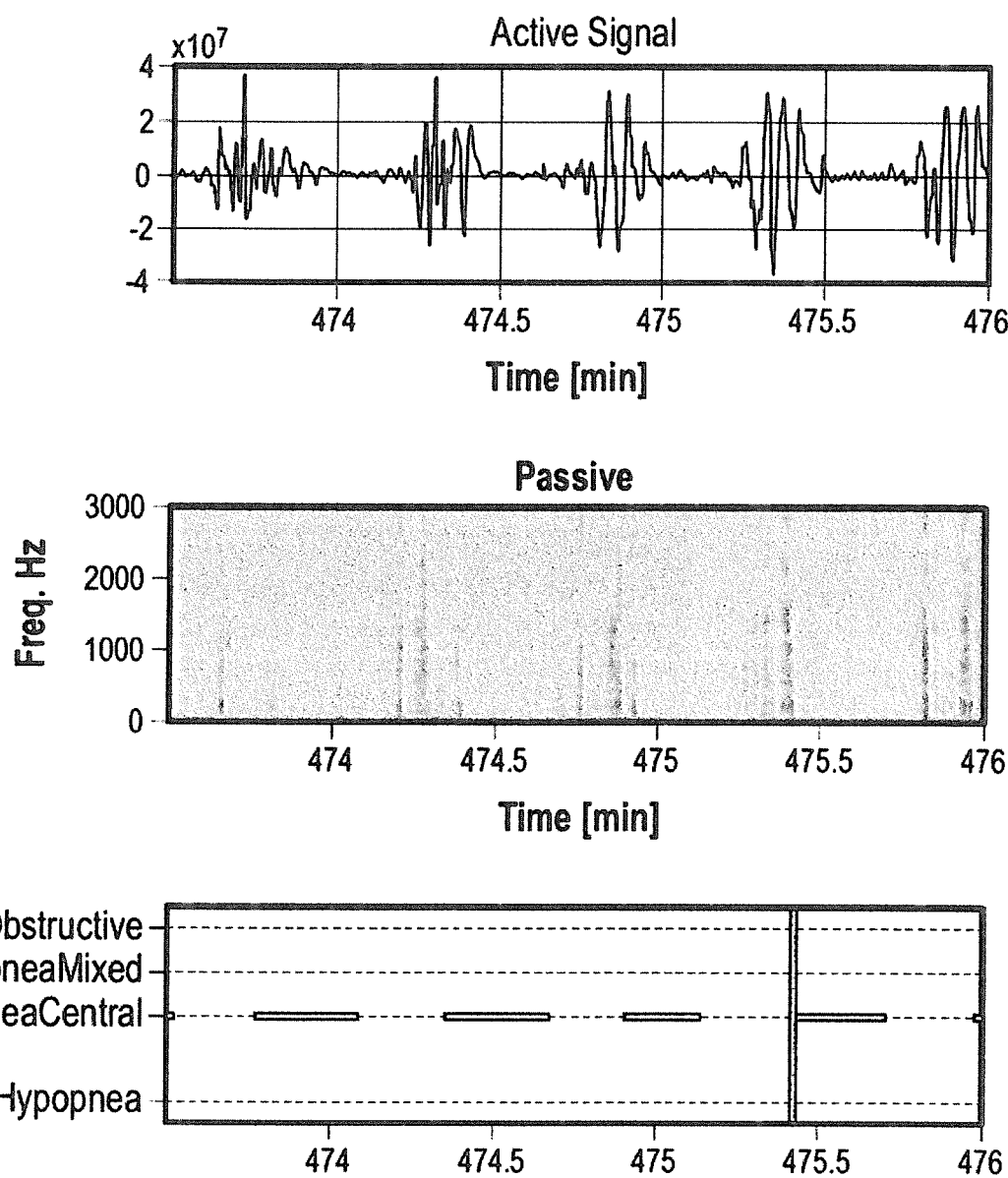
Figure 30:
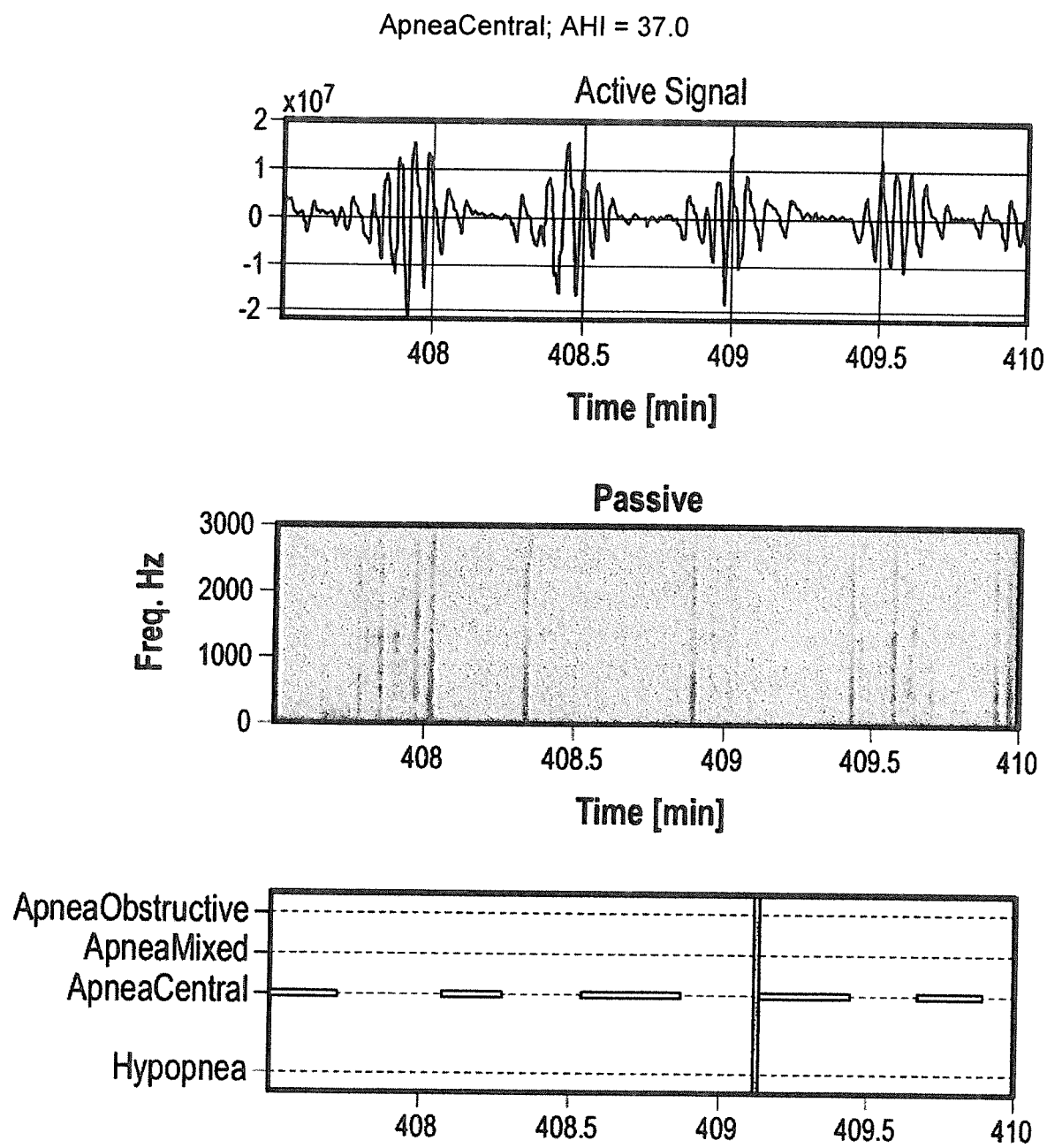

FIG. 17 illustrates a graphic SDB risk identifier that may be generated in some versions of the present technology, illustrating a risky sleeper assessment of SDB risk when sufficient data or sensing signals are not detected.

FIGS. 18 to 32 illustrate graphic displays generated with signals of the active and passive sensing techniques described herein on a common time scale with an automated demarcation graphic display of example respiratory events (SDB) that are detectable with the methodologies described herein.

Figure 33:
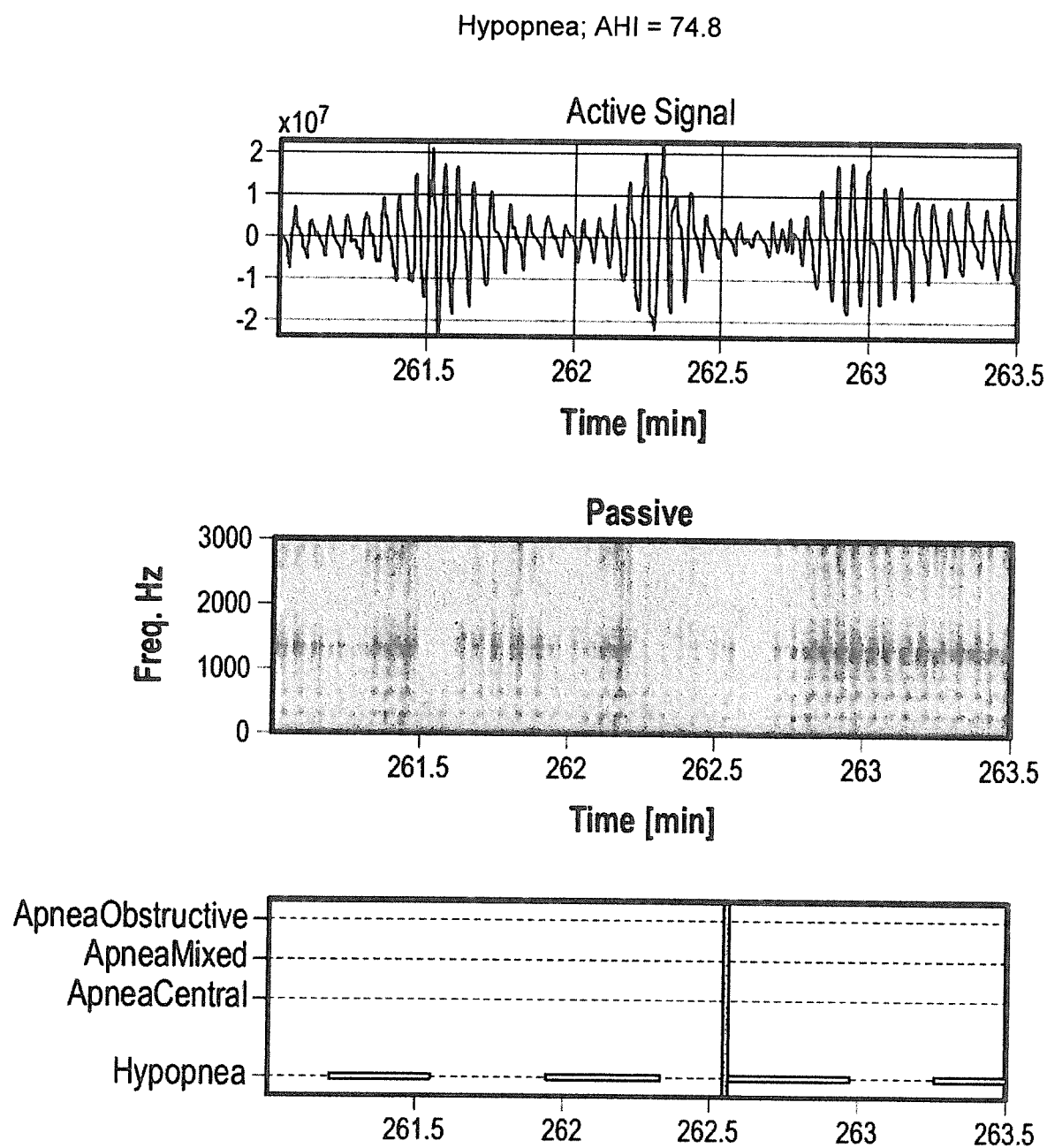

FIG. 33 shows an example user interface for a display of apparatus described herein, with output SDB risk, snoring and sleep quality indicators, derived with signals of the active and/or passive sensing techniques described herein.

Figure 34:
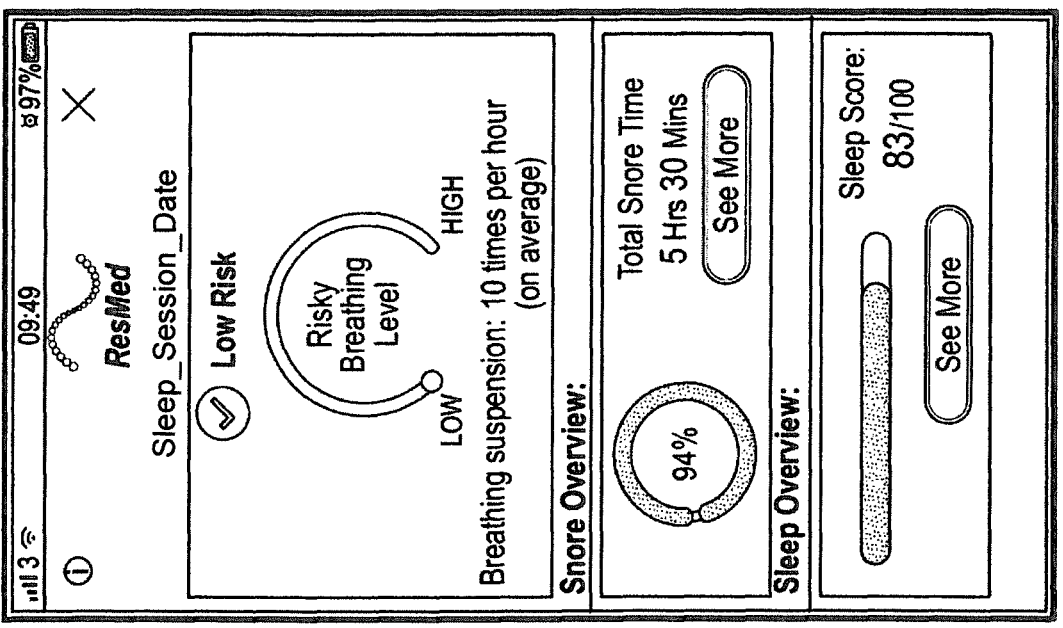

FIG. 34 shows an example user interface for a display of apparatus described herein similar to FIG. 33 with an output SDB risk (risky sleeping), snoring and sleep quality indicators, derived with signals of the active and/or passive sensing techniques described herein.

Figure 35:
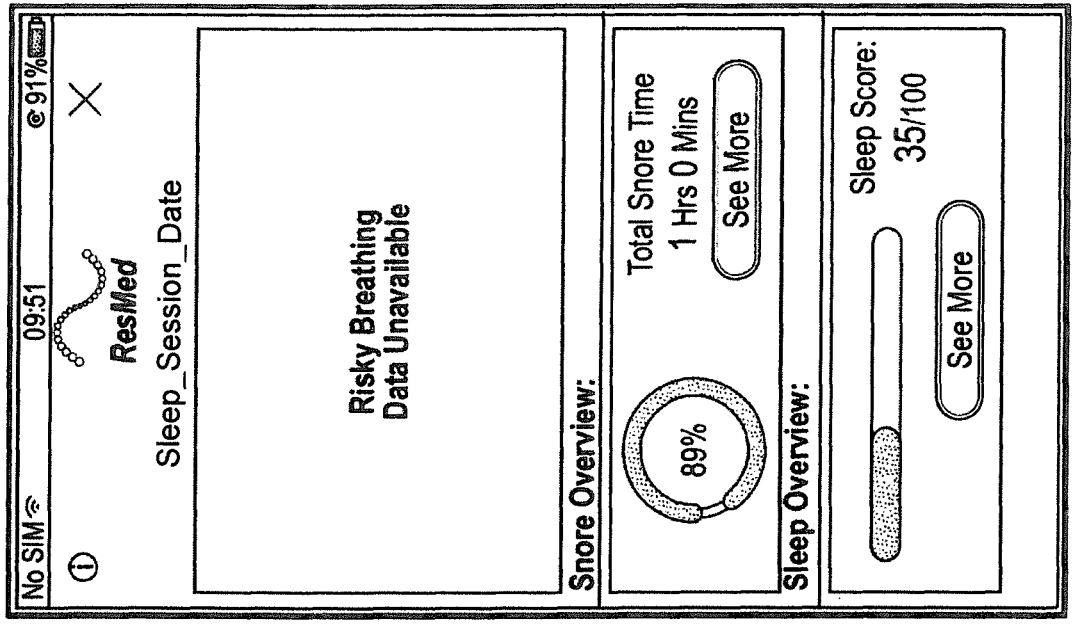

FIG. 35 shows an example user interface for a display of apparatus described herein, with output of a snoring analysis, derived with signals of the active and/or passive sensing techniques described herein.

Figure 36:
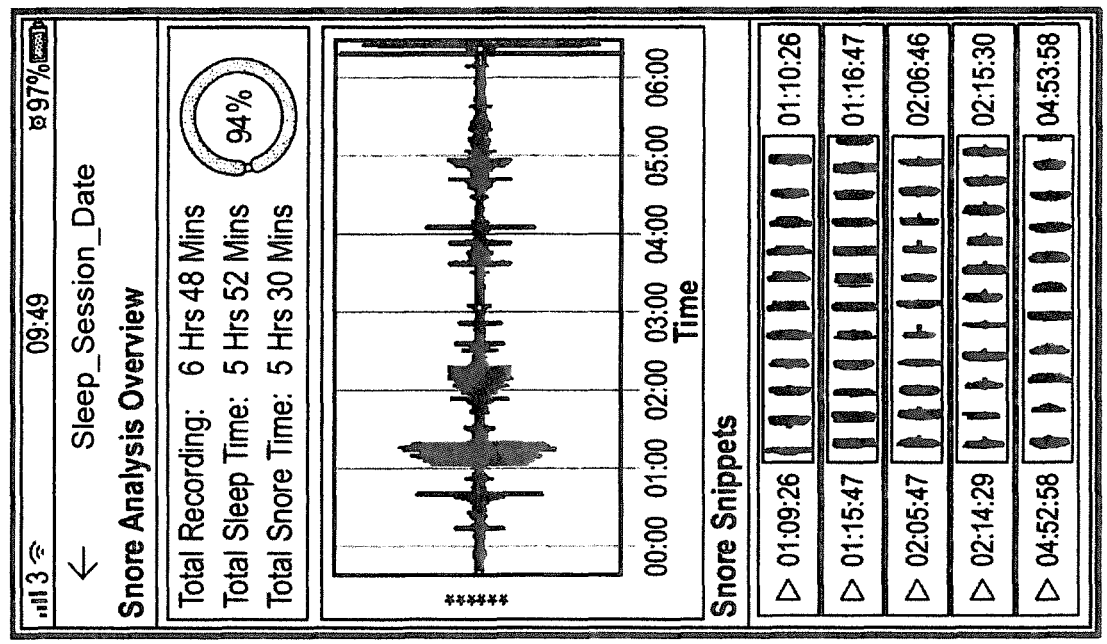

FIG. 36 shows an example user interface for a display of apparatus described herein, with output of a sleep analysis, including a hypnogram and sleep session summary, derived with signals of the active and/or passive sensing techniques described herein.

Figure 37:
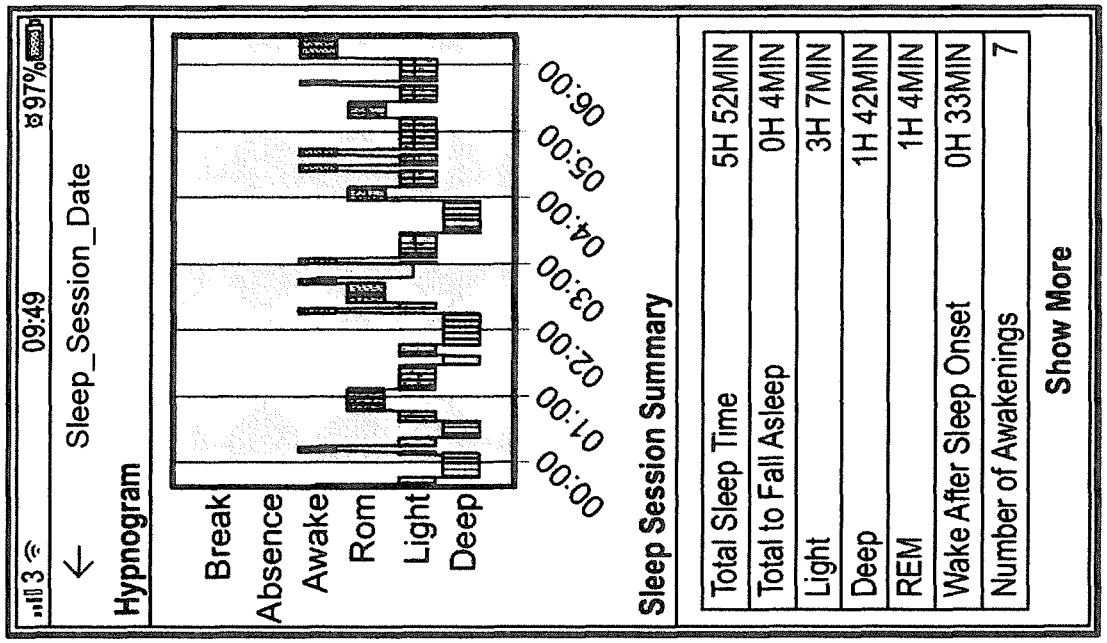

FIG. 37 shows an example user interface for a display of apparatus described herein, with output of a sleep analysis and breathing rate display on a common time scale, derived with signals of the active and/or passive sensing techniques described herein.

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The apparatus and methods described below are particularly suitable for the monitoring such as for screening of coughing and/or sleep disordered breathing, and are described in those terms. However, the described apparatus and methods may also be applied to monitoring other events that affect a patient's respiration.

The methodologies described herein may implement SDB risk detection and/or cough detection with passive sensing technologies (sound monitoring) and/or one or more active sensing technologies (e.g., radar and/or sonar sensing) and may be implemented by one or more processors such as by any of the apparatus described in this specification. For example, the methodologies described in this specification can be executed by one or more processors such as (i) with an application on a processing or computing device, such as a mobile phone (e.g., smartphone), smart speaker, a smart TV, a smart watch or tablet computer, that may be configured with a speaker and microphone such that the processing of the application implements a synergistic fusion of passive sensing (acoustic breathing related sound monitoring) and active acoustic sensing (e.g., SONAR such as with ultrasonic sensing), (ii) on a dedicated hardware device implemented as a radio frequency (RF) sensor (e.g., RADAR) and a microphone, (iii) on a dedicated hardware device implemented as an RF sensor without audio; and/or (iv) on a dedicated hardware device implemented as an active acoustic sensing device without RF sensing. Other combinations of such devices will be recognized in relation to the details of the following disclosure. Thus, such devices may be independent or work cooperatively to implement the acoustic and radio frequency-based sensing with any of the detection/monitoring methodologies described herein.

For example, a device with one or more processors to implement the detections and/or displays described herein may be integrated with one or more of the active and/or passive sensing hardware in a housing of the device. Optionally, a processing device with one or more processors to implement the detections and/or displays described herein may be separately coupled to external active and/or passive sensing hardware, such as via wired and/or wireless communications, for the purposes of receiving information associated with the active and/or passive sensing. Such external sensor(s) may be for example, other sensing device(s) located in a room where sensing occurs (e.g., a bedroom) and may be separate from, for example, a processing device (e.g., an RPT device, a smart phone or another smart device) that implements the detections and/or displays described herein.

Moreover, the one or more processors configured to implement the detections and/or displays thereof may work independently or cooperatively such as via data communications (e.g., wired and/or wireless transmissions). For example, a processing device receiving the sensing signals may perform processing of the signals and detections therefrom as described herein either locally or remotely, or some combination of both. In one such example, a processing device (e.g., a smart phone) may be configured to perform the processing and detections (from received sensing signals) locally (i.e., on the processing device) and display the results. In another such example, a processing device (e.g., a smart phone) may be configured to perform some of the processing and/or detections (from received sensing signals) locally (i.e., on the processing device) and transmit data to remote processing device(s) (e.g., one or more servers) so that some of the processing and/or detections may be performed remotely. In some such cases, the remote processing device(s) may transmit the results back to the local processing device for display on the local processing device. In other cases, such as in the case where the local processing device is an RPT device with limited processing and/or display capabilities, the local processing device may transmit the data received from the remote device to another local device (such as a smart phone) for further processing and/or display.

In another example configuration, a processing device (e.g., a smart phone), may be configured to transmit data (e.g., sensing signals) to remote processing device(s) (e.g., one or more servers) so that the processing and detections may be performed remotely. In such a case, the remote processing device(s) may transmit the results back to the local processing device for display on the local processing device or on another device associated with it.

8.1 Treatment Systems

In one form, the present technology comprises an apparatus or device for treating a sleep disorder. The apparatus or device may comprise a respiratory pressure therapy (RPT) device 4000 for supplying pressurised air to the patient 1000 via an air circuit 4170 to a patient interface 3000.

8.1.1 Patient Interface

A non-invasive patient interface 3000 in accordance with one aspect of the present technology may comprise the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways. In some forms, the patient interface, such as for delivering a high flow therapy, may be provided without a significant seal forming structure.

8.1.2 RPT Device

An RPT device 4000, or respiratory therapy device, in accordance with one aspect of the present technology comprises mechanical, pneumatic, and/or electrical components and is configured to execute one or more algorithms. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O. Thus, such a device may be configured as a positive airway pressure device or a high flow therapy device.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202. With such a central controller 4230, such as with one or more processors, the RPT device may be a processing device as described in more detail herein, either when implemented with the acoustic and/or radio frequency sensing components described herein or when communicating with apparatus with such sensing components to receive one or more of such sensing signals.

8.1.3 Air Circuit

An air circuit 4170 in accordance with an aspect of the present technology is a conduit or a tube constructed and arranged to allow, in use, a flow of air to travel between two components such as RPT device 4000 and the patient interface 3000.

8.1.4 Humidifier

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

8.2 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume, Vt, 0.5 L, inspiratory time, Ti, 1.6 seconds, peak inspiratory flow rate, Qpeak, 0.4

L/s, expiratory time, Te, 2.4 seconds, peak expiratory flow rate, Qpeak, −0.5 L/s. The total duration of the breath, Ttot, is about 4 seconds. The person typically breathes at a rate of about 15 breaths per minute (BPM), with Ventilation, Vent, about 7.5 L/min. A typical duty cycle, the ratio of Ti to Ttot, is about 40%.

FIG. 6B shows selected polysomnography channels (pulse oximetry, flow rate, thoracic movement, and abdominal movement) of a patient during non-REM sleep breathing normally over a period of about ninety seconds, with about 34 breaths. The top channel shows blood oxygen saturation ($SpO_2$), the scale has a range of saturation from 90 to 99% in the vertical direction. The patient maintained a saturation of about 95% throughout the period shown. The second channel shows quantitative respiratory flow rate, and the scale ranges from −1 to +1 LPS in a vertical direction, and with inspiration positive. Thoracic and abdominal movement are shown in the third and fourth channels.

8.3 Diagnostice, Monitoring and/or Screening Systems

8.3.1 Polysomnography

FIG. 7A shows a patient 1000 undergoing polysomnography (PSG). A PSG system comprises a headbox 2000 which receives and records signals from the following sensors: an EOG electrode 2015; an EEG electrode 2020; an ECG electrode 2025; a submental EMG electrode 2030; a snore sensor 2035; a respiratory inductance plethysmogram (respiratory effort sensor) 2040 on a chest band; a respiratory inductance plethysmogram (respiratory effort sensor) 2045 on an abdominal band; an oro-nasal cannula 2050 with oral thermistor; a photoplethysmograph (pulse oximeter) 2055; and a body position sensor 2060. The electrical signals are referred to a ground electrode (ISOG) 2010 positioned in the centre of the forehead.

Despite the quality and reliability of PSG systems, they are not well suited for long-term continuous monitoring and impose limited mobility, causing irritations, distress and discomfort to the patient under monitoring. These limitations have led to stronger demands for improved sleep monitoring systems.

8.3.2 Unobtrusive Monitoring Apparatus

The present technology particularly concerns systems, methods, and apparatus for detecting movement of a subject, including, for example, breathing movement and/or cardiac related chest movement, such as while the subject is asleep. Based on such breathing and/or other movement detection, the subject's sleep state and sleep disordered breathing events (e.g., apnea, hypopnea etc.) may be detected. For example, a processing device, such as an application (e.g., software for one or more processors) associated with a processing device (e.g., a general computing device, a smartphone, tablet, smart speaker, a smart TV, a smart watch etc.) may use the mobile device sensors, such as a speaker and microphone and/or a radio frequency transmitter/receiver, to passively detect such audible sounds and/or actively detect motion such as in a non-contact fashion. When combined such passive and active non-contact sensing techniques may complement each other and have a synergistic benefit in providing an improved sleep disordered breathing classification even where individually such methodologies may be confounded or incomplete. Such sensing signal information may be processed for the screening methodologies described herein in a non-contact fashion where sensors may monitor the user from a distance without a sensing modality that contacts the subject user either directly or indirectly. A general computing device, as understood herein, may be any electronic device that has a processor and has access to a speaker and a microphone such as for achieving any of the processing methodologies described herein.

A. Acoustic Non-Contact Sensing Apparatus

Example apparatus for implementation as a system suitable for the present technology is now described with reference to FIGS. 7B-1, 7B-2 and 7B-3. A mobile phone such as processing device 7100, or electronic device, configured with an application 7200 for detecting movement of subject 1000, may be placed on a bedside table near a person or subject (e.g., patient 1000). Mobile phone or processing device 7100 may be, for example, a smartphone or tablet having one or more processors. The processor(s) may be configured to, among other things, execute the functions of application 7200. Thus, in process 7202, such function may include (a) passive sensing such as by causing an audio signal to be generated that senses audible ambient sound in the environment of the device with a sound transducer such as a microphone, and/or (b) active sensing such as by causing generating and transmitting acoustic sensing signals with a speaker in a manner akin to SONAR, typically through the air as a generally open or unrestricted medium such as in a room vicinity of the device, receiving a reflection of the transmitted signal by sensing it with, for example, the transducer such as a microphone, and processing the sensed signal to determine body movement as one or more motion signal(s). In this context, the term SONAR may be understood to concern an active acoustic sensing, such as by generating/transmitting ultrasound or low frequency ultrasound sensing signals (e.g., in a frequency range of about 17-23 kHz, 18-22 kHz, or 17-18 kHz, for example), through the air. Such a system may be considered in relation to PCT/EP201 7/073613, the disclosure of which is incorporated herein by reference.

Thus, processing device 7100 may comprise, among other components, a speaker and a microphone. The speaker may be activated to transmit the sensing audio signal and the microphone to receive the reflected signal or ambient sound (e.g., user breathing sounds).

Thus, according to some aspects of the present technology, an audio signal may be generated and transmitted towards a user such as using one or more tones. A tone provides pressure variation in a medium (e.g., air) at a particular frequency. For purposes of this description, the generated tones (or audio signals or sound signals) may be referred to as "sound", "acoustic" or "audio" because they may be generated in a like manner to audible pressure waves (e.g., by a speaker). However, such pressure variations and tone(s) should be understood herein to be either audible or inaudible, notwithstanding their characterization by any of the terms "sound", "acoustic" or "audio." Thus, the audio signal generated may be audible or inaudible, wherein the frequency threshold of audibility across the human population varies by age. The typical "audio frequency" standard range is around 20 Hz to 20,000 Hz (20 kHz). The threshold of higher frequency hearing tends to reduce with age, with middle aged people often unable to hear sounds with frequencies above 15-17 kHz, whereas a teenager may be able to hear 18 kHz. The most important frequencies for speech are approximately in the range 250-6,000 Hz. Speaker and microphone signal responses for typical consumer smartphones are designed to roll off above 19-20 kHz in many cases, with some extending to above 23 kHz and higher (especially where the device supports a sampling rate of greater than 48 kHz such as 96 kHz). Therefore, for most people, it is possible to use signals in the range of 17/18 to 24 kHz and remain inaudible. For younger people that can hear 18 kHz but not 19 kHz, a band of 19 kHz to say 21 kHz could be employed. It is noted that some household pets may be able to hear higher frequencies (e.g., dogs up to 60 kHz and cats up to 79 kHz). The techniques that in this description have been referred to as "active" and "passive" sensing, often correspond to specific frequency ranges. For example, the "active" SONAR sensing is intended to be silent. For that reason, the "active" sensing tends to focus on frequencies that are difficult or impossible to hear, which are the frequencies at around and above 18 kHz. The "passive" sensing, on the other hand, targets the audible sounds made by a sleeping person and is hence usually focused on the frequency range below 18 kHz, such as 15 Hz-17 kHz or even 250 Hz-6,000 Hz.

The audio signal to be transmitted for active sensing (e.g., SONAR) may comprise, for example, sinusoidal waveforms, sawtooth chirps, triangular chirps, etc. As background, the term "chirp", as used herein, is a short-term non-stationary signal that could, for example, have a sawtooth or triangular shape, with a linear or non-linear profile. Several types of signal processing methods may be used to produce and sense the audio signal including, for example, continuous wave (CW) homodyning, pulsed CW homodyning, frequency modulated CW (FMCW), frequency hopping range gating (FHRG), adaptive FHRG (AFHRG), ultra wideband (UWB), orthogonal frequency division multiplexing (OFDM), adaptive CW, frequency shift keying (FSK), phase shift keying (PSK), binary phase shift keying (BSPK), quadrature phase shift keying (QPSK), and the generalized QPSK called quadrature amplitude modulation (QAM) etc.

Other motion signal(s) produced by a sonar type non-contact sensing apparatus may be utilized such as with the example of such a device described in International PCT Patent Publication No. WO2018/050913 (PCT/EP2017/073613), filed on 19 Sep. 2017, entitled APPARATUS, SYSTEM, AND METHOD FOR DETECTING PHYSIOLOGICAL MOVEMENT FROM AUDIO AND MULTIMODAL SIGNALS, the entire content of which is incorporated herein by reference. For example, such SONAR sensing may implement substantially contemporaneous, in parallel sensing of multiple ranges from the sensor to produce multiple motion signals having motions at different ranges from the sensor, such as by generating FMCW sensing signals.

Generally, and as described in more detail herein, the application 7200 may then process the detected signals such as to determine/extract pertinent information (e.g., motion) at process 7204 from the active sensing signals and/or sound breathing characteristics from the passive sensing signals. From such processing, sleep related information may be characterized (e.g., apnea and/or hypopneas identified and sleep disordered breathing quantified) at process 7206 by assessing the extracted information. One or more identifiers may then be generated and output at process 7208.

Other processes for or of such a device may include those described in U.S. Provisional Patent Application Nos. 62/610,033, 62/610,013, and 62/609,998, each filed on Dec. 22, 2017, the disclosures of which are incorporated herein by cross reference.

Figure 3:
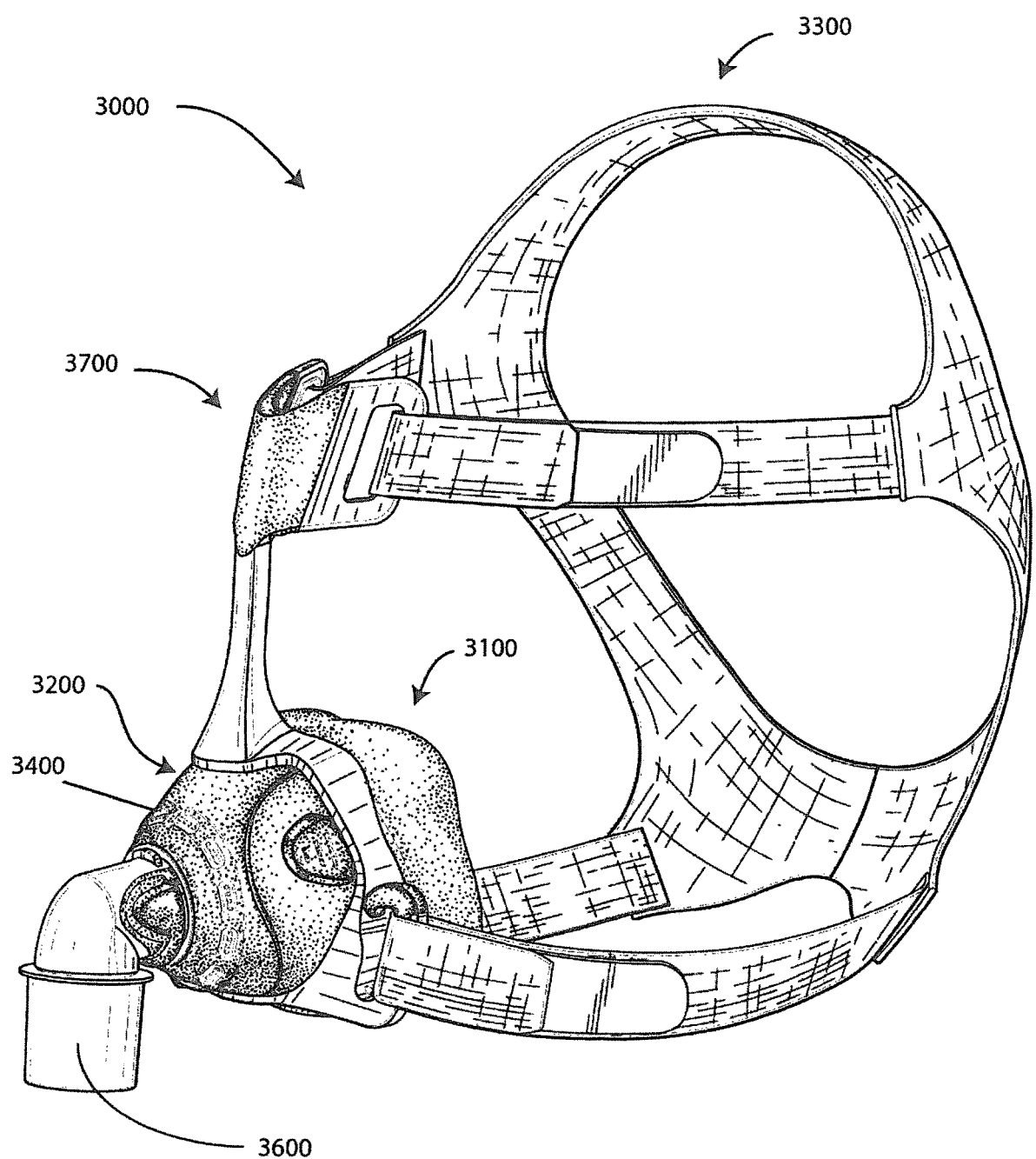
Figure 4A:
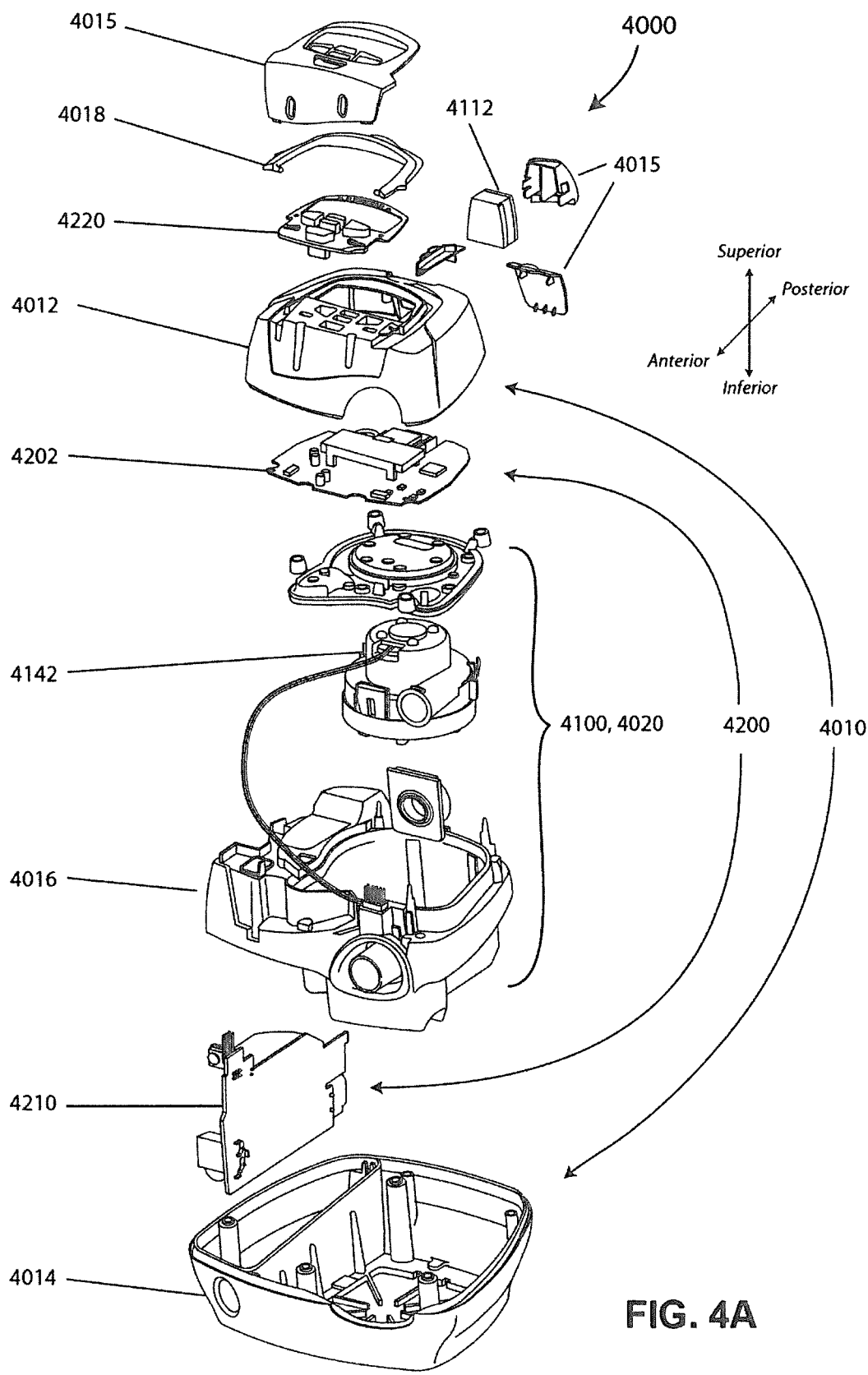
FIG. 4A shows an RPT device in accordance with one form of the present technology.
Figure 4B:
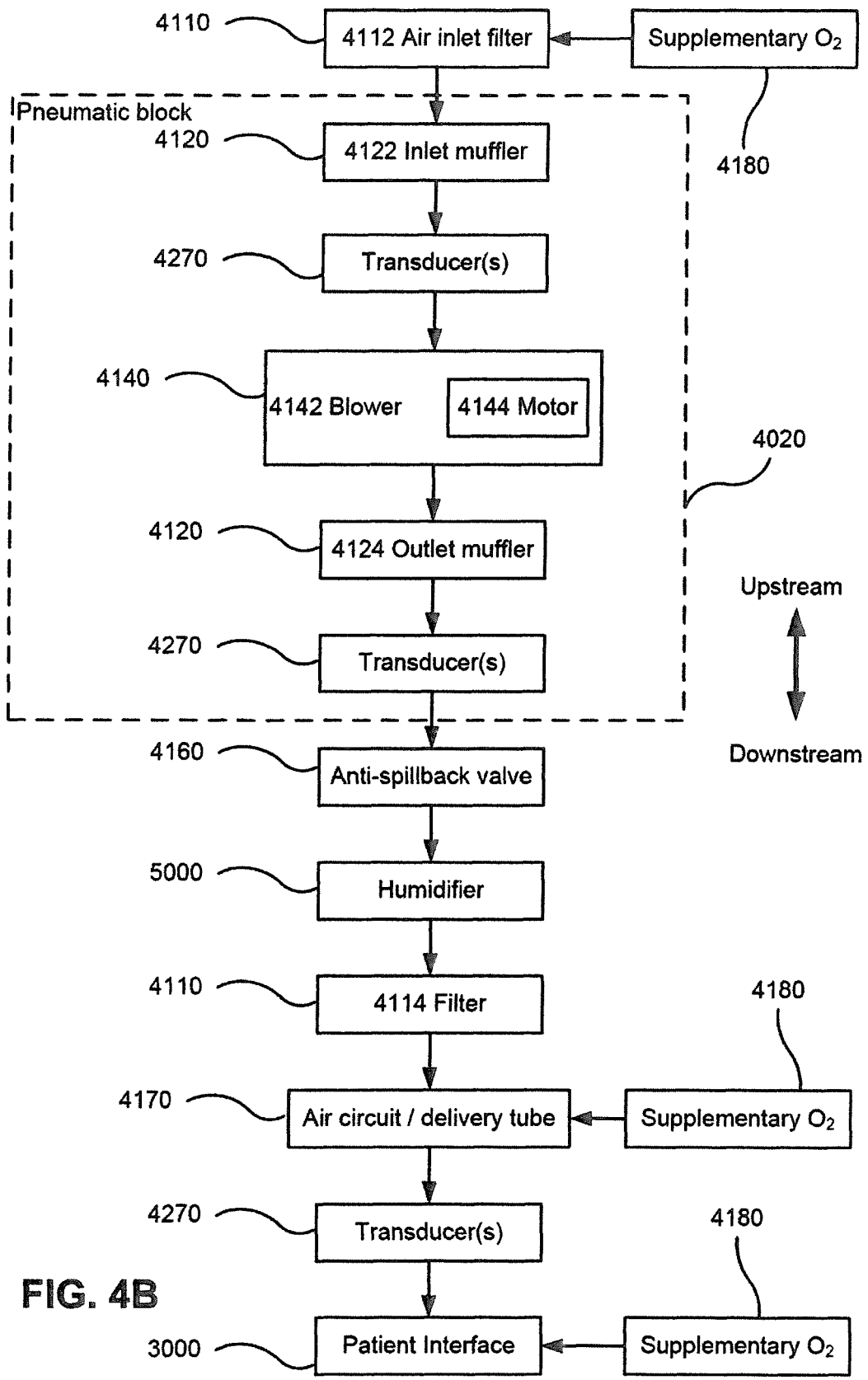
FIG. 4B shows a schematic diagram of the pneumatic path of the RPT device of FIG. 4A in accordance with one form of the present technology. The directions of upstream and downstream are indicated.

As illustrated in FIG. 7B-3, such a processing device 7100 may include integrated chips, a memory and/or other control instruction, data or information storage medium. For example, programmed instructions encompassing the assessment/signal processing methodologies described herein may be coded on integrated chips in the memory of the device or apparatus to form an application specific integrated chip (ASIC). Such instructions may also or alternatively be loaded as software or firmware using an appropriate data storage medium. Optionally, such processing instructions may be downloaded such as from a server over a network (e.g. an internet) to the mobile device such that when the instructions are executed, the processing device serves as a screening or monitoring device.

Accordingly, processing device 7100 may include a number of components as illustrated by FIG. 7B-3. The processing device 7100 may optionally include any of, among other components, a microphone or sound sensor 7302, a processor 7304, a display interface 7306, a user control/input interface 7308, a speaker 7310, and a memory/data storage 7312, such as with the processing instructions of the processing methodologies/modules described herein. Although not shown, such as processing device may also include a communications interface such as for receiving or sending information such as sensor data from external sensors.

One or more of the components of processing device 7100 may be integral with or operably coupled with processing device 7100. For example, microphone or sound sensor 7302 may be integral with processing device 7100 or coupled with processing device 7100 such as through a wired or wireless link (e.g., Bluetooth, Wi-Fi or other communications interface etc.). For example, a radio frequency sensing apparatus as described herein may be coupled with the processing device 7100 to provide sensing signals to the processing device from the radio frequency sensing apparatus (or vice versa) for processing as described herein.

Memory/data storage 312 may comprise a plurality of processor control instructions for controlling processors 304 of the processing device. For example, memory/data storage 312 may comprise processor control instructions for causing application 200 to be performed by the processing instructions of the processing methodologies/modules described herein. Optionally, such processor control instructions (code) may be loaded as software or firmware using an appropriate data storage medium or processor-readable medium. Optionally, such processing instructions may be downloaded such as from a server over a network (e.g. an internet or the Internet) to the processing device or portable computing device such that when the instructions are executed, the device serves as a screening, diagnosing, and/or monitoring device. Thus, the server may be configured to transmit the processor control instructions (code) to the processing device, such as over a network, in response to requests from the processing device. Such a server may be configured to receive requests for downloading the processor-executable instructions from a processor-readable medium of the server to a processor-readable medium(s) of one or more processing device(s) over the network.

B. Radio Frequency Non-Contact Sensing Apparatus

Additional sensing apparatus may be considered in reference to FIG. 7C-1 illustrates an unobtrusive monitoring apparatus 7000 according to one form of the present technology. The monitoring apparatus 7000 is positioned adjacent and relatively close to the sleeping patient 1000 (e.g. on a bedside table) and may optionally communicate with a processing device as previously described or be integrated with such a processing device.

FIG. 7C-2 is a block diagram illustrating the components of the monitoring apparatus 7000 of FIG. 7C-1 in more detail, according to one form of the present technology. In the monitoring apparatus 7000, a contactless sensor unit 1200 includes a contactless motion sensor 7010 generally directed toward the patient 1000. The motion sensor 7010 is configured to generate one or more signals representing bodily movement of the patient 1000, from which may be derived one or more respiratory movement signals representing respiratory movement of the patient.

The sensor unit 1200 may also include a microcontroller unit (MCU) 7001, and a memory 7002 (e.g. a memory card) for logging data. In one implementation, the sensor unit 1200 may include communications circuitry 7004 configured to transfer data to an external computing device 7005, e.g. a local general purpose computer such as processing device 7100, or a remote server, via a connection 7008. The connection 7008 may be wired or wireless, in which case the communications circuitry 7004 has wireless capability, and may be direct or indirect via a local network or a wide-area network (not shown) such as the Internet.

The sensor unit 1200 includes a processor 7006 configured to process the signals generated by the motion sensor 7010 as described in detail below.

The sensor unit 1200 may optionally include a display device 7015 configured to provide visual feedback to a user. In one implementation, the display device 7015 comprises one or more warning lights (e.g., one or more light emitting diodes). The display device 7015 may also be implemented as a display screen such as an LCD or a touch-sensitive display. Operation of the display device 7015 is controlled by the processor 7006 based on an assessment of the patient's sleep. The display device 7015 may be operated to show information to a user of the monitoring apparatus 7000, such as the patient 1000, or a physician or other clinician. The display device 7015 may also display a graphical user interface for operation of the monitoring apparatus 7000.

The sensor unit 1200 may also include an audio output 7017 configured to provide acoustic feedback to a user under the control of the processor 7006, e.g., a tone whose frequency varies with breathing, or an alarm which sounds when certain conditions are met. In some versions, the sensor unit 1200 may include a sound transducer such as a microphone for passive sensing as described in more detail herein.

User control of the operation of the monitoring apparatus 7000 may be based on operation of controls (not shown) that are sensed by the processor 7006 of the monitoring apparatus 7000.

It should be noted that, as indicated by the dotted line surrounding the motion sensor 7010, this sensor may be defined and located spatially separately from the remaining components of the sensor unit 1200. In such a configuration, the contactless motion sensor 7010 may be arranged to communicate wirelessly with the remaining units.

One example of a sensor unit 1200 is the S+ device manufactured by ResMed Sensor Technologies Ltd, which may contain a contactless Doppler radio-frequency (RF) motion sensor 7010. Such a sensor unit may be the sensor described in International PCT Patent Publication No. WO 2014/015238, filed on Jul. 13, 2013, the entire disclosure of which is incorporated herein by reference.

In one form of the present technology, such as when the S+ device is used, the sensor unit 1200 of the motion sensor 7010 includes an RF transmitter 7020 configured to transmit a signal 7060. In contrast to the above discussed acoustic non-contact sensing apparatus, the transmitted signal 7060 in this case is in the radio frequency (RF) range. The transmitted RF signal 7060 for example has the form $$s(t)=u(t)\cos(2\pi f_c t+\theta) \quad (Eq.\ 1)$$

In Eq. 1, the carrier frequency is $f_c$ (typically in the range 100 MHz to 100 GHz, e.g. 3 GHz to 12 GHz, e.g. 5.8 GHz or 10.5 GHz), t is time, θ is an arbitrary phase angle, and u(t) is a pulse shape. In a continuous wave system, the magnitude of u(t) may be unitary, and can be omitted from Eq. 1. More generally, the pulse u(t) may be defined as in Eq. 2:

$$u(t) = \begin{cases} 1, & t \in [kT, kT + T_p], k \in Z \\ 0, & \text{otherwise} \end{cases} \quad (Eq.\ 2)$$

where T is the period width, and $T_p$ is the pulse width. Where $T_p \ll T$, this becomes a pulsed continuous wave system. In one case, as $T_p$ becomes very small, the spectrum of the emitted signal becomes very wide, and the system is referred to as an ultra-wideband (UWB) radar or impulse radar. Alternatively, the carrier frequency of the RF transmitted signal 7060 can be varied (chirped) to produce a so-called frequency modulated continuous wave (FMCW) system.

The transmitted radio frequency signal 7060 may be generated by the RF transmitter 7020 using a local oscillator 7040 coupled with circuitry for applying the pulse gating. In the FMCW case, a voltage-controlled oscillator is used together with a voltage-frequency converter to produce the RF signal 7060 for transmission. The coupling of the transmitted RF signal 7060 to the air may be accomplished using an antenna 7050. The antenna 7050 can be omnidirectional (transmitting power more or less equally in all directions) or directional (transmitting power preferentially in certain directions). It may be advantageous to use a directional antenna 7050 so that transmitted and reflected energy enable sensing within a region. In one implementation of the monitoring apparatus 7000, a single antenna 7050 is used for both the RF transmitter 7020 and the receiver 7030, with a single carrier frequency. Alternatively, multiple receive and transmit antennas 7050 can be used, with multiple carrier frequencies.

The monitoring apparatus 7000 is compatible in various embodiments with various types of antenna 7050 such as simple dipole antennas, patch antennas, and helical antennas, and the choice of antenna can be influenced by factors such as the required directionality, size, shape, or cost. It should be noted that the monitoring apparatus 7000 can be operated in a manner which has been shown to be safe for human use. The monitoring apparatus 7000 has been demonstrated with a total system emitted average power of 1 mW (0 dBm) and lower. The recommended safety level for RF exposure is 1 mW/cm$^2$. At a distance of 1 meter from a system transmitting at 0 dBm, the equivalent power density will be at least 100 times less than this recommended limit.

In use, the transmitted RF signal 7060 is reflected off objects that reflect radio waves (such as the air-body interface of the patient 1000), and some of the reflected signal 7070 will be received at a receiver 7030, which can be collocated with the RF transmitter 7020, or which can be separate from the RF transmitter 7020, in a so-called "bistatic" configuration. The received signal 7070 and the transmitted RF signal 7060 can be multiplied together in a mixer 7080 (either in an analog or digital fashion). This mixer 7080 can be of the form of a multiplier (as denoted below in (Eq. 3)) or in a circuit which approximates the effect of a multiplier (e.g., an envelope detector circuit which adds sinusoidal waves). For example, in the CW case, the mixed signal will equal $$m(t) = \gamma \cos(2\pi f_c t)\cos(2\pi f_c t + \phi(t)) \quad \text{(Eq. 3)}$$

where $\phi(t)$ is a phase term resulting from the path difference of the transmitted and received RF signals 7060 and 7070 (in the case where the reflection is dominated by a single reflective object), and $\gamma$ is the attenuation experienced by the reflected signal 7070. If the reflecting object is fixed, then $\phi(t)$ is fixed. In the monitoring apparatus 7000, the reflecting object (e.g., the chest of the patient 1000) is in general moving, and $\phi(t)$ will be time-varying. As a simple example, if the chest is undergoing a sinusoidal motion of frequency $f_m$ due to respiration, then the mixed signal m(t) contains a component at $f_m$ (as well as a component centred at $2f_c$ which can be simply removed by low pass filtering). The signal at the output of the low pass filter after mixing is referred to as the movement signal or the demodulated sensor movement signal 7003, and contains information about gross bodily (non-respiratory) movement, and respiratory movement. Examples such methodologies may be considered in reference to U.S. Patent Application Publication No. US 2014-0163343, published on Jun. 12, 2014, the entire disclosure of which is incorporated herein by reference.

The amplitude of the demodulated sensor movement signal 7003 is affected by the mean path distance of the reflected signal, leading to detection nulls and peaks in the motion sensor 7010 (i.e. areas where the motion sensor 7010 is less or more sensitive). This effect can be minimised by using quadrature techniques in which the RF transmitter 7020 simultaneously transmits a signal 90 degrees out of phase (in quadrature) with the transmitted RF signal 7060 of Eq. 1. This results in two reflected signals, both of which can be mixed and lowpass filtered by the mixer 7080, leading to two demodulated sensor signals, referred to as the "I signal" and the "Q signal" in respective I- and Q-"channels". The movement signal 7003 may comprise one or both of these signals. Such a methodology may be considered in reference to U.S. Patent Application Publication No. US 2014-0163343, published on Jun. 12, 2014.

In the UWB implementation, an alternative method of acquiring a movement signal 7003 may be used. The path distance to the most significant air-body interface can be determined by measuring the delay between the transmitted pulse and peak reflected signal. For example, if the pulse width is 1 ns, and the distance from the motion sensor 7010 to the body is 0.5 metres, then the delay before a peak reflection of the pulse arrives at the receiver 7030 will be $1/(3\times10^8)$ s=3.33 ns. By transmitting large numbers of pulses (e.g., a 1 ns pulse every 1 μs) and assuming that the path distance is changing slowly over a given period, a movement signal 7003 may be computed as the average of the time delays over that period.

In this way, the motion sensor 7010, e.g., a radio-frequency sensor, can estimate the respiratory movement of the chest wall, or more generally the movement of the part of the body of the patient 1000 whom the monitoring apparatus 7000 is monitoring.

As mentioned above, the received signal 7070 can include large motion artefacts, e.g. as the result of gross bodily movement. This is due to the fact that the reflected signals from the body can contain more than one reflection path, and lead to complex signals (for example, if one hand is moving towards the sensor, and the chest is moving away, or if the chest is a part of two independent movements—a cyclical (respiratory) type of movement may be superimposed on a general movement of the entire body, i.e. when an adjustment of the user position in bed occurs). The reception of such signals is useful as it can indicate that the upper body is in motion, which is useful in determining sleep state.

In order to improve the quality of the respiratory movement signal, and more general bodily movement signals, the physical volume from which reflected energy is collected by the sensor unit 1200 can be restricted using various methods. For example, the sensor unit 1200 can be made "directionally selective" (that is, it transmits more energy in certain directions), as can the antenna of the receiver 7030. Directional selectivity can be achieved using directional antennas 7050, or multiple RF transmitters 7020. For example, in the case of multiple transmitters, each RF transmit array element may be considered in multiple groups, where each group forms a directional beam and modulates a distinct waveform, and all beams are steerable such as to point to the same direction. In alternative forms of the present technology, a continuous wave, an FMCW, or a UWB radar is used to obtain similar signals. A technique called "time-domain gating" can be used to only measure reflected signals 7070 which arise from signals at a certain physical distance from the sensor unit 1200. Frequency domain gating (filtering) can be used to ignore motions of the reflected object above a certain frequency. The method of implementing these technologies will be understood to those skilled in the technical art.

In implementations of the monitoring apparatus 7000 using multiple frequencies (e.g., at 500 MHz and 5 GHz), the lower frequency can be used to determine large motions accurately without phase ambiguity, which can then be subtracted from the higher-frequency sensor signals (which are more suited to measuring small motions). Such methodologies may be considered in reference to United States Patent Application Publication No. 2014-0350361, published on Nov. 27, 2914. Using such a sensor unit 1200, the monitoring apparatus 7000 collects information from the patient 1000, and uses that information to determine respiratory movement, and more general bodily movement information.

The movement signal 7003 may be stored in memory 7002 of the sensor unit 1200, and/or transmitted over a link (e.g., connection 7008) for cloud storage or for storage in the external computing device 7005, for each monitoring session. In one implementation, each monitoring session is one night in duration.

The processor 7006 of the sensor unit 1200, or that of the external computing device 7005, may process the stored movement signal(s) 7003 according to a monitoring process such as those described in detail below. The instructions for the described processes may be stored on a computer-readable storage medium, e.g. the memory 7002 of the sensor unit 1200, and interpreted and executed by a processor, e.g. the processor 7006 of the sensor unit 1200.

It will be appreciated that, apart from the single-box embodiment in FIG. 7C-2, the monitoring apparatus 7000 may also have a more distributed nature. Thus, the monitoring apparatus 7000 may include a number of RF sensors and/or smart speakers distributed at a plurality of locations, and linked to a central storage and/or processing unit. Such a distribution of sensors will allow an effortless and unobtrusive monitoring of a user in a number of predetermined locations.

8.3.3 Alternative Monitoring Apparatus

Yet other form(s) of the present technology as previously mentioned, may involve an RPT device 4000 or respiratory therapy device that is configured to supply respiratory therapy (e.g., a pressure therapy or high flow therapy) to the patient 1000 via an air circuit 4170 to a patient interface 3000, as illustrated in FIG. 1. In this case, the RPT device 4000 may also be configured as a monitoring apparatus such as when it is configured as a processing device described herein when it receives sensing related signals from discrete device(s) or integrated devices that have the passive and/or active sensing apparatus described herein. Thus, the sound-based sensing methodologies and/or radio frequency sensing methodologies may be implemented in or by other types of devices such as a bedside device (e.g., a respiratory therapy device such as a continuous positive airway pressure (e.g., "CPAP") device or high flow therapy device).

8.3.4 Monitoring, Screening and/or Diagnostic Process

In one aspect of the present technology, a monitoring apparatus carries out a monitoring process to monitor coughing and/or the patient's sleep for screening for SDB risk in relation to the respiration of the patient 1000 from active and/or passive sensing signals.

The system as described herein may rely on a non-contact alternative to PSG or PG (polygraphy) for detecting/screening/diagnosing sleep disordered breathing (SDB)—i.e., with no wires, electrodes, wearable devices or bed pads required to detect SDB. This is in contrast to traditional lab/hospital-based polysomnography (PSG) that requires many sensors to be adhered to or worn on the subject person's body. Significant problems with PSG are that it requires a lot of hardware that is uncomfortable, not readily available, expensive, and which negatively impacts your sleep (different sleeping environment, being instrumented). The PSG monitors many body functions, including brain activity (EEG), eye movements (EOG), muscle activity or skeletal muscle activation (EMG), and heart rhythm (ECG), during sleep as previously described.

By utilizing a non-contact sensor(s)/sensing, such as in a ubiquitous processing device (e.g., a general computing device, a smart phone, tablet computer, a smart speaker, a smart TV, a smart watch etc.) and/or in conjunction with such a device, a very efficient screening apparatus may be provided. In this regard, the processing device can be one that almost everybody owns already, which permits a relatively inexpensive, widely available, portable, computationally fast solution. With such a system, the SDB screening results can be almost instantaneous (i.e., upon completion of sleep session) and can in some versions provide an all-in-one solution that does not require specialist personnel, or separate tools to analyze. Such solutions can provide longitudinal monitoring and can allow integration of additional metrics and risk factors.

Overview of Some Advantages of Some Versions of the Technology:

In some versions of the present technology, the screening system may advantageously combine processes for both SDB risk assessment and sleep staging assessment so as to improve accuracy of either assessment. For example, in estimating an apnea/hypopnea count (AHI), accuracy may be improved with actual sleep parameters (e.g., permitting detection of apnea when the person is asleep (in a sleep stage), and/or to adjust the type of sleep in relation to someone with OSA). This may mitigate some problems with previous systems, where microarousals might cause a system to indicate an interval of wake, which could result in the potential of missing an SDB related event. For example, the event might be ignored by the system since the system determines that the person is awake, as opposed to asleep with micro arousal.

The system, such as in considering SDB intensity as described herein, can also account for both obstructive and central apneas in its assessment. In systems that merely provide snoring detection, such events of apnea or hypopnea are ignored. In contrast, the described technologically implemented approach can detect both because the system can measure/sense chest displacement (e.g., movement without contact sensing) to provide an indication of actual respiratory effort. Thus, if the monitored subject stops breathing (i.e., a central apnea—where the brain (respiratory control) is not sending signals to breathe), it is possible to detect this absence of respiratory motion. Conversely, with obstructive events (e.g., obstructive hypopnea or obstructive apnea—where a monitored subject is making (motion) efforts to breath against a partially or fully closed airway), the system can still "see" (detect or sense) the modulation. The effort can be detected in a passive audio analysis by sensing periods of noises followed by cessations of noise. This may also be considered in conjunction with active sensing of respiratory effort (motion) during such present and absent noises.

Thus, as described herein, the devices and methods may apply active sensing such as with any radio frequency sensing system or RADAR such as by using pulsed continuous wave (CW), continuous wave (CW), frequency modulated continuous wave (FMCW), ultra-wide band (UWB) sensing methodologies—where the system can detect modulation in respiration effort (user movement). Similar motion sensing may be accomplished with active sound sensing systems (SONAR). If a microphone is available as well, the sensing techniques may be implemented by a fusion of a passive acoustic sensing technique and at least one of the active sensing techniques.

Multi-Sensor Applicability:

For example, an SDB screening system of the present technology may implement multiple contactless sensing approaches—including active acoustic (e.g., low frequency ultrasonic—SONAR—whereby acoustic reflections are processed), passive acoustic ("listening" to audible breathing sounds using one or more microphones), and/or electromagnetic (e.g., radio frequency (RF) or RADAR—whereby radio frequency reflections are processed). Thus, in some versions, an acoustic version may be implemented with a combination of both active acoustic sensing (processing reflections using a speaker and microphone) with related signal analysis and passive acoustic sensing (listening) with related signal analysis. In some versions, the active sensing may be implemented by an RF system either (a) without passive acoustic analysis such as if a microphone is not available), or (b) with passive acoustic analysis in a fusion approach both where RF sensing and microphone sensing are implemented. When active sensing is employed, the sensing may be implemented in ranges (e.g., different motion sensing channels at different distances from the sensor) such by implementing pulsed CW, FMCW, and UWB.

Processing Across Range:

As discussed herein, the system may be implemented to evaluate motion signals across multiple sensing ranges (such that it may combine motion information in signals from multiple locations (distances) in a space of the sensing region or sensing vicinity). Such a combination may involve sensing techniques such as FMCW (frequency modulated continuous wave—either SONAR or RF) or other ranging techniques, to produce different motion channels/range bins for different detection distances. By evaluating motion information across ranges with such different range channels, an effort signal can be generated using a multi-range approach.

In an example of active processing, phase differences associated with a motion in different sensing ranges may be ignored such as by taking absolute value of different slices in space of the active 2D signal volume. Consider that a detection signal (channel) or range bin from a "30 cm" range may have similar motion information but may be out of phase with such a signal at "35 cm" range. By combining such channels (e.g., taking absolute values of different range bins before combining), it is possible to address the challenge that such signals may be out of phase. In summary, this is potential reason for using a rectified weighted sum over range bins to generate an active respiration effort signal.

As such, the system can be configured to calculate an envelope of a respiratory effort signal across multiple active channels (e.g., where each such active channel is derived from the FMCW signal corresponding to space). Similarly, the envelope of the effort signal may be derived with multiple channels from an acoustic passive sound analysis, where such channels from such passive sound analysis may correspond to different audio frequency bands. These different band channels are not strictly technically related to range in terms of distance. However, range/distance may have an association with such bands such that there may be changes in amplitude in the different bands due to distance.

Identifying Clusters of SDB Events (a Collection of Closely Grouped Events):

As discussed herein, the system may also be implemented to identify cluster(s) of apneic events rather than individually occurring events. For example, by using an in-band frequency metric ("IBM"), signal modulation strength can provide a signal quality (intensity of modulation) that can be evaluated to identify a cluster of such events. The frequency of such clusters can thus provide a basis for computation or assessment of SDB risk and be performed by an active sensing technique such as with SONAR acoustic sensing.

Intensity of modulation can be considered in relation to instability in the detected signals over a longer period when considering the impact of many apneas. For example, in contrast to considering merely a time period of a signal as one apnea, such modulation may be considered in relation to a time period where many apneas may occur. The intensity (which may be comparable to magnitude) of the modulation of the sensing signal where that intensity of modulation is attributable to many apneas, such as due to the severity of the apneas, provides a evaluation characteristic that considers many apneas at once. It can provide an insight into the stability (or not) of the body's physiological control systems.

An alternative realization may merely detect each apnea event, classify type of apnea, then count them on an individualized basis. Such an approach would not equate with the "intensity of modulation" approach.

The frequency of modulation of a determined respiratory effort envelope has also been discovered to have a subject-specific characteristic that can be predictive in estimating SDB level for a given subject. Thus, the metric can be implemented as a feature for SDB related risk classification by a classifier.

In relation to passive sensing and analysis (such as where the system records the breathing related sound of the person using a microphone), a passive envelope generation process can also be implemented for evaluation of modulation intensity. Such an approach is unusual in the field, because it does not process snore noise in a typical or standard manner. In considering modulation intensity of noise, whether it is breathing or snoring, the features of interest may be based on consideration of a change in baseline noise across frequencies (e.g., nine audio bands can be generated. The bands, by signal processing, may be processed to detrend the baseline (trend removal of artefacts). The resulting detrended signals may be averaged. Thus, changes in intensity may be evaluated. This approach (such as with trend reduction and averaging) is robust such that it may avoid the effect of shorter timescale background noises that may also be recorded by the microphone.

An envelope normalization step (which may be a combined mixer approach) may be used for both active and passive processing. Because each signal is "pulsy" (bursty in appearance) in nature, the system may initially integrate the signal and then high pass filter the result. Such "pulsy" or pulsatile signal types can benefit from pre-processing applied to the passive audio respiratory effort signals. For example, using passive audio, the system measuring the sound of a breath/snore can contain such signals that are pulsatile in nature as the system "hears" either the exhalation or inhalation sections of the user's breath.

Subsequently, the normalization step may then divide the resulting signal by a running standard deviation that is mixed in (i.e., added to a version of itself (which may be similar to a "fader knob" in sound processing). A motivation of envelope normalisation is to reduce the amplitude and hence reduce influence of large movement artefacts which may occur in a time window of the signal(s). This may lead to a visually 'cleaner' frequency domain for subsequent processing such that the target sleep disordered breathing event information may be more readily evaluated by the system.

The pre-processing step of integration and high-pass filtering (which may also be described as band-pass filtering) provides a transformation of a pulsatile signal into a shape more amenable for spectral analysis (such as to make it more sinusoidal in nature). This processing step may be, but is not required to be applied to the SONAR effort signals as the measured chest displacement does not typically exhibit the same pulsatile nature.

This may be considered a variable normalization approach, which may lead to better accuracy for a spectral analysis processing approach.

The system process may then apply the clusters that are identified by SONAR (and/or RF) to ensure that a sleep staging output (e.g., a hypnogram of different sleep stage times) is scored properly for sleep (not wake) such as for the case where SDB is discerned or measured, especially in the case of severe SDB. Thus, the spectral approach does not need to identify or detect individual incidents such as on an event-by-event basis. Rather, it can use a classifier based on overnight trends to characterize the modulation in relation to SDB generally from clusters of events.

Modulations of Respiratory Effort:

As described in more detail herein, the system may detect modulations of respiration effort in order to assess or detect presence of SDB, and to include obstructive events without central events. The system also enables detection of periodic movements associated with SDB recovery/arousals. This is useful when the breathing signal and/or the effort modulation is weak. With central events, this modulation goes to near zero and thus can may not be included/reflected within a modulation intensity signal described herein. With hypopnea, this is like an AM (amplitude) modulation. With obstructive events, a more severe AM modulation is detected.

To recap, the system can detect all forms of SDB events. As described in more detail herein, the system may detect modulations of respiration effort in order to assess or detect presence of SDB events, including hypopneas, obstructive, central and mixed events. All SDB events, will ultimately manifest as AM modulation in the respiratory effort signal envelope. The AM modulation strength is typically larger for obstructive events than for hypopneas. The system also enables detection of periodic movements associated with SDB recovery/arousals, which can be useful when the breathing signal and/or the effort modulation is weak. Thus, evaluation of the AM modulation such as with one or more thresholds by the system can permit it to distinguish or detect such events.

For example, the system is able to detect obstructive, hypopnea and central type events via the same processing of the respiration effort signal. All of these events can introduce a modulation in the effort signal although it may be different in nature. Obstructive events typically invoke an increase in effort (i.e. breathing against a restricted airway). Hypopneas are similar to obstructive events although with as the airway is only partially blocked the change in effort is smaller. Conversely a central event would manifest as a reduction in effort vs baseline (i.e., no attempt made to breathe). The types of events are verified against "gold standard" scoring performed in a PSG lab. Thus, the thresholds for evaluation of the AM modulation may be derived by system training. Moreover, it is possible to classify the event type by assessing whether an it has an associated increase or decrease in effort, (also shape of modulation and amplitude change) versus recent history baseline.

The steps to achieve this on active RADAR or SONAR (such as for the case of a demodulated 2D matrix representing range bins of an FMCW frontend system as described in International Patent Publication No. WO2018050913) include a process that combines signals from different range bins (within the defined sensing range) such as by employing a rectified weighted sum. As described in more detail herein, with such a combination of signals. The system may then, such over a timescale (e.g., about 25 second to about 100 seconds), search for or determine the strength (intensity) of modulation such as by using a spectrum of a moving window in order to calculate a spectral quality metric.

For a passive sensing stream processing such as where an analysis is carried out a signal received by a microphone (i.e., sound), different pre-processing steps may be carried out to estimate an envelope in relation to processing of active sensing signals. In this regard, different transformation(s) may be applied since the signals are different in constitution. The process may thereafter, integrate the signals (such as from envelopes of either active or passive processing streams) and then filter such as by high pass filtering.

A rationale for such a process for envelope detection on passive signals may be considered in relation to the following. Since there are typically sound related gaps between breaths (e.g., reduced sound), the system may be configured to identify peaks spaced around 5 secs apart, and interpolates the signal between these peaks to create the envelope. Subsequently, the envelope may be integrated and high pass filtered to handle the "pulsy" nature of the signals. This may be similar to a peak and hold approach, but may provide a more suitable performance. The peak search and interpolation process may provide an initial cleaning of the signals, but they may still be quite jagged in appearance (e.g., related impulse at end of event—relating to a recovery breath). Thus, additional steps of integration and high pass filtering can be applied to address such remaining jaggedness. An alternative approach could be to apply a band pass filter. However, the integration processing is useful because it can transform a pulse type morphology such that it the resulting signal is closer to being sinusoidal in appearance or constitution.

Both active and passive derived respiratory envelopes may then be normalized in a similar way. This can help prepare the signal for a high accuracy spectral analysis, which can provide a clear differentiation point in terms of performance. This can be an important step such as when the SONAR envelope scales are highly variable throughout the night (e.g., movements may cause a very large spike/artefact) and this normalization can help to compensate for such artefacts.

With respect to the active respiratory envelope(s), such an envelope can also provide the frequency, such as a median frequency, of respiratory effort modulation. (For example, a power spectral density (PSD) operation can produce spectral peaks with sufficient signal-to-noise ratio (SNR) versus the noise floor.) Thus, such information can be evaluated as an input feature(s) for the AHI and/or risk probability classifier(s). For example, this approach allows the system to be configured to extract the frequency of modulation over virtually any time period (e.g., typically greater than a single event). This also applies to the passive envelope. Optionally, the median of the active/SONAR modulation frequencies for the entire night/recording may be used for de-noising.

Combining Active and Passive Features:

An advantage of processing both active and passive sensing signals is that they both contain different information regarding a common sensing target. For example, they are measuring different aspects of the physiological signals that serve as a basis for estimating presence of different types of SDB. For passive sensing signals, the sounds of snoring and/or breathing are analysed, including intensity across different frequency bands. For active sensing signals, the displacement of the chest is measured (i.e., the system can sense chest movement when there is good signal quality).

In some circumstances, the active SONAR analysis can have difficulties (lower estimated signal quality) when the subject's back is turned to the sensor, and the person is under several duvets (blankets/comforters). For such a case, the passive analysis can still sense snoring and/or breathing sounds (including unstable breathing, as well as the air turbulence arising from breathing). The system also enables detection of periodic movements associated with SDB recovery/arousals. Here again the passive analysis may be useful when the actively detected breathing signal and/or the effort modulation is weak.

The combination of the channels can be optimized based on the determined signal quality with respect to the features derived from each approach (so as to emphasize the channel(s) with the better signal to noise ratio (SNR) or better quality).

For the case where both are deemed to be of acceptable quality, the system may then check how well the two channels are correlated, and leverage this information to estimate central vs. obstructive, and position of the person.

The system may detect snoring by proxy such as when the audio intensity modulation in audio bands (e.g., between 250 Hz-8 kHz) reflects the presence of snoring and the SDB indicators described herein is determined with such relative acoustic intensity.

The system may detect breathing sound of a person, and, optionally, evaluate the breathing sound or snoring as a basis to rule out occurrence of central apneas because they are usually not associated with snoring such as when breathing sound is detected at around 5 kHz. Such a frequency component associated with snoring tends to disappear during an event of central apnea.

It is possible that slow, periodic modulation due to environmental interferences can cause an issue on either of the passive/active sensing. As the system uses two different sensing modalities, it is less likely that both will have simultaneous poor or no physiological signal information. This is of course distinct from the case where the user leaves the room. The system can sense such an occurrence and, in this case trigger an "absence" mode, that can pause SDB screening until the user is "present" again, and resume SDB monitoring when the user is back and asleep.

Some Advantages Over Oximetry and Capnography:

Examples of the system described herein can estimate arousal time based on the small movements at the end of an event, which is an advantage over other sensing such as SpO2 which may not. An advantage over oximetry or capnography relates to the ability of the system to measure movements of part or all of the body that may occur as part of an SDB related arousal either through SONAR or audio. Other sensing modalities may only detect movements localised to the sensor site which may not be as useful for SDB detection.

Not only does the system measure chest modulation, it also detects movements due to recovery events, which is typically not seen in capnography.

Additionally, the system can implement a differentiation between sleep/wake, such as with the SDB related correction. This aids in SDB detection accuracy since AHI is defined as events/hr of sleep.

How to Avoid Detection of Second User in Bed:

For the case of two people in bed, multiple features may be considered by the system to separate the nearest person (the person to be analyzed) from the further away bed partner. The detection signal can be stronger for the closer person. As described in more detail herein the system may implement weighted averaging of the signals. Such a process tends to favour the stronger signal (by emphasizing it) and it tends to suppress the weaker signals. Thus, the processing can separate information from the nearer from information from the farther person. In some cases, if one person snores who is not the nearest person to the sensor, the snoring may be audibly sensed but related movement might not be sensed. Such inconsistency can be employed to separate (and optionally reject) partner snoring. In other words, the passive sensing analysis may not be consistent with the active analysis which can serve as a basis to reject a conclusion of SDB. For example, a voting mechanism, such as implemented with logic of the controller/processor(s), may be employed to select the better signal-to-noise ratio signal over a period of time. As the active analysis can contain range information (e.g., based on FMCW processing), it can be an effective means of rejecting data from a further away partner that is snoring. A weighted sum of the estimates based on quality can be used for example. If the two methods directly contradict each other over multiple timescales (which is highly unlikely), an error state may be flagged by the system.

For active sensing that produces varying range detections (range bins), the different range bins may also be used to localize the sensing area to the nearest person. The can even assist if the person rolls to the far side of the bed (e.g., further from or closer to the sensor).

The system can also implement natural shadowing, as the nearer person "shadows" (partially occludes) the further person for the case of a phone or sensor placed on the nightstand/bedside table; this applies to active sensing. Such shadowing may be facilitated by locating and orienting the sensor towards say the chest of the first person, so as to make it difficult for another person to move into the sensing field. Shadowing is a natural consequence of the sensing modality when the smart device is placed on a bedside locker or table, etc. near the first person being monitored. That is, the primary or closest user will partially or completely physically block the active sensing signal (e.g., SONAR waveform) from "hitting"/illuminating the secondary user and hence their movement/breathing is not measured, or is weaker. The same is true for passive audio to a lesser extent in that the secondary user is further away and thus their audio signal will be typically weaker. There may be reduced shadowing (and increased chance of a partner being detected) if the monitoring device is placed behind the bed, such as on shelving, facing down towards the user and bed partner. An FMCW active system, such as described herein, may be configured to distinguish the two persons by splitting multiple range bins.

The system can also make use of the fact that many modern smartphones have multiple speakers and mics—e.g., a bottom edge speaker box, and an earpiece receiver that can also serve as a second loudspeaker for stereo playback, and also a bottom edge microphone, and one or more mics on the top edge or top rear (camcorder) of the phone.

For example, users may want to listen, to relax, to sleep sounds (such as ocean wave sounds synchronized to their breathing) to help them fall asleep. A common issue on smartphone speakers is that by mixing the SONAR sensing sound with a music or other audio source, the emitted power of the sensing signal reduces, and the very small speaker and associated smart power amplifier may produce unwanted audible artefact that is not in either of the source signals due to non-idealities in the speaker and/or amplifier chain (even if the music has been low pass filtered so as to remove any frequencies that might overlap with the sensing waveform). One solution may separate the sound channels for separate speakers. For example, the system may route the filtered music to the second speaker only (which may require mixing of stereo music source to form a single channel representation), and play the SONAR sensing sound through the first speaker—thereby retaining sensing fidelity, as well as music/audio playback fidelity. Another approach is to use both speakers for sensing, but with different sensing frequencies ranges and/or repetition rates for each speaker. The reflections can be monitored by one or more microphones. This can be beneficial when the user is using more or more thick comforters (duvets) and/or blankets and signal levels are low, or for different height ceilings or wall materials. Typically, the two or more smart device speakers are pointing in different directions, and can utilise different multipath reflections to better detect the chest and body movement of the user. A reason for using different frequency ranges (either in absolute terms, or in time), is to allow straight-forward processing of the reflections (a coding scheme may not be required); in addition, as the speaker, microphone and associated amplifiers are usually non-linear in the ensign frequency ranges above 18 kHz, the second reflected echo signal provides a further source of information to derive respiration and movement from. It can also be seen that if a second speaker is used for playing sounds while a user is falling asleep, that once they are soundly asleep, it is possible to fade out the music and replace with a secondary sensing signal.

Sleep Staging that Ensures Sleep Related Breathing Disturbance

As part of AHI calculation, the system considers sleep detection so that breathing diminution or cessation is processed only during sleep. Therefore, by including a sleep staging process, such as described herein as well as in International Patent Publication No. WO2015006364 (PCT/US2014/045814), the accuracy of the system is improved.

Moreover, the number of apneic events may be defined in relation to detected total sleep time rather than a more simple assessment that considers a number of apneic events over a detection period that may not be limited to sleep.

PLM/RLS:

Periodic limb movement (PLM) and restless legs syndrome (RLS) can appear in the modulations detected by the system. However, these modulations are not as consistent as clusters of apnea, and can occur at different timescales. As a result, the system is robust to moderate levels of PLM, whereby the rate of repetition/occurrence of PLM is higher than that of apneas, and thus rendered distinct. Additionally, PLM and the RLS are unlikely to interfere because the person's limbs (including legs) are usually outside of the main sensing zone depending on the angle and location of the phone or sensor. Optionally, a separate or combined RLS/PLM detector can also be employed with the system herein to track these periodic movements. An example of such a detector may include any of the methodologies described in PCT/EP2016/080267, the entire disclosure of which is incorporated wherein by reference.

The signal combination carried out with passive sensing signals and active sensing signals can serve to mitigate PLM. For example, the system can implement greater weights for range bins related to movements where breathing occurs (e.g., weighting may be implemented based on strength of breathing). Thus, the system processing can help to prevent PLM from being a significant confounder for the system.

Teeth Grinding/Bruxism:

Teeth grinding/bruxism happens at higher (faster) rates, and not into the modulation range processed. Thus, such events may be avoided in the SDB detection methodologies described herein.

Central Vs. Obstructive Apnea:

The system can differentiate central vs. obstructive clusters based on the shape of parameters, and based on the relationship of features between passive sensing signal characteristics and active sensing signals characteristics. Central versus obstructive events may be detected as different types of modulation in the respiration effort signal. Obstructive events typically invoke an increase in effort (i.e., breathing against a restricted airway). Obstructive hypopneas are similar to obstructive apnea events although, since the airway is only partially blocked, the change in effort is smaller. Conversely, a central event would manifest as a reduction in effort vs baseline (i.e., no attempt made to breathe). Thus, a system may detect an event and classify the event by type by assessing whether it has an associated increase or decrease in effort, the characteristic shape or profile of the effort envelope and/or the relative change in amplitude versus the baseline effort (local or globally in time).

In some cases, the apparatus may be implemented to use snoring or other characteristic audio signatures (e.g., wheezing, choking) to determine that an event is obstructive in nature. For example, the system described herein may implement snoring or other sleep disordered breathing event detection as described in United States Patent Application Publication No. US-2018-0256069-A1, published on Sep. 13, 2018, the entire disclosure of which is incorporated herein by reference. Optionally, based on the quantity of central vs. obstructive vs. mixed events (and considering apnea or hypopneas), the system may be configured to recommend different types of therapy.

Changes in Position are Detectable:

The system can detect the relative position of the nearest person in bed, e.g., if they are facing the sensor, facing away from sensor, or on back or stomach. Examples of sensor configurations and methods such as for detection of position may be considered in relation to International Patent Publication No. WO/2017/032873, published on Mar. 2, 2017, the entire disclosure of which is incorporated herein by reference.

Inspiration Vs. Expiration:

In some versions, the system may implement RF detection (e.g., Doppler sensing) to separate or distinguish inspiration/expiration effort (inspiration always towards sensor as person is ballooning). Such a distinction may be implemented, for example, by processing the Doppler shift (e.g., detection motion direction change) so as to yield direction of travel of the target, which can be mapped to inspiration/expiration. A methodology for detection of motion direction change, which may be implemented to distinguish these breathing phases, is described in International Patent Application Publication No. WO 2016/170011, published on Oct. 27, 2016, the entire disclosure of which is incorporated herein by reference.

Producing the AHI:

The system can provide an estimate of AHI (apnea hypopnea index) or RDI (respiratory disturbance index). For example, this may relate to number of apnea and hypopnea events or number of apnea and events per hour of sleep. Thus, it can be seen if different types of apnea (e.g., a direct count of apnea and hypopnea events) and sleep time may be estimated by the system, it is possible to estimate an AHI value. Another approach is to provide longer scale modulation data (e.g., representing trains or sequences of apneas and/or hypopneas) into a machine learning model based on the estimates (labelled data) provided by one or more skilled human PSG scorers, and developing a classifier (such as a logistic regression model classifier) to estimate an AHI from those features. The system may provide an estimate of AHI and/or RDI and/or a metric quantifying risk of SDB (e.g., a probability output of a logistic regression model).

Combining with Other Risk Factors:

The output of the system can be combined with other risks factors—age, BMI, race, income, comorbidities, alcohol intake—in order to calculate and overall "risky sleep" index. This may be input to and characterized by the classifier(s) described herein.

8.3.4.1 System Processing Architecture

An example system architecture, such as with modules described herein, may be considered in reference to FIG. 8. Such modules may be implemented by any of the processing devices described in this specification such as an RF sensor based system and/or a mobile phone. Alternatively, the processing modules may be implemented separately from the sensors by processing devices located either nearby (e.g., a mobile phone or a tablet located in the vicinity of an RF sensor) or at a remote server. Generally, the system performs an assessment of the SDB risk from sensing signals associated from one or more sensing sessions with a sleeper (such as one night of sleep or multiple nights of sleep) such as from the acoustic and/or radio frequency based sensing devices described herein. The process(es) may be configured to generate an SDB risk indication such as to provide any one or more of:

(1) a binary classification flag (true or false) for exceedance of a clinical threshold of SDB events (e.g., AHI greater than a threshold such as 15). This threshold could be adjusted to 10 or 5, for example, or to be higher or lower as desired. Optionally, the binary classification flag may be symbolic. For example, such an indicator may be a color-coded output such as to indicate one color for true and another color for false (e.g., "green" for a count below the threshold (e.g., 15) and red for a count greater than or equal to the threshold.)

(2) a computed probability of SDB risk (e.g., as a percentage or a scaled indication in a range such as from 1-100 such as where one end of the range is less indicative of SDB and the other end of the range is more indicative of SDB);

(3) an estimated score of pertinent SDB events (e.g., an apnea-hypopnea index (AHI) or other count of SDB events).

In addition, the system may be configured to detect sleep stages and/or provide a sleep score, a mind refresh score/indicator and/or a body refresh score/indicator as described herein and generate output indicative of sleep stages based on motion detection. For example, this may be implemented as described in International Patent Publication No. WO2015006364, and filed on Jul. 8, 2014, the entire disclosure of which is incorporated herein by reference. Additionally, the system may be configured to implement corrections to sleep staging analysis such as to ensure that such staging determination is correct or more accurate—even for people/users who have severe SDB. In an example, described in more detail herein this may be implemented with a methodology (machine algorithm) that implements a sleep/wake correction mask, such as a time series of indicators representing a determination of sleep or wake from analysis of the sensing signals. Such a correction may be based on detection and evaluation of intensity of modulation that is detected in an SDB frequency range (e.g., modulations occurring in intervals of 25 to 100 seconds).

In this regard, the events tend to occur in succession, and the period between two successive events typically (based on empirical analysis) ranges between 25 seconds to 100 seconds. The system can be for example tuned to detect periodicity (i.e., modulation) in this particular range. A sleep/wake correction is applied when the system detects a 'cluster' of SDB events. Events within a cluster occur at a certain rate (or frequency). The system can also be configured to ignore events whose periodicity falls outside the typical "normal" physiological range associated with apneas, on the basis that these are more likely be spurious. A separate RLS and/or PLM detector may be employed.

As illustrated in FIG. 8, the processing, such as with one or more algorithms, may be implemented as multiple modules (e.g., three in the example). The operations/functions of the modules, which are implemented by one or more processors, are described in detail in the following sections and may be implemented as part of the methodology illustrated in relation to FIG. 7B-2. In this example, the operations modules may be implemented as (a) an extraction module 8810, which may be an online (where "online" in this case may be understood to mean the use of a processor to process blocks or frames of data as they are gathered, such as to give the fastest response to the user at the end of the night, and avoid buffering potentially many gigabytes of raw audio data) module, (b) an assessment module 8820, which may be an offline (where "offline" in this case may be understood to mean the "end of session" processing of intermediate parameters provided by previous "online" processing steps) module, and (c) an output module 8830 which may also be an offline module for output generation. Each are described in more detail herein.

Generally, the extraction module 8810 may be configured to perform signal extraction such as from active sensing signals (e.g., RF and/or SONAR) sensing signals and passive sensing signals (e.g., ambient audio/sound). Such a module may include, for example, multiple channels, such as for extracting I & Q (in phase and quadrature) respiratory effort signals from input sensing signals (e.g., raw motion signals from RF and/or SONAR motion sensing). The module may also have multiple acoustic channels, such as from passive detection, to isolate audio energy of interest such as to extract it into one or more bands of interest (e.g., nine channel bands).

Generally, the assessment module 8820, with the input signals from the extraction module, may determine modulation characteristics, such as frequency and intensity of modulation. The module may also calculate a sleep/wake correction mask based on determined modulation strength. Such a correction mask may be input to a sleep staging process that determines sleep stages (e.g., a hypnogram signal) so that the correction mask can be applied to correct or avoid indications of wake that are incorrect due to SDB. The assessment module 8820, such as with the intensity, frequency and sleep staging information (e.g., a hypnogram signal as corrected by the mask), may be applied to an SDB synopsis evaluation. In such an evaluation, SDB features (e.g., scalar values) may be derived from respiratory effort signals such as active sensing (e.g., SONAR and RF sensing), and frequency bands from passive acoustic sensing. The features may be applied to one or more classifiers. For example, a logistic classifier may classify the scalar values to produce a binary classification flag and risk probability indicator as previously discussed. By way of further example, a linear regression classifier may classify the scalar values for calculation of a respiratory event score (e.g., an apnea/hypopnea index that counts such events). Such a calculation of the respiratory event score may be applied as an adjustment factor, such as an SDB penalty factor, that may adjust one or more portions of a sleep score, such as to serve as an adjustment factor in a body refresh score/indicator and/or a mind refresh score/indicator.

Although the operations are illustrated in the example of FIG. 8 so at to divide the operations into real time or near real time (during recording of sleep session) and finalisation at the end of or after the recording and/or sleep session, other separations of operations may be implemented. The operational divisions in the illustrated example may provide a particularly efficient use of a processor, such as when implemented by a smartphone.

Nevertheless, the online and offline operations may be implemented such that they are all processed as offline, or aspects of the offline operations may be implemented as online processing. As shown, the separation of online and offline are designed to efficiently utilize a multicore smartphone processor, but could be adjusted based on the characteristics of available processor(s) and availability of storage/memory.

8.3.4.1.1 Extraction Module 8810

The purpose of the extraction module 8810, such as by implementing continual or periodic processing, whether during a sleep session or after, is to regularly calculate pertinent information signals from active sensing signals and/or information signals from passive sensing signals (e.g., non-contact sensing). Such extraction processing will depend on the nature(s) of the sensing signals such as whether they are RADAR (i.e., RF) and/or SONAR originated.

For example, for active sensing information signals, the extraction process may produce a respiratory effort signal, which is based on non-contact respiratory motion sensing. Such a respiratory effort signal may be generated in the SONAR case as previously described herein and/or in accordance with the methodologies described in International PCT Patent Publication No. WO2018/050913, and in the RADAR case as described herein and/or in accordance with the methodologies described in International PCT Patent Publication No. WO 2014/015238 or U.S. Pat. No. 8,562,526, issued on Oct. 22, 2013.

In one example, one or more respiratory effort signals may be generated from SONAR or RF demodulated signals such as by producing two channels (I and Q) respiratory effort signals at 16 Hz. Optionally, other sampling rates may be implemented by the system. For the case of a frequency modulated continuous wave (FMCW) active front end sensing (acoustic or radio frequency), a task of this extraction module is to perform FMCW respiratory effort detection. Such active sensing signal extraction processing may be implemented with one or more active sensing signal extraction sub-module 8812. Such sub-modules may be implemented with a SONAR sensing signal extraction sub-module and/or RADAR sensing signal extraction sub-module.

In addition, for passive sensing information signals, the extraction process of the extraction module 8810 may extract information signals from an acoustically sensed audio signal. Such a passive-audio energy may be extracted from a full band audio signal (such as the detectable audio range of an implemented microphone) into relevant bands for SDB (e.g., nine channels with different frequency bands). Such signals may be produced at 1 Hz but other sampling frequencies may be implemented as desired. Such passive audio signal extraction processing may be performed by the passive sensing signal extraction sub-module 8814.

In some cases, the extraction module 8810 may further implement modules or sub-modules for extraction of a respiration rate signal and/or a signal quality signal. The respiration rate signal represents respiration rate over time and the signal quality signal indicates quality of the recorded sensing signal(s) over time.

8.3.4.1.1.1 Extraction of Respiratory Effort Signal from Active Sensing Signals The processing of active sensing signals such as for generating/extracting a respiratory effort signal (based on respiratory motion) in 8810A may be considered in reference to FIGS. 9, 10 and 11. In some versions, such processing of the sensing signal may include processing to combine complex demodulated sensing signals from multiple ranges (range bins) (see FIG. 9), where each range bin signal may be in two channels (one for the real part (which may be an I signal) and one for the imaginary part (which may be a Q signal) respectively). Typically, there are two inputs desired for extracting the respiratory effort signal:

a. The sonar signal in each range bin over a period of, for example, 5 seconds
b. Respiration analysis for each of these range bins.

The respiration analysis tells us how much respiration signal is present in each range bin, based on a metric quantifying highest spectral power density in the respiration frequency range. This respiration analysis may be performed each interval (e.g., 5 seconds) (over a signal spanning for example a longer period, such as 64 seconds). For each range bin we will have the metric output at the left and right boundaries of the, e.g., 5 second domain.

A way to combine all the range bins into one single channel via the respiration based metric may include a process with the following steps:

a. define weights for each range bin, at the left and right boundaries of the domain, by dividing the metric corresponding to the particular range bin by sum over all range bins;
b. interpolate linearly the weights between left and right for each range bin
c. multiply the weights with the signal in each range bin
d. sum up the above over all range bins The analysis may be performed in alignment (time) with a sonar respiration analysis, such as in periods of 5 seconds, and the effort signal is extracted using signals from the range bins that include respiration information. In the example sensing signals from FIG. 9, this includes signals from range bins at 0.3 to 3 m.

The processing may help to address any of the following challenges:

(a) Signals can change phase by 180° from one distance range bin to another;
(b) Distance range bins that do not contain modulation in the respiration range (i.e., respiration motion frequencies) must be excluded;
(c) Continuity should be ensured between successive 5 second segments, accounting for possible changes in subject position.

Accordingly, as illustrated in FIG. 10, such a process may involve applying an absolute value process for each discrete range signal or range bin and then combining the range bin signals according to weighted averaging of respiratory related frequencies from PSD operations. The process may be performed for each of the I and Q channels respectively. An example may be considered with the following processing:

(1) Weights may be computed from the metric consisting in the highest power spectral density (PSD) in the respiration range, at the left and right boundary of the 5 seconds domain, for each range bin;
(2) Weights may be distributed across the domain via linear interpolation between the right and left boundaries;
(3) The range bins may be combined by
  (a) taking the absolute value of each range bin;
  (b) taking the weighted average of the above via multiplication with the array of weights.

For this example, a weight is simply a scaling factor that is applied to each range bin's signal. This proportionally 'weights' certain range bins more heavily than others. When assessing respiration rate, normalisation may be desirable to suppress the large amplitude modulation component. However, this amplitude modulation (AM) component is retained for SDB analysis, as it includes modulations of interest relating to SDB over longer timescales.

8.3.4.1.1.2 Extraction of Passive Audio Signal for SDB

The processing of passive sensing signals such as for generating/extracting frequency bands in sub-module 8812 may be considered in reference to the frequency spectrum of the audio signal shown in FIG. 12. This sub-module transforms the raw, full-band, audio signal into the frequency domain such as for later generation of a measure of energy for the different frequency bands. The extraction of the passive audio signal for SDB may involve separation of the audio signal into frequency band signals (e.g., 9 discrete frequency bands that partition a range such as a range of about 100 Hz to 8 kHz or 250 Hz to 8 kHz). In some versions, eleven frequency bands may be implemented such as where the bands are nominally spaced in 250 Hz intervals in the range. The extraction processing may be performed every second (1 Hertz). This may be implemented with a Fourier transform, such as a discrete or fast Fourier transform.

For example, the extraction may include the following processing:
(a) An FFT (e.g. "4096 point") may be calculated, such as 16 times per second, on samples of audio data (e.g., 3000 samples). This may optionally be performed after de-meaning and spectral windowing is applied. In some cases, the median (e.g., performing median removal on, for example, a one second basis) rather than the mean removal may be used. Other sizes may be used, such as 1024 pt FFT on 1000 samples of audio data and so forth (e.g., non-overlapping frames).
(b) The energy in each frequency band may be determined by calculating the sum of the absolute values of the corresponding FFT coefficients of a particular frequency band. Each such sum may be considered the energy value of each frequency band. For the example case of 9 frequency bands, each FFT operation will result in a computation of 9 energy values.

To extract each band signal for SDB assessment, an average value from the energy values of each band may then be determined (computed) such as over one (1) second window. In the example of conducting the FFT 16 times per second, each band will average 16 energy values. The process, when repeated, thus produces separate signals over time for each band (e.g., 9 for SDB and respiration) where each sample of the signal of a given band represents average energy from a time interval. The system may detrend the 9 bands, and then take the average. Then the envelope peak finding is performed, a peak interpolation is carried out etc. as separately described (e.g., by integral generation and high pass filtering). For respiration, each band is processed for respiration independently, with pre-processing and autocorrelation. The autocorrelation output is used with a signal quality metric when there is a prominence of peak), to select the channel(s) that may contain respiration, and combine them. This may be repeated, e.g., every few seconds (e.g., 5 second) using a sliding window (e.g. a 64 second sliding window).

The extraction of the active and passive envelopes may also be carried out. An active signal envelope extraction may involve steps of: (i) invalid data interpolation, (ii) outlier removal, (iii) IIR Low Pass filter with cut off at 0.075 Hz (or some other low value), (iv) compensation for filter delay, (v) down sampling @1 Hz.

The passive envelope extraction may involve the steps illustrated in FIG. 8B. This may involve any, some or all of the following steps: (i) channel combination, whereby the baseline for each band is removed by subtracting the minimum over a sliding window, and the bands are combined by taking the mean over the bands. As illustrated, (ii) the process may decimate the passive stream such as with (e.g., anti-alias filter), which may be followed by (iv) downsampling. These improve efficiency such as by reducing the raw 48 kHz signal by a factor (e.g., a factor of 3).

Optionally, (iii) spectral de-noising may be performed on the spectra prior to other processing using a filter, such as a Wiener filter (using a running SNR based on changes over time) in order to enhance the SDB modulation detection, as well as respiration channel selection.

The denoising process may be carried out in the frequency domain. The purpose of this process is ultimately to obtain an estimate of the signal of interest only from the measured signal, which also includes noise, i.e. to remove the noise from the signal. This may be done through the spectral product (convolution in the time-domain) of the noisy version of the signal (i.e. what is actually recorded by the system) with a spectral gain G (to be determined):

$$\hat{S}(p,k) = G(p,k) X(p,k)$$

where $\hat{S}(p, k)$, $G(p, k)$ and $X(p, k)$ are the $k^{th}$ components of the short-time audio frame p (a $\frac{1}{16}$ second, 16 kHz, non-overlapped, frame in the algorithm) for: the estimated signal, the gain, and the measured signal plus noise, respectively. In the algorithm the spectral signal X may be obtained using a 1024 point FFT applied to a Hanning windowed version of the frame p. For example, frame p is taken from the 16 kHz output of the decimated raw 48 kHz signal from the smart device's microphone.

The spectral gain G is a function of two components: the a posteriori and a priori Signal-to-Noise Ratio (SNR) of the audio frame. These terms refer to the SNR calculation in the presence and absence of knowledge of the true noise for a particular audio frame p. They can be defined as:

$$SNRpost(p, k) = \frac{|X(p, k)|^2}{E[|N(p, k)|^2]}$$

and $$SNRprio(p, k) = \frac{|S(p,k)|^2}{E[|N(p, k)|^2]}$$

where, $S(p, k)$, $N(p, k)$ are the $k^{th}$ components of the short-time audio frame p for the signal and noise, and E is the expectation operator.

The gain G can then be described using estimates of the above SNR values:

$$G(p,k) = g(\widehat{SNR}\,prio(p,k), \widehat{SNR}\,post(p,k))$$

The function g can take a number of different forms (see, e.g., Ref C. Plapous, C. Marro, P. Scalart, "Improved signal-to-noise ratio estimation for speech enhancement", *IEEE Trans. Audio Speech Lang. Process.*, vol. 14, no. 6, pp. 2098-2108, 2006.). One example approach that can be employed is the Wiener Filter.

(v) Once the denoising process is complete the energy in the bands may then be obtained from this denoised spectral signal and added to a first in, first out, FIFO buffer (e.g., a 64 second circular buffer).

Signal Quality and Respiration Rate

In some versions, this module 8812 may optionally implement analysis of signals, such as active and/or passive signals, to estimate a respiration rate and/or a corresponding signal quality. In some versions, respiratory rate (breathing rate) may be determined as described in International Patent Publication No. WO2015006364. Such information may be implemented as part of an absence/presence detection module that identifies whether or not a person is in the sensing vicinity to improve the robustness.

The system may calculate respiration rates independently via both active and/or passive streams, and optionally combine the outputs based on estimated signal quality of each.

Passive Respiration Rate

Respiration rate (either active or passive) may optionally be used, for example to improve accuracy of the system when there is good signal quality. For poorer signal quality situations, the modulations can still be detected to identify clusters of apneas/hypopneas—even if real-time breathing rate is not available for parts of the night/sleep session.

In some versions, this sub-module may be configured to process each of the above discussed frequency band (e.g., in buffers) and estimate a respiration rate and/or signal quality for each period (e.g., a 64 second buffer) (such as previously described). This may be repeated every 5 seconds in alignment with a respiration rate determined from the active sensing signals (e.g., a SONAR derived respiration rate).

As the breathing signal from passive analysis generally takes the form of periodic impulses, some pre-processing is first applied to help improve the robustness of the algorithm. Example steps may include any of the following:
1. Apply a matched filter with a Gaussian impulse response
2. Remove baseline by subtracting the minimum over a sliding window
3. Limit at the $95^{th}$ percentile to minimize artefacts from movement etc.
4. Normalise by the std.dev (standard deviation) over a short sliding window
5. Integrate the signal and high-pass filter
6. Normalise once more by the std.dev over sliding window By completion of such pre-processing, the impulse train has been transformed into a signal more suitable for time domain analysis.

An autocorrelation may be performed on the signal and the first peak within the defined respiration range is selected as a respiration rate estimate. The peak prominence is calculated and used as our signal-quality or confidence metric. This process may be repeated for each frequency band.

Finally, a respiration rate estimate may be calculated by taking the average of the four estimates with the highest signal quality. The signal-quality output is simply the average of the highest four signal-quality metrics. Such output(s) may optionally output to the assessment module 8820 or any of its sub-modules/processes.

8.3.4.1.2 Assessment Module 8820

As illustrated in FIG. 8, the assessment module 8820 may include an SDB modulation assessment sub-module 8822 or process, a sleep staging sub-module 8824 or process, and SDB synopsis sub-module 8826 or process. Each are discussed in more detail herein. In general, the SDB modulation assessment process may implement an assessment of SDB modulation (frequency and/or intensity) for each of the signal stream from the extraction processing (i.e., active (e.g., SONAR or RADAR derived respiratory motion signal(s)) and passive (e.g., audio acoustic signal(s)) respectively. One can consider the term "SDB modulation" as modulation, in the respiration/biomotion signal amplitude, and longer term envelope variation, due to SDB related events.

Moreover, the SDB modulation assessment process may identify time segments (i.e., portions of the input signals) that contain significant or strong SDB modulation (clusters) for each of the active signal stream and the passive audio signal streams respectively provided by the output of the extraction processing. Moreover, SDB modulation assessment sub-module 8822 may generate a correction mask as previously described which may provide sleep/wake characterizations to serve as input for improving sleep stage indications of the sleep staging process of sub-module 8824. As illustrated in FIG. 8 and explained in more detail herein, the evaluation of SDB synopsis sub-module produces an AHI and a binary flag, for example, which is/are output (such as to a screen or other user interface) such as by the optional output module 8830.

8.3.4.1.2.1 Assessment of SDB Modulation—Sub-Module 8822

The active (e.g., SONAR) and passive audio streams (i.e., signals produced by the extraction processing of the extraction module 8810) are processed separately in order to derive spectral characteristics quantifying modulation in the SDB frequency range (25 to 100 seconds). Many of the processing steps are similar for the two streams.

(A) SDB Modulation in the Active (e.g., SONAR Derived) Stream

For each of the I & Q channels representing respiratory effort, the following processing determines modulation intensity in relation to a particular SDB frequency of modulation. In general, as illustrated in FIG. 11, an envelope is extracted from each channel/signal. The envelope may be filtered and/or normalized. The envelope is processed by spectral analysis to determine a modulation frequency characteristic in an SDB related range (e.g., about 25-100 seconds) and/or an intensity characteristic thereof. Modulation intensity at that SDB related frequency may be output to the SDB synopsis sub-module 8826 as discussed in more detail herein. Example steps to produce such output may include:
1) Envelope extraction (FMCW Extract Envelope):
   a. NaN interpolation
   b. Outlier removal
   c. IIR LP filter with cut off at 0.075 Hz
   d. Down sampling @1 Hz
2) Envelope normalization via a mixer approach (normalize Envelope):
   a. Initial scaling by overall median value
   b. Linear combination of the envelope at step a) above and the envelope scaled by the standard deviation over a sliding window
3) Extraction of spectral characteristics in the SDB frequency range (get Modulation Frequency, compute ibm (in band metric)):
   a. FFTs (e.g., 1024 point) are performed every minute, over windows of 6 minutes, after the application of detrending and spectral windowing.

b. The following spectral characteristics are extracted:
   (i) (Peak: the frequency corresponding to the peak PSD in the SDB frequency range (i.e., SDB band—for example 25 to 100 seconds)
   (ii) ibm (in band metric): the corresponding intensity of modulation or signal quality, taken as:

$$\frac{P\text{signal}}{P\text{noise}}$$

Where "P signal" is the power contained in a band (e.g., a narrow band) around the peak frequency and "P noise" is the difference between the total power and P signal Finally, the average of the two channels may be determined to produce a signal that represents the intensity of modulation (the average SDB in-band metric (ibm)). This average value may then be evaluated to define SDB clusters (active clusters) for the active stream (e.g., SONAR or RADAR) in the SDB synopsis sub-module 8826 as discussed in more detail herein.

(B) SDB Modulation in the Passive Audio Stream

With the audio band channels (e.g., 9 in the example), the following processing detennines modulation intensity in relation to a particular SDB frequency of modulation. In general, as illustrated in FIG. 13, an envelope is extracted from the combined channel/signals. The envelope may be filtered and/or normalized. The envelope is then processed by spectral analysis to determine a modulation frequency characteristic in an SDB related range (e.g., about 25-100 seconds) and/or an intensity characteristic thereof. Modulation intensity at that SDB related frequency may be output to the SDB synopsis sub-module 8826 as discussed in more detail herein. Example steps to produce such output may include:

1) Channel combination:
   a. The baseline for each band is removed by subtracting the minimum over a sliding window.
   b. The bands are combined by taking the mean over the bands.
2) Envelope extraction:
   a. Peaks are extracted, imposing a minimum peak separation of about 5 seconds
   b. The envelope is derived by interpolation @1 Hz and application of a mean filter.
3) Envelope filtering including integrating and high pass filter (pass band frequency at 1/100 Hz):
   This step is applied to convert impulse trains (which are the signature of obstructive apnea in the passive audio signal envelope) to signals more suitable for spectral analysis
4) Envelope normalization—identical to Step 2) from the sonar stream processing
5) Extraction of spectral characteristics in the SDB frequency range—identical to Step 3) from the active stream processing described above.

The modulation intensity signal at the SDB related frequency produced here, which is based on the passive signal sensing, may also be output to the SDB synopsis sub-module 8826, where it may then be evaluated to define SDB clusters (passive clusters) for the passive stream.

(c) Calculation of a Sleep/Wake Correction Mask for Sleep Staging in the Active Audio Stream The sub-module 8822 may also produce a sleep/wake correction mask based on a generated cluster flag that characterizes a presence of detected SDB clusters such as in the active sensing stream. Such an approach may assist in addressing the following factors:

To ensure consistency between the sleep staging (e.g., if performed based on sonar features only) and SDB assessment Performance of the active sensing signal (e.g., sonar) features for SDB screening is superior to passive-audio features alone The mask is activated when detected SDB clusters make up more than a predetermined percentage (e.g. 20%) of the overall recording session duration.

The mask is produced to mark periods of strong SDB modulation to reflect that the period should be marked as a period of sleep. This output correction mask is input to the sleep staging module 8824, where it is applied after the sleep/wake classification of the sub-module to correct instances (periods) of wake classification to be marked as instances/periods of sleep, consistent with the SDB modulation determination in the mask.

8.3.4.1.2.2 SDB Synopsis—Sub-Module 8826

As previously described, the assessment module may assess the input signals (e.g., modulation intensity as SDB related frequency from active and passive sensing signals) to determine an SDB classification flag, a probability of SDB risk and/or a score of SDB events. Such determination(s) may also be based on sleep staging information, such as from the sub-module 8824. Such determinations may initially involve detection of SDB related clusters which represent segments (time periods) that include SDB related modulation. Such determination is described in more detail herein.

(A) Identification of Segments with Strong SDB Modulation (Clusters)

Clusters of strong SDB modulation are identified based on the modulation intensity metric for each of the active (e.g., SONAR and/or RADAR) and passive audio streams. The process may include any of the following processing:

A binary flag signal (time series) is constructed by evaluating a minimum threshold for the metric. For example, for values of the intensity signal(s) at or above the threshold, the flag is set to true and false otherwise. This "intensity" relates to the intensity of modulation of amplitude/power and/or the intensity of frequency modulation of the active or passive sensing streams.

Optionally, the intensity signal(s) may be filtered, such as by applying a 10-tap mean filter is to the intensity signal(s).

The cluster flag signal may be obtained or modified by additionally evaluating the additional, post-filtering intensity signal(s) with a secondary threshold. For example, for filtered intensity values at or above the second threshold, the flag is set to true and false otherwise.

Such thresholds may be optimized, such as with empirical analysis, to maximize accuracy in detecting actual SDB clusters derived from PSG annotations. Cluster signals from such processing are illustrated in the bottom graphs of FIG. 11 (clusters from active sensing signals) and FIG. 13 (clusters from passive sensing signals).

(B) Classification

As previously mentioned, the SDB synopsis sub-module 8826 may include one or more classifiers to classify the input from the aforementioned processing for determination of any of SDB risk, SDB identification and/or event scoring.

For example, such a module may compute SDB related features such as one or more scalar values characterizing the entire recording-session from the active sensing stream (e.g., scalar values from any of the intensity signals from I and Q channels, cluster signal(s), respiratory rate signals, signal quality signals, sleep stage etc.) and from the passive sensing stream (e.g., intensity signals, cluster signal, respiratory rate signals, signal quality signals etc.) The module may, for example, apply a logistic model classifier to generate the binary SDB classification flag and associated SDB risk probability, and/or apply a regression model classifier to generate (a) an estimate of an AHI score or (b) a risk probability value that the sleep session included a number of apnea and/or hypopnea events that is greater than a threshold (e.g., a threshold indicative of a sleep disorder). The module may also generate a sleep score adjustment (e.g., penalization) factor based on assessment of the SDB probability. This may be applied to modify a sleep related score determined by the sleep staging module 8824 which is input to the SDB synopsis module 8826.

Example SDB related features for any of the classification processes that may be determined by the processing devices may include any one, more or all of:

1. cluster_ratio_active feature: This feature may be the proportion of total sleep time consisting of SDB clusters as derived from the active sensing stream (e.g., SONAR sensing). This feature may be derived by a processor as follows:
   a. Generated hypnogram data is evaluated to derive a total sleep time and a sleep-wake mask. The hypnogram as determined by the sleep staging process identifies different stages of sleep (e.g., deep, light, REM) or wake over the course of the recording session. The sleep-wake correction mask is a time series of indicators for the recording session that represents either sleep or wake in a particular time sub-interval of the time series. Thus, the sleep indicator of the mask summarizes any of deep, light or REM, etc. as a sleep interval.
   b. The sleep-wake mask is then evaluated in time relation with the sonar cluster time series to permit identification of the time associated with particular SDB clusters that occur or coincide with sleep (i.e., a sleep indication of the mask).
   c. The proportion of the feature may be calculated by dividing the SDB cluster related time by the total sleep time (e.g., SDB cluster time/total sleep time).
2. cluster_ratio_passive feature: This feature is also the proportion of total sleep time consisting of SDB cluster as described above but derived by a processor with the SDB cluster time series that is determined from the passive-audio stream rather than the active sensing stream.
3. fpeak_median feature: This feature is a peak intensity or peak median intensity that may be determined from the SDB modulation frequency time series (i.e., the previously described intensity signal(s)) from the active sensing stream. Optionally, this feature may instead, or additionally as an added feature, be based on the passive sensing stream. The feature may be on a time series of modulation frequencies from either the sonar stream or the passive sound stream. Such a feature may be determined/calculated by a processor as follows:
   From the active sensing stream (e.g., fpeak_median_active);
   (a) Periods with absence may be screened out;
   (b) I & Q channels, if present, may be combined such as by taking the minimum, which may represent a least noisy channel of the channels, for further processing; Alternatively, the I & Q channels may be smoothed by applying a 3-point median filter, and the channels combined by extracting the value corresponding to the channel with the highest modulation strength, and a 3-point median filter is applied for smoothing to the ibm (in band metric)
   (c) The feature(s) may then be computed by calculating the median of the signal or combined minimum signal, for periods where the modulation intensity exceeds a threshold. Optionally, isolated one point blocks may be excluded from the estimate. A minimum frequency may be returned if the cumulative duration of the exceedance blocks is smaller than a threshold. If the active cluster proportion is large, the frequency feature may be computed as the mean over the active cluster.
   From the passive sensing stream (e.g., fpeak_median passive);
   (a) a 3-point median filter maybe applied to the modulation frequency time series for smoothing;
   (b) the median over passive clusters may be taken as the feature.

The classifiers may then evaluate any one, more or all of these features to generate the binary flag, risk probability and/or the estimated count of SDB related events (e.g., an AHI estimate).

The output risk probability of an apnea/hypopnea count being greater than a threshold (e.g., AHI>=15) and the output flag (e.g., a positive SDB flag or the SDB classification flag) outputs are determined/calculated by applying a default logistic model on the classification features (e.g., cluster_ratio_active, cluster_ratio_passive and/or fpeak_median (e.g., fpeak_median_active and/or fpeak_median_passive)).

An estimate for an AHI score (an estimated count) may also be computed by applying a linear regression model on the same features. To avoid the risk of contradictory outputs, the regression model may be 'slaved' to the logistic model. Thus, if the predictions of the regression and logistic model do not agree, the AHI score may be modified based on the probability output.

The system may return invalid outputs (NaN), such as to identify that a SDB risk determination could not be made, under the following conditions: when the total presence time is less than a threshold (e.g., 4 hours); when an artefact detector rate exceeds a set threshold (e.g., an indication poor signal quality), and/or the default model returns positive (e.g., positive SDB indication) and a model based on passive features only returns negative (e.g., there are contradicting results from different detection methods).

In some versions, the SDB threshold may be set at AHI of 15. A positive outcome may in this case indicate an AHI>15. Following such an outcome, the user may be recommended, such as via an automated message on a display, for a follow up with a medical practitioner.

As previously mentioned, the processor may also determine an adjustment factor or the sleep score correction factor, that may, for example, serve as a sleep score penalty when SDB events disrupt sleep. Such an adjustment factor may be computed by a processor according to the following function:

$$\text{Factor} = \min[1, \text{slope} \times \text{risk\_prob} + \text{intercept})]$$

The slope and intercept may be predetermined or set such that the factor satisfies the following two criteria:
(a) The factor will be equal to 1 (no penalty) for subjects classified as negative (e.g., the probability of SDB risk is zero or below a threshold);
(b) The factor will be equal to a minimum value (e.g., 0.6) when the "risk_prob" or the SDB risk probability (e.g., a probability of the user having an AHI greater than a count threshold (e.g., 15)) is 1 (e.g., 100% or greater than a percentage threshold).

Thus, in the example, the factor will vary between 1 (no penalty) down to 0.6 (full penalty) in relation to the determined value of the SDB risk probability. The factor may then be applied, such as by multiplication, to any one, more or all of the following: (1) Total sleep time, (2) Deep sleep time (3) REM sleep time and (4) Light sleep time. Such sleep times may, for example, be determined from motion signal analysis, whether from SONAR or RF sensors, as described in International Patent Publication No. WO2015006364. The factor, such as in the presence of SDB probability risk, can then serve to penalize a reported sleep score, body refresh score and/or mind refresh score. In some such versions, any of the factor adjusted sleep time(s) may be output on a display, for example, in relation to the non-adjusted sleep time(s), to provide a visual indication of the effect of the SDB condition on the nature of the user's sleep or sleep time. For example, a bar (or any alternative) graph of a sleep time may be displayed on a display device with a certain color and a portion of that bar graph that is attributable to the penalty, may be shaded or presented in a different color so as to show the reduction in relation the whole. Alternatively, 2 adjacent bars (or other shapes) may be shown—one with, and one without the penalty factor. Such a visual indication may serve to motivate the user to seek treatment, or increase compliance, for the SDB condition, such as in relation to use of a therapy device (e.g., an RPT device). Optionally, such penalized/reduced sleep time may simply be shown as the reduced whole, without providing any demarcation to indicate the penalty.

A corrected sleep related score (e.g. a sleep score, a mind recharge score, a body recharge score) based on SDB may be calculated as follows. The sleep score correction factor may be computed as above. The slope and intercept may be calculated such that the factor: (i) is equal to 1 for subjects classified as negative, (ii) is equal to a minimum value of (say) 0.6 for a probability that AHI>=15 is 1.

The factor may be applied to reduce the components of the Sleep related Scores including for example, any or all of the following components:
Total sleep time
Deep sleep
REM sleep
Light sleep The penalization thereby affects the sleep score, body recharge score and mind recharge score which are derived from these adjusted components. Such scores may be determined in accordance with the disclosure of PCT/US2014/045814, filed on Jul. 8, 2014, the entire disclosure of which is incorporated herein by reference.

8.3.4.1.2.3 Cough Assessment

In some versions of the present technology a cough assessment(s) may be implemented, such as with the extracted signals and/or other processing of the active and/or passive sensing signals for the aforementioned sensor(s). Such a system may be implemented with cough assessment module 8833 as illustrated in FIG. 8A. Such an assessment, for example to produce indication signals regarding cough events, may be implemented either in combination with the aforementioned assessment module 8820, as shown in FIG. 8A, or as an independent module that is separate from assessment module 8820. For people who are sleeping (e.g., in bed, on a couch, in a chair) cough/wheeze/sneeze detection can run in parallel with SDB detection. For people awake, SDB detection need not run as the input is always (or nearly always) "wake". A sleep score can be reduced (penalised) as coughing worsens, for example, by appearing as an increase in a sleep disruption or sleep fragmentation index. An overall quality of life score could be reduced by both daytime and night time coughing or other respiratory events.

In this regard, it has to be noted that the cough assessment is useful for assessing variety of cough types, some of which may be indicative of the severity and the progression of a number of serious respiratory conditions, as explained below.

Asthma is a chronic inflammatory lung disease characterized by recurrent episodes of breathlessness, wheezing, and coughing (www.cdc.gov/asthma/interventions/background.htm).

Cough-variant asthma is a specific type of asthma in which the main symptom is a dry, non-productive cough—and may not have other common asthma symptoms such as shortness of breath or wheezing. This may be referred to as "chronic cough", may last longer than six to eight weeks, and may include sleep interruption.

A meta-analysis by Song et al. (European Respiratory Journal, 2015) to estimate the epidemiological burden of chronic cough in general adult populations found a high global prevalence (9.6%), comparable to that reported for asthma or chronic obstructive pulmonary disease. Chronic cough showed a 7.9% prevalence when the most stringent definition "cough>3 months" was used.

People with cough may be divided into those with acute (typically viral) illness, and those with chronic cough. Acute cough represents the largest single cause of consultation in primary care, whereas chronic cough is one of the commonest presentations in respiratory medicine—a demonstrably significant burden on the healthcare system.

There is significant benefit in being able to classify cough attribution types—such as asthmatic, COPD, bronchitis, tuberculosis (TB), pneumonia, lung cancer etc.

The social and financial burden of cough is great, especially if considering work and school absenteeism due to the common cold (estimated at up to 100 m absences worldwide—Altman & Irwin, Cough: An Interdisciplinary Problem, 2010).

The world-wide market in cough treatments is several billion dollars; e.g., the global cold & flu oral syrups market is $11 billion, with the global OTC cough, cold and allergy medicine market estimated to increase at a CAGR of 4.9% during 2017 to 2022 to reach a valuation of US$37 billion (Factmr, 2017).

The cough's signature is related to its mechanics. The medulla's "cough center" of the human brain prepares you for a cough, and causes the activation of the diaphragm downwards to pull air into the chest, and the glottis closes, followed by contraction of the diaphragm and intercostal muscles to build up pressure in the chest, until the glottis opens and the pressurized air escapes (potentially with any irritants that caused the cough action). The inhalation, forced exhalation, and glottal closure are sometimes referred to as the three phases of cough, with the forced exhalation being the main sound source that may be heard.

Therefore, it can be seen that this inhalation and release is characteristic in terms of detected chest wall motion (the pulling air into chest, then expulsion under pressure), as well as the acoustic signature of the inhales, closing glottis, opening glottis, and release (the "sounds" that say a human can associate with a cough). This has a different signature to a wheeze, sneeze, gasp, crackle or whistle for example.

Untreated flu or the common cold (especially with associated wheezing and coughing) can lead to life threatening pneumonia. A person may also experience mucus of varying color and volume. An asthmatic cough may be productive (producing phlegm) or non-productive (dry cough), and may or may not be accompanied by wheezing (a high pitched whistling sound resulting from the constricted airways). Wheezing and crackling may be inspected by a physician using auscultation for example.

Most of the cough episodes are self-limited and disappear after a respiratory infection is resolved with or without specific treatment. Cough that persists will need medical attention (e.g., such as if it is related to lung cancer). One of the most important things when dealing with cough is to determine if an acute serious disease causes the cough or not. The vast majority of acute cough causes are benign upper respiratory tract infections, such as the common cold (Chest Foundation, 2018).

Chan et al. (Eur Respir J. 2010) note that chronic cough (which is more prevalent in women) can be the sole presenting symptom for patients with obstructive sleep apnea. They further note: "SDB cough is not well recognized by physicians and it is possible that some patients referred to specialist clinic for investigation of the cough are misdiagnosed. It is important to recognize SDB cough because preliminary reports suggest it responds well to specific therapy for SDB."

Therefore, it is suggested that an application-based cough detection system, such as the one described here, could be of various benefits to people, including in terms of increasing SDB awareness in the population.

Other potential cough assessing solutions require specific hardware/devices to be purchased and worn—such as bands, bracelets, necklaces, rings, patches, watches or placed beside the bed/sleeping area or within the living space.

Many existing systems also require expensive external microphones, and these may need to be placed on or very close to the body (e.g., clipped onto a lapel, placed on neck, as part of a lab-on-chip patch etc.), and be used in very quiet environments. Additionally, they may require large amounts of data storage. This may create privacy concerns, as conversations may also be recorded. Such systems also employ offline processing, including manual human consideration of possible coughing episodes. For body worn devices, the battery capacity of a device may ultimately limit the sampling rates/bit depth of audio (i.e., reducing the potential quality of cough classification, and the discrimination between this and background/spurious sounds) versus time between recharges, and/or skin irritation due to adhesive when used for long periods of time; in contrast, contactless systems can use larger power sources or be plugged in via a transformer etc. to an AC outlet/electricity supply. Previous technology may also attempt to detect cough or classify cough type of pre-detected cough, but require specialized hardware such as by employing professional/specialized microphones placed near the neck with the aforementioned constraints. Such systems may have wear and tear to the mics/transducers over time, be affected by handling, water/sweat and have undesirable cosmetics. For example, they may be potentially undesirable in appearance as well as obtrusive such that they make people appear sick to others. Thus, they may not be worn in public, or may not be replaced after washing.

In contrast the cough assessing system described herein is based on a non-contact (e.g., acoustic) cough sensing and is hosted within existing processing devices as described herein (e.g., a smart phone or other processor-based apparatus having access to any of the active and/or passive sensing components previously described). As such, it may address an unmet need in terms of understanding cough in a variety of settings, including nocturnal setting.

As previously discussed, such non-contact, "acoustic" type sensing may include sound, ultrasound, infrasound and vibration—related to mechanical waves in air, solids etc. The "passive" acoustic processing described herein may be understood to be digital signal processing and other techniques applied to electrical signals from one or more microphones (where the system "listens" for sounds, and determines if cough, wheeze, splutter, snore, gasp and so forth are present). This may include processing reflections and echoes from other sources. However, what is described previously as "active" processing concerns sensing sounds that can be emitted by the system for motion detection, such as audible or inaudible sounds for sensing. For such sensing sounds in the range approximately 18 kHz to just below 24 kHz, these are achievable with common speakers and microphones in smart devices (smartphones tablets, smart speakers, smart TVs and radios and so forth) that sample at 48 kHz. For higher sampling rates, higher frequencies can be used once the mechanical design of the speaker(s) and mic(s) and enclosure(s) support these configurations. The term SONAR is used to describe such an active system (operating in air mainly) using/generating above about 18 kHz sensing frequencies, (which is a threshold of hearing for most people). Ultrasound may be understood to begin at around 20 kHz (which is above the threshold of hearing). Thus, the system may operate actively by generating sensing sounds so as to include a low frequency ultrasound.

Thus, an example processing device or system of the present technology may provide a computer and audio processing hardware that is readily available such as a device people carry and use daily, and may locate on beside at night such as a smartphone or smart speaker, a smart TV, a smart watch, band, necklace, or patch. An advantage of such a system is that it can operate by executing an application (such as a downloadable application (app)) on any smartdevice (e.g., smartphone or smartspeaker) in any operating system (e.g., Android or Apple)). It may then utilize a microphone (e.g., an integrated one such as a bottom edge located microphone) for complementing the above-mentioned non-contact sensor. The proposed system may operate by implementing a special mode that minimizes phone signal processing. For example, audio samples acquired with a microphone from a CODEC may be processed in frames using a multicore CPU. Typically, no user identifiable audio data is stored in the phone's memory.

An example of such a system can track cough episodes over time, classify each cough event or a series of such events (e.g., "risky" cough(s)), and may recommend a further testing or medical appointment to the user, to facilitate timely and thorough medical assessment. Such a device may help to improve quality of life of users.

The processing device, using an application run by a processor, may implement time-frequency audio signal processing on the real-time audio signal produced by the microphone and/or CODEC. Such a signal may contain information from reflected audio signals (e.g. SONAR signals previously described), as well as sounds from the person being monitored, and background environment.

Optionally, cough detection (such as with a detection module or sub-module) and cough classification (such as with a classification module or sub-module) may be implemented as an additional module to, or receive data from, an active sensing related system/module(s) (e.g., SONAR that uses the loud speaker and same microphone produce signal(s) or RADAR). Thus, cough detection and classification may be combined with—or otherwise influenced by, or provide an influence to: (a) data concerning whether a person is absent/present in the sensing field (e.g., such information may be implemented for rejection of background noise), (b) data concerning sleep state (e.g., whether a cough event relates to recent awakenings), and/or (c) coughing subject isolation (e.g., by considering or comparing a tracked/monitored breathing curve to ensure the detected cough event is properly attributed to a monitored person rather than another (e.g., a bed partner not being tracked/monitored).

Thus, the system may detect and/or classify specific signatures (e.g., cough signatures) relating to respiratory and associated events.

An example analysis of cough(s) may involve (a) detection—either or both of (1) an event (individual cough) and (2) sequence of coughs (such as a spasm of same), and (b) the type of cough (event or sequence) (such as productive or dry). The system may also provide an associative output such as to characterize a cause. For example, the system may determine a probability of the cough(s) being related to any one or more of any particular disease(s) such as COPD, asthma, gastroesophageal reflux disease (GERD), and upper airway cough syndrome, etc. Such an estimate may be generated such as in relation to a computer model that is derived from empirical data including analysis of scored cough types.

The system, such as with an application running on a processing device (e.g., a smartphone), may access different sensors in order to estimate physiological signals relating to respiratory conditions both during sleep stages and during wake. In some instances, the tracking of the signal may be conducted during a detected sleep stage including any one of light sleep, deep sleep and REM sleep. Thus, the sleep stage may be assessed in determining information about a cough (e.g., cough type and/or cause). For example, sneezing would not be expected in REM sleep due to REM atonia. Thus, an incident of cough (rather than sneeze) may be a more likely acoustic event during REM sleep.

Additionally, the system may be configured to detect coughing during the day or at night.

For example, a cough may be characterized as occurring (or starting) in REM sleep (e.g., later in the night) or in deep sleep. Thus, the impact of the cough on sleep architecture may also be detected. For example, the cough may be characterized by the impact it has on detected sleep (e.g., a change in sleep stage). In some cases, particular patterns of wheezing, particularly during expiration, may also be detected. During non-REM sleep, the basal metabolic rate and ventilator drive decreases. For example, the system may be configured to determine sleep scores based on such factors as quality and duration of sleep. Thus, the cough assessment module may evaluate the user's coughing events based on the sleep score. For example, sleep scores may tend to decrease due to coughing (especially where there are frequent coughing fits).

Acoustic analysis can also be applied to estimate the cough frequency, severity, and classify the type of cough. In some cases, such analysis may be applied to detect particular patterns of wheezing, particularly when associated with detected expiration.

Similar determinations may be made during nighttime, as well as daytime, during which coughing may result in experience of subjective and/or objective measures of fatigue and lethargy. These may relate (often in combination) with a seasonal allergy to pollen.

A microphone of the system (e.g., associated with a smartphone or a smart speaker, a smart TV or a smart watch) may further be used to monitor and classify sound patterns consistent with chronic cough or snore, and separate those noises from other background noises such as cooling fans, road noise and the like. In some cases, optionally, low frequency ultrasonic sensing may be applied to detect further information on chest wall and body movement that may be attributable to cough motion(s).

Several methods may be applied by the processing device to detect and classify such cough related signatures.

In one example method, hand crafted features may be empirically determined using standard time, frequency, or time/frequency methods. A classification system may then be implemented by using supervised learning. For example, based on human labeled events from, for example, a PSG (polysomnography) sleep study and acoustic sensing, a classifier system may be derived. Many PSGs already include an audio recording (sometimes in conjunction with video recording) which may be suitable for passive audio acoustic analysis. Ideally, the PSG would also include active analysis, where a low frequency ultrasonic (e.g., above about 18 kHz) is emitted and recorded—such as using SONAR).

Such a classifier system may be based on a linear or quadratic discriminant analysis, or a random forest classification model that improves the performance of an initial decision tree, by generating multiple decisions trees and using majority voting, or a simple neural network with one or more hidden layers, and an output layer. Thus, the trained classifier may then be implemented for cough detection and type identification (etc.) and related output as previously described. Shallow or deep neural networks may also be used for classification.

There are some advantages to this approach, as acoustic features have been explored in detail for voice recognition, and smart device processors may be optimized for such processing (such as calculating FFTs) (smartphones are particular optimized for audio processing, based on their telephone heritage).

The system may be configured to detect the characteristic patterns of snoring, snuffling, coughing or breathing difficulties, such as according to the example processing illustrated in FIG. 8C. Thus, detection may be implemented using techniques such as the following: (i) digitize the microphone(s) signals, (ii) a digital filter bank (an array of band pass filters used to split the signal into sub bands), which are then processed in turn using a one or more of (iii) time domain metrics such as energy level and/or envelope and/or zero and/or kurtosis (particularly useful to identify "burstiness"), which can operate on each sub band from the filter bank, as well as the full bandwidth signal content (iv) time frequency decomposition (such as using wavelets or short time Fourier transform (STFT), a search for 'bursty' noise (e.g., a "cough signature" using spectral analysis) and/or morphologic (such as shape processing applied to a spectrogram), which can operated on each sub band or on the full bandwidth signal. Mel-frequency cepstral coefficients (MFCCs) are calculated, the sub bands may be selected with narrower bands at lower frequencies, and wider bands at higher frequencies. If SONAR is running concurrently, the SONAR frequency band can be excluded from this cough processing, and any associated SONAR harmonics (e.g., an FMCW 18-20 kHz triangular sweep at 16 sweeps per second may introduce a small artefact around 12 kHz which should be accounted for during processing). These candidate coughs events (and possible cough sequences) may optionally be cross correlated with patterns identified in sensed movement and/or respiration data. By using such fiducial aspects of cough sound(s), and their optional relationship with a SONAR derived respiratory signal and movement detection, the system may realize event and sequence and spasm detection. The system, with the aforementioned SDB processing, may separate cough sequences from other modulating sound (audible) events such as SDB, PLM, RLS, and background noise with a strong beat and/or repetition—or indeed from other modulating events as detected by the SONAR based movement and activity estimation sub system.

Significant advantages of the combination of analysis of the sound of the cough, with the related detected breathing waveform may include: (i) increased confidence that cough is actually present (such as by checking for cough in both the audio band as well as SONAR estimates by assessing/determining a correlation between the inhalation and forced exhalation as seen in the waveform with the audible event), (ii) separating coughs of a partner from the main monitored subject, (iii) handling high background audio such as when an elderly person has a TV turned up loud, (iv) rejecting speech and laughter (common confounding effects on cough detection), (v) aiding separation of cough (including types such as whooping, loose, wet [e.g., more than about two tablespoons of expectoration daily], and dry), wheeze, whistle, sneeze and so forth.

The intensity of the cough can be estimated based on the change in respiratory waveform and/or the intensity sound level of the cough audio. When looking at the sound level, extra information about intensity can be gleaned by estimating the sensitivity of the speaker/microphone(s) with a test playback sequence, and/or also by using the estimated range (distance) of the subject from the microphone(s) based on the SONAR. In simpler terms, the system can estimate how loud/strong/intense the first and subsequent coughs are—even if the person moves with respect to the sensing device (or vice versa).

In terms of cough detection parameters, examples of such hand crafted signal processing features may include calculation of spectral content of a signal (e.g., by Fast Fourier transform using either find peak (frequency domain) or time-frequency processing comparable to processing using a discretized wavelet transform, appropriate basis selection, or peak find. The residual low frequency components identified in this process may also (e.g., separately) be processed to determine longer timescale trends. Particular features for subsequent classification may be derived from such processing.

The respiration rate can also be monitored during coughing periods, in order to understand the inter relationship. Worsening cough may show an increased respiration rate versus a personal baseline in non-cough periods, particularly where the person is getting sicker (whether it be the common cold, an exacerbation etc.). Frequent cough at night can also impact sleep quality, and the presence of such coughing can be used to adjust down a sleep score index.

Understanding cough frequency and severity/intensity as well as breathing rate and body motion may also be used as an early predictor of asthma attacks (such as by detecting increased cough sequence duration, increased breathing rate, shallower breathing interspersed with deep breaths).

For further background, a cough can be considered to include an opening of the glottis (the explosive sound), followed by an expiration, followed by a closing of the glottis. Cough could be a singleton (an isolated cough), or a short sequence (a large cough followed quickly by follow-up coughs—a sequence often lasting 5-10 seconds or more. An envelope of the cough sequences (or indeed those very long sequences known as spasms lasting greater than about 5 minutes (>5 mins)) can be calculated. In other words, a cough can also be classified in terms of whether it occurs in spasms (e.g., a spasm is usually considered as continuous coughing for longer than approximately five minutes). A cough can yet further be classified in terms of its productivity, or in other terms whether the cough is dry or wet (e.g., the presence of mucus indicating a productive cough). The expiratory time (e.g., in this system, as detected by one or more of measured parameters based on the audio signal, measured based on the contactless respiratory signal, measured based on movement of the chest) of a productive cough is typically longer than the expiratory time of a dry cough—although it should be noted that there can be wide variation across the population (e.g., machine learning methods such as deep neural networks can be advantageous to adapt to subject specific snoring, or indeed as a subject's cough changes over time from wet to dry or vice versa).

Thus, any one or more of such cough related classifications (e.g., (a) cough; (b) continuous coughing/spasms; (c) productivity (dry or wet—e.g., with mucus, or either with wheezing)) may be derived by a classification of signals from the sensors (active and/or passive) to make the classification, where features from the signals for classification are derived from the active and/or passive streams from the sensors.

Coughs typically last at least 250 msec, with sequences of around 5-10 sec. A dry cough's inspiration and forced expiration can give rise to strong components up to 16 kHz (around the 3 dB point of a low pass filter that might be used to reject SONAR of 18 kHz and above) with most energy from 0.1-4 kHz lasting, for example, 300 msec, then followed short quiet periods followed by partial glottal closures/further parts of the cough sequence, and so forth, with lower intensity components around 1.5 kHz (e.g., "COUGH Cough cough cough COUGH . . . " etc.). These are just examples, as age and gender, BMI etc. can affect these ranges—which is where machine learning applied to large labelled (supervised) or unlabeled (unsupervised) cough related signal data is important. Optionally, a classifier may also take in parameters such as age (child and adult cough may have different parameters for example) and gender.

For example, if a cough occurs at night while the subject is trying to sleep, the cough may be detected by any one or a combination of (a) a disturbance in the breathing signal (e.g., in active SONAR, a notch may be seen in the respiration signal, and/or a deep inspiration followed by a rapid expiration, or in passive respiration analysis, an apparent interference in the spectrogram (particularly the initial the "COUGH" sound), (b) a change in heart rate (typically detected by the system as an increase from baseline heart rate in, for example, the preceding 10 mins, which is sustained for a period of several minutes after the cough, primarily during exhalation), (c) an increase in blood pressure, and (d) a gross (body) motion event (e.g., due to mechanical movement of the chest). Over the night a reduction in the factors of a determined sleep score may be seen, especially if cough spasms occur. Depending on the type of cough that occurs, a pattern of large inspiration followed by large expiration followed by large inspiration may be seen (e.g., an increase of 50% with respect to recent prior breaths). In contrast, other types of cough may be emphasized by a large explosive expiration followed by inspiration breath—large expiratory rise time, plateau, then a recovery breath (or just a large expiration).

The "spikes" induced in the respiratory waveform can result in an increased estimated breathing rate, or in some cases a decreased breathing rate over a short timescale. Therefore, in addition to estimating breathing rate, the waveform may be analyzed by processing local changes in breathing amplitude changes via estimation of the envelope of the breathing signal, and tracking individual parts of the inspiration/expiration waveform morphology (in particular to identify the inhalation and forced expiration, followed by glottal closure).

Thus, the audio processing may include applying short time Fourier transform (STFT) analysis of a sampled audio waveform obtained from an audio sensor, and estimating normalized sub-band power levels thereof. Mel-frequency cepstral coefficients (MFCCs) may be evaluated to distinguish snoring and/or coughing from speech. Spectral flux (analyzing changes between power spectral estimates) may be determined and evaluated to detect the onset of snoring. RMS (root mean square, or the quadratic mean) may be determined and evaluated, such as in conjunction with the STFT power levels and a running median filter, to distinguish cough related sound from background noise.

The use of spectrograms may be preferred for deep learning models, whereas MFCC spectrograms may be better for shallow models.

Signal pre-processing (e.g., of a generated acoustic sound signal) can involve applying a digital bandpass filter, retaining frequency content in the range 100 Hz to 4,000 Hz (or higher). This can be implemented with a direct form FIR filter using a Kaiser window or by other means. The signal may be resampled to a desired frequency such as 8000 Hz such as if storage space limitations is a concern. Optionally, the signal may be companded—for example, by applying a $\mu$-law compressor or similar approach, or with a compander. This can also be managed by other signal processing means, and companding is not necessarily required.

In the frequency domain (such as by using a transformation of the signal output from the pre-processing), features for classification can include sub-band powers in the following sub-bands (in Hz): 0.01-500, 500-1000, 1000-1500, 1500-2000, 2000-2500, and above. For higher sampling rates, higher frequency bands may be considered. The frequency bands can also be split into smaller or larger segments. For example, a specific sub-band below 800 Hz may be considered—i.e., 0-800 Hz (de-meaned, removal of average value in a moving window). Other spectral measures that may be determined for deriving features may be the spectral centroid, and audio processing steps such as 'pitch'— the harmonic product spectrum, spectral flux, spectral spread, spectral autocorrelation coefficients, and/or spectral kurtosis.

In the time domain, features (that may be derived from the signal output from the pre-processing) can include zero crossing rate, auto correlation coefficients, and running amplitude measures. Other approaches are to calculate the short-term energy and short-time zero crossing rate.

In summary, example features that may be derived by the processing device modules for classification may include processing frames (which may be non-overlapping) of audio samples to determine:
Frequency
Temporal—including amplitude (may be used as a surrogate for intensity)
Spectrogram
Wavelet
For an audio sampling rate of 48 kHz with a resolution of 16 or 32 bits, a frame size of, for example, 64 ms equates to 750 samples.

Such frequency (FFT) and/or time/frequency (STFT, Wavelet, spectrogram) features may include any one or more of:
Local peaks (peak find), and ratios of the areas (e.g., by integrating the area around the peak) of dominant peaks to surrounding peaks
Local and global Maxima and any harmonics
Integration of low frequency component(s) (an energy estimate), integration for high frequency component(s), and/or a ratio of such low and high frequency energy estimates, such as a ratio of low to high
Split into multiple bands (e.g., using filter banks), and processing data within each sub-band such as to derive features as otherwise described herein
Mel-frequency cepstral coefficients (MFCCs)—non-linearly spaced filter banks to approximate human hearing
Spectral flux
Spectral centroid
Harmonic product spectrum
Spectral spread
Spectral autocorrelation coefficients
Spectral kurtosis
Linear Predictive Coding (LPC)
Example temporal features may include any one or more of:
RMS (such as to provide an estimate of volume (loudness such as a measure of dB) of each frame)
Zero crossing rate
Envelope (e.g., filtered absolute value of Hilbert transform)
Pitch based on short term auto correlation function
Other techniques of the processing device may include applying a modified Voice activity detection (VAD) process to reject speech, but retain respiratory events. In some versions, the processing device may employ a generic VAD to merely reject low background noise, and retain both speech and respiratory related sounds. Voice recognition is a rapidly advancing field, and commercial cloud connected services can be applied to mask out voice/speech/music such as to allow improved SDB and cough detection.

Longer trains of coughs may be processed to estimate the variance of cough rate (e.g., coughs per time period such as minute or hour) or estimate the modulation of cough rate over groups of coughs (e.g., coughs per a unified sequence or fit), such as to estimate the shape of a coughing fit (e.g., paroxysmal coughing is frequent and violent/intense coughing that can make it hard for a person to breathe).

Where a breathing waveform has been estimated and is available to the processing device, it can determine any one or more further feature(s) therefrom for classification. Such a waveform, and or features, may be derived as described in any of the previously mentioned references, such as PCT/EP2017/073613, PCT/US2014/045814, US-2018-0256069 and US 2014-0163343. For example, any one or more of the following features may be determined and evaluated:
- Inspiration time and depth
- Expiration time and depth
- Inspiration to expiration ratio
- Notches/dip in the breathing signal waveform due to cough (for example)
- Longer term breathing rate (estimate from peak-peak, trough to trough, or zero crossings—or derived from a spectral estimate)

The system can be configured to check (such as a feature for classification) if there is a progression to full, sustained wakefulness related to a spasm of coughing. This pattern may be evident from either or any combination of a contactless sensing signal (e.g., (RF, SONAR, optical), the audio cough signature, and cough repetition rate. Coughs during REM/deep sleep are rare (and even more unlikely in REM as compared to deep sleep), with the majority of coughing occurring during wakefulness. When the system detects a possible cough signature on the audio processing side, if the monitored subject is determined to be in deep sleep or REM sleep, then the cough signature may be assigned a reduced probability of in fact being a cough.

Of course, REM detection based on respiration may be impacted by long sequences/spasms of coughing. As background, a respiratory and movement based sleep staging system as used in this system is capable of estimating individual movement events' magnitude and duration as well as each breathing movement's amplitude and duration. The algorithm combines high resolution estimations of these parameters into 30 s epoch features which are then evaluated to map the bio-motion signals to different sleep stages. Bed presence is detected through an increase in the received signal power. User wakefulness (W) is associated with higher levels and longer duration of detected movement, and a higher degree of respiration rate variability. Rapid Eye Movement sleep (REM) is associated with the highest variability of detected respiratory parameters, while Light sleep (intended to correspond to N1 and N2) and Deep sleep (corresponding to N3) trend to increasing stability of the detected metrics.

Such sleep related factor(s) can also be implemented to augment the detection of a cough from another subject. For example, sound detected by a microphone or other acoustic sensor may be determined to have come from a bed partner if the monitored subject determined to be in deep or REM sleep based on a sleep stage determination such as from a non-contact sensor based sleep staging module. However, if the non-monitored bed partner has a spasm of coughing, this can lead to awakening of the monitored subject. In such a case, the respiratory waveform as detected via the non-contact sensing may be evaluated to verify the cough source (e.g., the monitored subject, a bed partner), using the processing logic, for instance by detecting, that an arousal followed by a cough is significantly more common than a cough during sleep followed by arousal. In the detection of the first instance, the system may determine that the cough is attributable to the monitored subject and in the second instance the system may determine that the cough is otherwise attributable.

As the incidence of cough increases during the night, the monitored subject's sleep score may decrease. During daytime, recent activity levels and previous daytime and last night's cough scores can be used as an input into a risk categorisation of an exercise induced event (e.g., an asthma attack or a COPD exacerbation) which may be heightened with such input. Analysis of a reduction in sleep score due to cough (with wakefulness) or snoring, along with a rise in resting breathing rate and/or change in inspiration/expiration ratio can be indicative of a worsening respiratory infection, and in turn an increased risk of the subject's condition worsening, such as from an exercise induced event. In other words, as a user becomes more breathless at night and during the day, this is seen in both changes in respiratory (including cough) parameters, as well as reduced activity/ mobility as the person becomes more uncomfortable.

Monitoring the length and the severity of the cough at night time, provides a feedback that allows the beneficial effect (or otherwise) of any proposed treatment to be quantified. The patient may be offered various exercise regimes, treatments or proposed changes (pharmaceutical (adjusted quantity of given medicine), behavioral (breathing deep, avoiding cold air etc.) or others). A deterioration of the patient's cough at night and/or day time, may indicate that the proposed treatment needs to be adjusted or cancelled. Various parameters can be used to estimate the deteriorating cough of the patient, such as the total duration of cough through the night, the number of cough spasms, the severity of each spasm etc. The quantitative criteria for "deterioration" may be more stringent from that of "improvement". Also, the quantitative criteria for "deterioration" may be adjustable to become more stringent the worse the patient health and or cough is.

In a bedroom environment, a processing device may generate recommendations on suitable sleeping conditions—such as both in terms of optimizing sleep quality, as well as to reduce the risk of cough, and ultimately exacerbation. This may be done by monitoring and/or controlling any one or combination of air temperature, humidity, and air quality. The available parameters may be controlled automatically via a building, air handling or local humidifier and/or air conditioning/heating unit with a suitable controller(s) or control apparatus such as in conjunction with the processing device. During the day when the bedroom is empty, these systems may be set with the controller(s) to provide an increase in airflow and automatically open vents/ blinds in order to reduce humidity and freshen the room. Such setting and/or control may be based on the processing device detecting cough event(s) and/or types as described herein.

The system can also manage (e.g., with a reminder process or module) the length of time that bedclothes (e.g. sheets, blankets, etc.) have been on the bed (e.g., remind the user to wash bedding weekly, or automatically send an alert to nursing or other care staff), as well as provide recommendations as to the temperature at which to wash them (e.g., to reduce dust mites, germs, etc.) or other recommendations (e.g., adding an extra laundry detergent at lower temperatures, or washing at 60° C. where supported by the bed clothes). The room can also be warmed up to a suitable sleeping temperature automatically when coming close to bed time. The system may also provide specific feedback advice to a user, such as to adjust humidity in the room based on measurements taken and/or local weather pattern analysis. Control of such adjustments may also be based on the processing device detecting cough event(s) and/or types as described herein.

As an alternative to descriptive and predictive supervised machine learning with hand crafted features, it is possible to implement another form of machine learning known as deep learning. This typically relies on a larger amount of scored (labeled) data (such as many hundreds of nights of scored sleep data and/or daytime data with cough). This approach may implement many interconnected layers of neurons to form a neural network ("deeper" than a simple neural network), such that more and more complex features are "learned" by each layer. Machine Learning can use many more variables than hand crafted features by humans.

Convolutional neural networks (CNNs) are used widely in image processing for inferring information—such as for face recognition, and can perform very well in this context (may assume all inputs are independent from each other—such as a pixel being from one object). These can also be applied to audio spectrograms, but do suffer from the fact that an observed frequency in a spectrogram may belong to many accumulated sounds—or indeed complex constructive and destructive interference (e.g., phase cancellation). The system may also, where possible, also evaluate the periodicity of the audio. In effect, the system cognitively "learns" temporal properties from intensity, spectral, and statistical estimates of digitized audio from the recording device. The representation is not speech—rather different respiratory issues (but can benefit from speech and acoustic processing found in modern smart devices).

In contrast to CNNs, not all problems can be represented as one with fixed-length inputs and outputs. For example, processing respiratory sounds has similarities with speech recognition and time series prediction—and thus can benefit from a system to store and use context information such as Recurrent neural networks (RNNs) that can take the previous output or hidden states as inputs. In other words, they may be multilayered neural networks that can store information in context nodes. RNNs allow for processing of variable length inputs and outputs by maintaining state information across time steps, and may include LSTMs (long short term memories—types of "neurons" to enable RNNs increased control over) to manage the vanishing gradient problem and/or by using gradient clipping.

In summary, the core processing, such as in one or more modules of the processing device (or with one or more processors in communication with the processing device) can include any one or more of:
  Ultrasonic detection of breathing and movement. This can use frequencies of about 15-20 or higher kHz
  Audio detection and classification of respiratory events, using microphone detecting in the standard audible frequencies of 100 Hz to 5 kHz or higher. This audio processing can be fused with the breathing pattern and movement derived from ultrasonic detection
  Optionally track activity and steps during the day using the smartphone accelerometer and/or gyroscope or other motion or other sensors (PPG) or services and optionally associate activity or step counts or changes in activity or step counts with cough event/type
  Personalized AI insights using machine learned features, and deep learning applied to large field datasets Thus, such processing may be implemented, for detection of different types of cough, gasp and wheeze in bed when awake (particularly after bed entry, and after waking up in morning, as the change in body position can exacerbate the cough), based on acoustic/sound processing and/or motion processing such as from SONAR and/or RADAR sensing. Thus, coughing may be classified in relation to a detected body position such as a change in body position—e.g., to check if cough subsides when in the prone vs. supine position (or vice versa)

This detection may also be implemented in association with a sleep staging system that determines/indicates that the person is asleep. Thus, the system may evaluate such sleep related information, such as the one previously discussed, for detection of cough.

Additionally, such a system may also be implemented for cough detection in a more mobile or passive arrangement without the use of active SONAR and its use of a speaker, such as to detect cough when a person is on the move, using only the microphone (for example, if the processing device, such as by the user control, has activated the microphone related sound sensing) while the mobile processing device is moving (i.e., not in a stationary location such as on a bedside table).

Where both active (e.g. ultrasonic) and passive detection are available (such as in a bedroom or in a vehicle), the processing device may measure/detect the biometrics of a specific user (a monitored person). For example, such biometrics may be determined from sensed motion signals as described in International Patent Application No. PCT/EP2016/058789, the entire disclosure of which is incorporated herein by reference. With such determined biometrics, a detected cough may be associated with the monitored person. For example, if a bed partner coughs, it is possible to exclude such an acoustic event from influencing cough metrics of the monitored person that is determined by the processing device.

Where both accelerometer (and/or gyroscope) and passive detection can be implemented and made available (such as during daytime activities when the phone is in a pocket), the processing device may then associate a cough (a detected acoustic cough event/type) to the person (and not to another person or other background noise) by evaluating a motion signal from the accelerometer of the phone in the pocket that detect the chest movement associated with the cough such as by evaluating a time correlation of the sound (cough sounds) with necessarily associated motion (cough related chest/body movements).

One useful feature is relating cough intensity (which may be a parameter based on the loudness and duration, which may be corrected (e.g., an adjustment or normalization) for range, if distance metrics are available from SONAR) and frequency (as well as sequences, trains, spasms of same) to changes in breathing rate over a longer timescale, and thus estimating the risk of asthma or COPD exacerbation based on a personalised estimated snore metrics.

Other aspects are the detection wheezing, a dry "hacking" cough signature, and so forth. It is also possible to detect chronic cough with (e.g., extra "tones" in the spectrogram in the range of 0.1-15) and without wheezing episodes.

It can be seen that by detecting sleep staging, snoring, and cough, the processing device can relate such events to difficulty in sleeping, i.e., either coughing or other restlessness or snore.

Analysis of cough parameters over many days and nights can also give insight into potential asthma, as coughing caused by asthma may be worse at night. For example, the presence of productive cough may increase risk of a COPD exacerbation.

For managing and/or assessing COPD condition, the processing device can detect breathlessness (shallower breathing) such as by evaluating changes in inspiration/expiration ratio (air flow limitation during the expiratory phase which in airway obstructive disease causes prolonged expiration—one of the indications of COPD), and increase in respiration rate, changes in longer term respiration rate variability as assessed via modulation over a longer timescale (for example, intra or inter night variation). This may be considered in relation to (such as by comparison) population normative values, as well as compared to a personal baseline(s) value(s)). For such COPD assessment, the processing device may also detect and evaluate increase in cough severity (repetition rate, intensity, duration etc.) for indication of a change in COPD condition.

A system of two processing devices (e.g., two smartphones or a smart phone and smart speaking in the room can be implemented to separate cough from near and far users. These devices may communicate parameters (e.g., cough related parameters) over a network—such as an Internet or the Internet or short range wireless such as Bluetooth, Wi-Fi etc., such as to help to attribute a cough event(s) with a particular person being monitored.

As previously described, the processing device may track inspiration and expiration waveform using the active and/or the passive acoustic processing.

The acoustics processing is designed to be able to handle noisy environments such as when TV, tablets, or other smartphone audio is in use (phone/video call), speech, road noise etc. For example, the processing device may filter out its acoustic signal to remove frequencies associated with such sounds.

Depending on the type of neural network used, local phone artificial intelligence (AI) acceleration may be available to reduce power consumption (and may benefit CNN type approaches such as typically used for image processing, or RNNs more commonly used for audio processing).

In some cases, the processing device may control or provide output related to medication use. For example, it may provide an indication as to whether the user is being helped by cough suppressants, antibiotics or not, such as by comparing cough related data prior to use of such medication relative to similar data for the period after/during use of such medication. Such medication use information/data may be entered into the processing device to provide the time of use, quantity of medicine, medicine brand etc. correlation. The processing device may then further characterize or provide an indication of any change in the nature of the cough and whether it is alleviated by the medication or not. Furthermore, such coughing events may be used to identify whether or not they respond (change) in relation to use of other non-cough medications, such as asthma medication). If so, such coughs may be identified as asthma related cough or not. Similarly, if such detected cough events remain after the user has stopped taking the medication (such as after asthma medication and/or suppressants or antibiotics). Such persistent coughs may be identified by the system with a warning to further consider such as in relation to other medical issue—such as lung cancer related cough.

The technology enables rich and detailed chronic disease screening, analysis, and management such as on a consumer/patient's smartphone or smart speaker—without inquiring the purchase of other hardware. The patient may be empowered, such as by a simple downloaded application, to understand and to some extent, manage their health, using a smart app that enables new sensing functionality to obtain health data insights on their smart device, and optionally through connected (processing assistance) via cloud software services.

An example of such a system of in relation to the cough assessment module 8833 of FIG. 8A may be further considered in relation to the processing modules of FIG. 8B. Such modules may be included in the system of FIG. 8A or 8B or implemented separately. The system may include an active sensing module 8902 and a passive sensing module 8904. The active sensing module may generate SONAR based sensing signals via a speaker(s) and receive reflected versions via a microphone(s) and perform demodulation (e.g., mixing) for generating raw motion signal(s). The passive analysis may perform filtering and/or other and signal conditioning (e.g., pre-processing). The system may include sleep staging processing module 8906, such as for signal extraction and feature extraction. In the assessment module 8908, from the active stream, respiration rate, signal quality and movement/activity counts may be determined on an epoch basis with the raw motion signal. Similar generation of such signals/parameters may be derived in the process/module 8912 from the passive stream. Signal quality of both may be implemented to weight the features, since one or the other processing stream may be affected differently by nose/interference/external movements etc. Features such as for snore classification and/or fingerprinting (e.g., cough signatures) may be derived in the feature extraction process/module 8914 from the passive signal stream. Machine learned features may also be extracted for such classifications in the module 8916. Thus, with such features a snore classification process/module 8920 and a cough related fingerprinting process/module 8918 may classify the passive stream respectively to produce outputs 8928 such as cough events, snore, wheeze, gasp etc. The module 8910 may process parameters form the module 8908 and the raw motion signal from the active stream processing at 8902, to determine respiratory effort, such as a respiratory effort signal. With such a signal and sleep staging information from sleep staging process/module 8906, SDB assessment process/module 8922 may determine SDB related output such as by classification, such as in the manner previously described. With such assessment, including sleep staging information, sleep stages may be output a process/module 8924 and sleep scoring may be output at process/module 8926. Additional output features in 8928 may be output based on the SDB assessment, such as AHI, SDB events, signal quality, etc.

Example of Snore Detection

One approach to implementing a snore detector is to consider real-time or near real-time processing (such as updating features twice a second) and/or at the end of a night/end of session in "offline" operations such as post processing, which may include a snore classification process. "Offline" in this case may be understood to indicate that the data is processed at some delayed point of time (e.g., after a sleeping session). Whereas, an "online" process may be understood to concern real-time or near-real time processing. The fact that the data does not have to be processed in real or near real time permits a transmission of data to a remote server (or other cloud computing apparatus) to implement use of more or greater processing power. This facilitates processing of more data over a longer periods of time, which may also allow for the identification of long term trends in the data. Examples of the present technology may implement either or both of such online and offline processing methodologies using local and/or remote processing.

For example, the near real-time snore processing may include filtering (such as noise reduction and/or removing an active SONAR waveform—e.g., low pass filtering to remove components above say 17 kHz—such as an FIR anti-aliasing filter, and/or notch filtering to remove mains electricity hum at 50 Hz or 60 Hz [depending on local regional mains frequency]) and down-sampling (to reduce data rates and processing requirements—e.g., resampling 48 kHz audio to 16 kHz audio). The notch (such as IIR) or other adaptive filtering is useful to suppress artifacts that can be introduced if a smart device such as a cell phone is charging while recording audio, as the charging cycles can introduce audio artifacts.

For example, the audio classification module for snore may calculate any one or more of the following three outputs (e.g., metrics):

The probability of snore for a given second [pSnore]. Such a probability may be calculated as described in more detail herein. This can be calculated by a neural network (such as deep neural network DNN, a convolution neural network (CNN), a recurrent neural network (RNN) etc.). The value may be used for processing and also may be displayed as a snore indicator.

The root mean square (RMS) of the audio signal for a given second [audioRms] (e.g., the input audio can be normalised by the RMS of the current second) This may represent an estimate of the signal strength.

A summary value of a given second used for outputting a representation of the audio [audioRepRaw]. This may be a relative intensity metric that can be used to plot a relative amplitude of the signal. The summary metric provides shape for the audio signal in the plot of FIG. 36. These metric outputs may be evaluated by the offline classification module to form the additional outputs of the snore detector (See, e.g., snore related output of the user interface of FIGS. 34 to 36). For example, a total snore time may be determined and "snore snippets" may be displayed in the user interface example of FIG. 36 from the classification. As shown, each of a plurality of the audio signal snippets or sub-segments of the larger audio session, which may be chosen for display based on the classification, may be plotted in proximity to a play button (See play arrow symbols of FIG. 36) on the user interface to permit playback of the associated audio signal with a speaker(s) of the apparatus that presents the user interface.

For example, the processing may include, for example, calculating Mel Frequency Cepstrum Coeficients MFCCs, and then using a CNN or RNN model (such as implemented in a machine learning platform (e.g., Tensorflow)) to estimate the probability of snore at a particular frequency (e.g., 2 Hz), and estimate a relative intensity of snoring at for example, another frequency (e.g., 1 Hz). An averaged RMS may also be calculated for display purposes, e.g., an approximate representation of intensity of snoring such as in a graph. Such a graph is illustrated in the snippets of FIG. 36. The system may also mark or select periods of high probability and/or high intensity snore for user playback (See, e.g., FIG. 36).

In one example, MFCCs may be calculated from the filtered audio (e.g., 16 kHz); e.g., 15 MFCC calculated for every 25 ms of audio, with a step of 10 ms, leaving 98 sections to calculate the MFCCs. To remove a DC component from the MFCCs the first MFCC can be deleted. This leaves the size of the final MFCC matrix for a given second at 14×98.

In one realisation, a Tensorflow module (or some other realisation of an AI model that has been trained on a large labelled dataset of snore and non-snore audio) is called twice each second to provide a 2 Hz output. This is done to reduce errors when a snore starts near the end of the current window. In order to call the model twice, a portion of each previous call to the process (e.g., the last half a second's worth of MFCCs) is retained in the memory of the process representing its state. The model is then called twice: (i) the half second of MFCCs in the state and the first half second of current MFCCs, and (ii) the full second of current MFCCs. The last half second of the current MFCCs are then stored in the state to be used in the next function call to the module. Before each call to the Tensor flow module the MFCCs are unwrapped to a vector of length 1372. This vector is then scaled before the call. Each call to the Tensor Flow module produces a single output pSnore value, which is stored for use and/or output. Thus, for a session of audio, the processing (which may be local and/or remote, online or offline) may be implemented to produce a time series of pSnore values associated with times of the audio signal.

An example offline version of a Snore Classifier may be used to post process the data collected from the Snore Audio Classification model (e.g., using the pSnore values) and calculate the outputs for snore that may be shown in a user interface. During the session, or group of sessions (if there are more than one session during a night), the Offline Snore classifier may be implemented to generate additional output(s) (e.g., four), such as in an application programming interface API format, for the end user, including any one, more or all of: (i) Total Snore Duration[SnoreDuration]—a count of the total amount of time a user spent snoring, such as during a particular sleep session or a group of sessions (e.g., a night of sleep with several interruptions during the night) (ii) snore Flag[snoreFlag]—a binary flag indicating when the user was snoring, (iii) Snore Event Time [snoreSnips]—a list of times the user was snoring that can be used for audio playback, (iv) Audio Display Signal [SnoreDispSig]—a simple representation of the amplitude of the recorded audio signal at each second (e.g., an amplitude metric based on the standard deviation of the signal). (such as for user interface (UI) purposes).

The snore classifier algorithm may perform any of the following processing operations: (i) post process the pSnore value, (ii) threshold pSnore to create Snore Flag, (iii) Snore Event Times Detector, (iv) block the Snore Flag into chunks (e.g., 5 minute chunks), and/or (v) post process the Audio Display Signal. Each of these operations is described in more detail in the following text.

Figure 38:
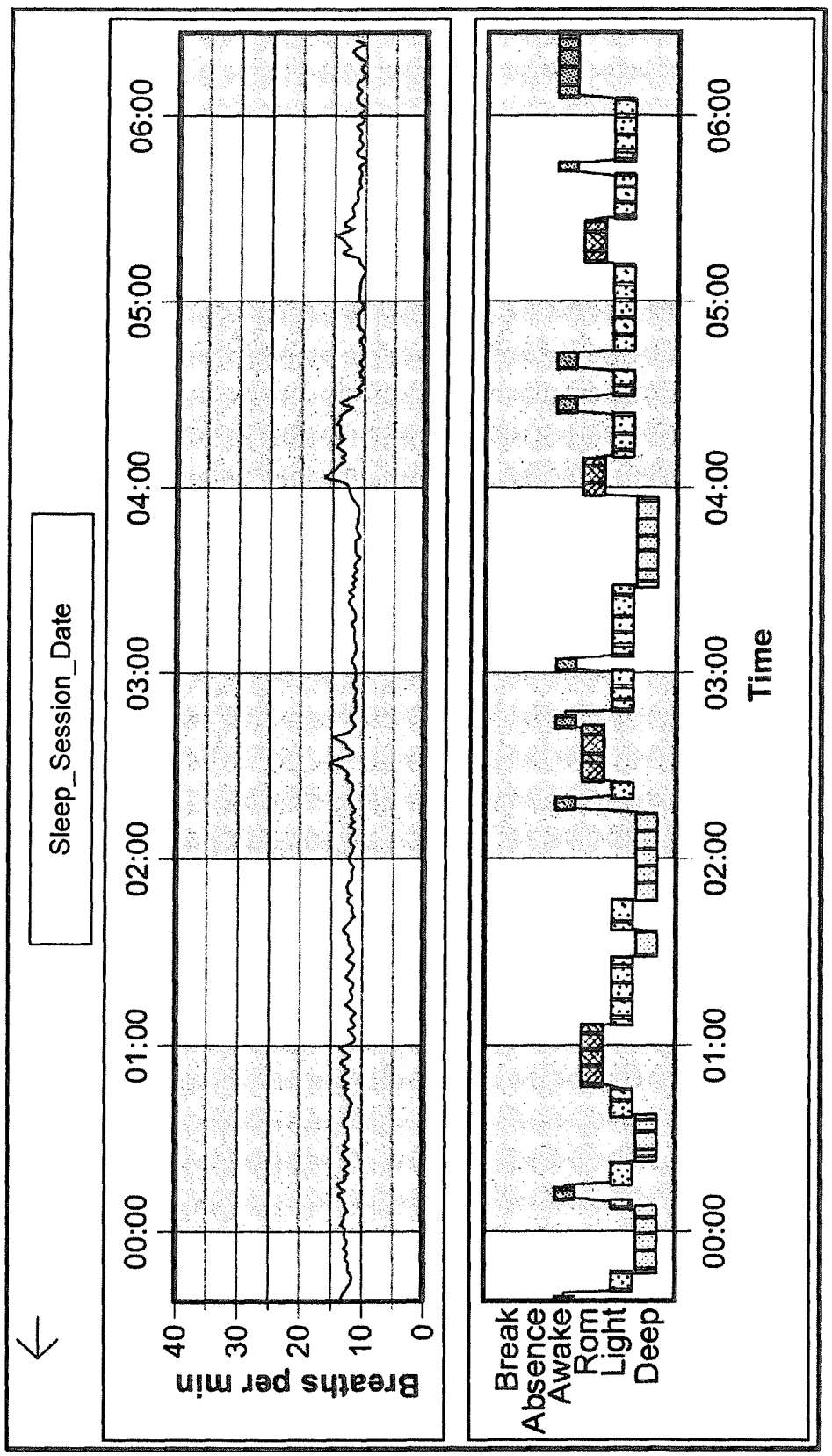

(i) Post process the pSnore value: As described, the pSnore looks at a short term of the audio signal (e.g., only a given second) and does not represent knowledge of longer term trends in the data. Therefore, it is useful to post process the pSnore into a single feature that is more robust to interference. A logistic regression model with, for example, a plurality of input features (e.g., 3) can be implemented. This model may take in two features derived from the pSnore and another from the audio RMS. The first of the two pSnore based features may be a percentile filtered version of the pSnore with different window lengths. This is performed to assess the level of snoring over larger windows of time, as pSnore typically evaluates short term data (e.g., a second of data). The other feature is a signal quality based feature derived from an estimation of the breathing rate, between for example 5 and 35 BPM, which is in turn, derived from the audio RMS. A display of the breathing rate over time in a signal is illustrated in FIG. 38 on a common time scale as a sleep hypnogram. This feature increases robustness to non-periodic noise sources that are non-snore, but might otherwise confound the neural network. The output of the model is a value of the measure of snoring likelihood (hereinafter pSnoreFilt) and may be used internally by the following operations of the module.

(ii) Thresholding to create snoreFlag: For this analysis, a snore flag (e.g., generated repeatedly such as at a 2 Hz frequency) is created by thresholding the pSnoreFilt from the previous processing. This processing may also use the sleep hypnogram to blank out sections of detected snoring where a sleep staging algorithm has provided more than a certain amount of (e.g., three minutes) of absence, wake or break state. In other words, the system may recognize that the detected snoring is not from the monitored user because the sleep system has already recognized that the monitored person is awake, absent or otherwise breaking from sleep. This evaluation can be helpful to reject sounds of a bed partner snoring, when the system is designed to detect the nearest person's sleep and snoring only.

(iii) Detector (of) Snore event times/sections: In order to provide the user with a number of audio sections of snoring to listen to the algorithm detects up to the certain number (e.g., 5) most likely snoring events and provides a time stamp for the beginning and end of each audio section. Each section has a maximum length of (e.g., one minute). This example is illustrated with the "snippits" of FIG. 36. The snore Sections or snippits are taken from sections when the pSnoreFilt is equal or greater than a threshold. This threshold may be significantly higher than the threshold used to calculate a percentage of snoring for the night more generally. If there are less than the maximum number of sections available, then the algorithm may report as many as are available. For example, given a recording with very little snore, a user may only get three snore sections from the algorithm. The pSnoreFilt is set to zero wherever the snore flag is not set. Averages of the pSnoreFilt values may be determined across a sliding window (e.g., 60 seconds) before identifying the highest peaks in the pSnoreFilt at a minimum spacing of 5 minutes. The algorithm then selects up to the top valid peaks (e.g., five) and returns a window+/− 30 seconds for each of the audio snippets.

(iv) Block the snoreFlag into chunks: In one realisation, snore status may be reported in a more granular form such as the outputs being provided in chunks on an order of minutes (e.g., 5 minutes). As a result, before outputting the final snore flag to the user, the higher frequency (e.g. 2 Hz) snore flag is blocked into chunks (e.g., each a five-minute-long chunk). If more than 50% of a five-minute block of snore flags has been flagged as snore (considering the higher frequency (2 Hz) snore flags) then the whole chunk is marked as snore. The output snore flag from this process is then up sampled to display in epochs of thirty seconds (30 s). This final snore flag can be provided as an API output. The total snore duration output is calculated from this longer term Snore Flag.

(v) Post process the Audio Display Signal: A final section of the Offline snore detector is a brief post processing of the Audio Display Signal. A standard deviation filter with a five-minute window is applied to the whole display signal, before it is normalised between 0 and 1. The output of this section is the final Audio Display Signal. An example of this audio signal is shown as the graph in the middle panel of the user interface display of FIG. 36.

Estimating Flow Limitation/Respiratory-Effort:

It is possible to estimate flow limitation based on the estimates of respiratory effort, using RF, SONAR, and/or passive acoustic analysis. Specifically, this involves a process that estimates of the presence or degree of flow limitation (or some other respiration effort metric) using such sensing technology. An example may output a flag or index (either absolute or relative) indicating flow limitation/respiration-effort.

Flow Limitation (FL):
  Can occur when the rise in oesophageal pressure is not accompanied by a flow increase, and is a non-invasive assessment of residual upper-airway flow limitation
  is associated with negative health outcomes and can disrupt sleep
  can occur for prolonged periods i.e. it might not be associated with apnea/hypopnea/desaturation events
  may be useful in monitoring COPD (expiratory FL)
  typically manifests as a flattening of the flow signal morphology An example processing approach to estimating flow limitation/effort using passive acoustic processing can include:
  Time/frequency methods such as CNN on spectrogram/MFCCs, cepstrum, Short Time Fourier Transform (STFT);

The approach to estimating flow limitation/effort using active SONAR, RF, Light Detection and Ranging (LIDAR), other optical approaches may include:
  Inferring from biomotion signal morphologies (fiducial point analysis, skew, kurtosis, area of parts of breath etc.)
  This would typically be looking for metrics that describe some sort of flattening of the waveform (accounting for CW/FMCW distortions where appropriate)
  Can use Doppler Radar to infer inspiration/expiration part of breathing cycle (where available)

The approach to estimating flow limitation/effort using passive acoustics and active SONAR, RF, LIDAR, other optical approaches may include:
  Use the passive and active features together can provide a synergistic improvement to non-contact sensing modalities such as by adding confidence, as well as permitting capture of different types of flow limitation. For example, a flow limitation may correspond with less severe detection thresholds than full obstructive events, so the different sensing techniques may permit use of different detection thresholds.

These estimates can be combined with wake/activity measures to estimate respiratory effort related arousals (RE-RAs). One potential use case is to recommend a different therapy (e.g., an MRD) for a cohort with low/mild AHI but flow limitations. It may also be implemented as part of sleep-score penalisation (e.g., a SleepScore is reduced based on the number of flow limitation events and/or time period).

The processing can also estimate the location/type of obstruction by analysing the characteristic of the audio signal.

Separating Obstructive, Central, and Hypopnea Events

The following background to events may serve as guidelines to event classification:

(a) Apnea may be considered: a drop in peak signal excursion by ≥90% (optionally plus or minus 5% or 10%) of pre-event baseline for ≥10 seconds (optionally plus or minus 2 seconds) using an oronasal thermal signal, PAP device flow, or an alternative apnea sensor. No requirement for a desaturation or an arousal.

(b) Obstructive apnea may be considered: the aforementioned apnea (a) where respiratory effort persists when breathing cessation starts (also, paradoxical breathing possible throughout breathing cessation);

(c) Central apnea may be considered: the aforementioned apnea (a) where respiratory effort is absent.

(d) Hypopnea may be considered: a drop in peak signal excursion by ≥30% of pre-event baseline for ≥10 seconds using nasal pressure, PAP device flow, or an alternative hypopnea sensor, AND there is a ≥3% oxygen desaturation from the pre-event baseline OR the event is associated with an arousal. The system may assess for: (i) Snoring during the event, (ii) increased inspiratory flattening of the flow signal compared to baseline, (iii) thoracoabdominal paradox that occurs during the event.

(e) Obstructive hypopnea may be considered: the hypopnea (d) where—if any one of (i), (ii) or (iii) are assessed to be present (f) Central hypopnea may be considered: the hypopnea (d)—if none of (i), (ii) or (iii) are assessed to be present (i.e., (i), (ii) and (iii) are absent;

(g) Cheyne-Stokes Breathing may be considered: Episodes of >=3 consecutive central apneas and/or hypopneas separated by a crescendo/decrescendo change in breathing amplitude with a cycle length of >=40 seconds, AND there are >=5 central apneas and/or central hypopneas per hour of sleep associated with the crescendo/decrescendo breathing pattern recorded over >=2 hours of monitoring.

Manifestation of obstructive apneas in the active and passive data analysis:

Obstructive apneas may be classified using merely the passive acoustic stream, as such events may be represented as sustained periods of silence near in time to intense snoring. The periodicity of events can be exploited for detection. This signature is quite clear for severe cases, and has a different signature for moderate events where snoring, gasping sounds can exist during the actual event.

The most distinctive feature for the active signal (e.g., SONAR, RF, optical etc.) with respect to obstructive apneas is the amplitude drop. For example, many events exhibit continuous respiratory effort (e.g., respiratory motion) through the apnea event.

The active signals can be extracted employing principal component analysis techniques in combining the range bins. This can be complemented by the detection of characteristic snoring, gasping sounds which can be extracted from the passive signal. The classification system may output sleep apnea classification to grade moderate or severe obstructive sleep apnea (OSA) such as by assessing a count of events. For example, moderate OSA may be identified for subjects with AHI in a range of about fifteen to thrifty events (optionally plus or minus two or three events at either or both of the range limits). Similarly, severe OSA may be identified for subjects with AHI in above the moderate range (e.g., above thirty events (optionally plus or minus two or three events). FIGS. 18 to 21 illustrate graphic displays of signals of passive and active sensing in a classification of moderate OSA, primarily based on obstructive apnea events, on a common time scale showing indications (see lower graph panel) of the classified events (e.g., obstructive apnea, mixed obstructive/central apnea, central apnea, and hypopnea). FIGS. 22 to 25 illustrate graphic displays of signals of passive and active sensing in a classification of severe OSA, primarily based on obstructive apnea events, on a common time scale showing indications (see lower graph panel) of the classified events (e.g., obstructive apnea, mixed obstructive/central apnea, central apnea, and hypopnea). An example benefit of a synergy of the passive and active sensing techniques described herein may be considered with reference to FIG. 24. While the motion signal of the top active sensing panel might, in isolation, be misinterpreted as an absence of effort at certain times (e.g., between the amplitude variations), which might confound a system so as to suggest a central apnea, when combined with data of the passive sensing in the middle panel, such signals may be more accurately classified to reflect obstructive apnea events, as indicated in the lower panel.

Figure 31:
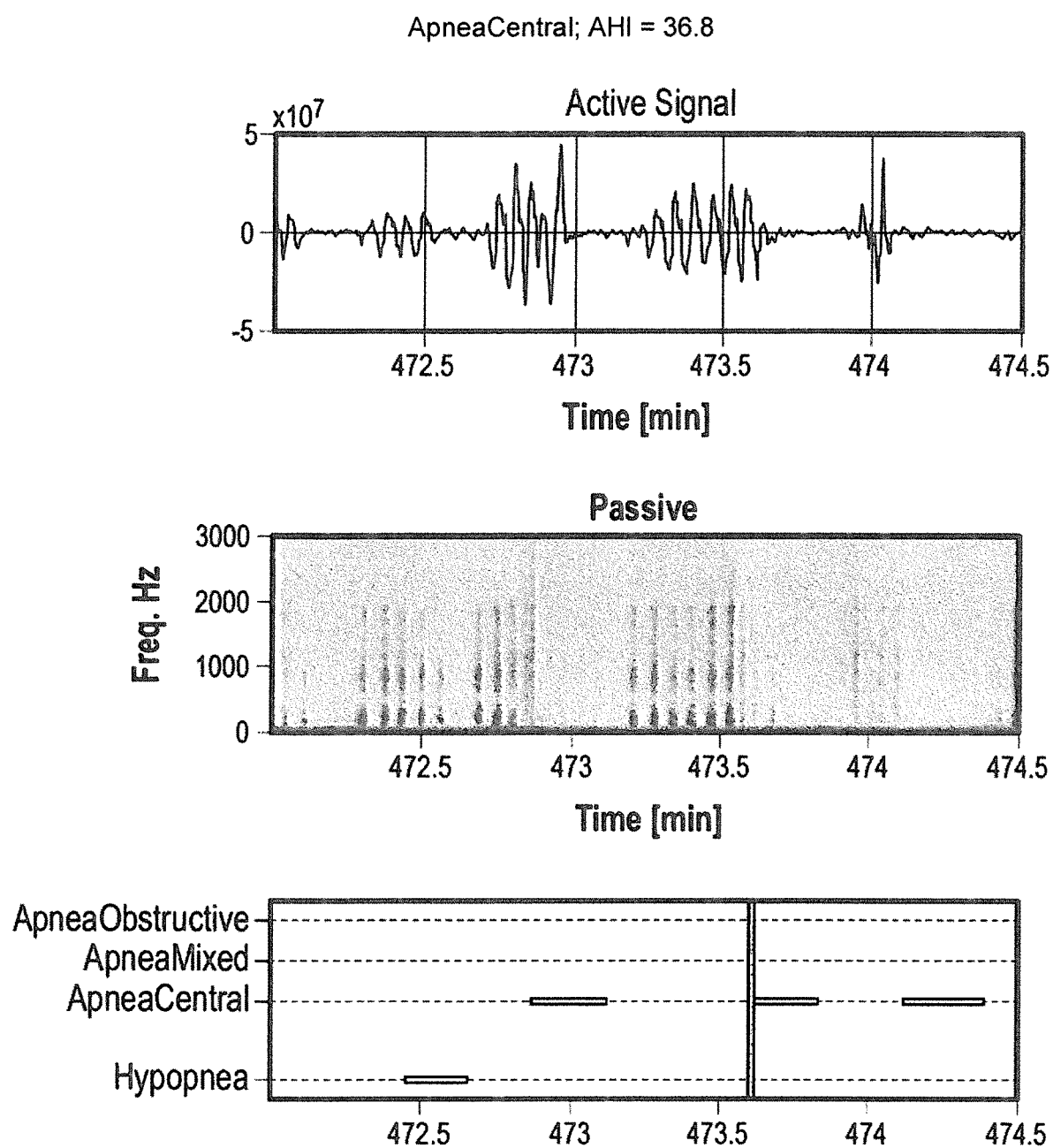

Manifestation of Central Apneas in the Data:

The most distinctive characteristic of central apnea is the lack of respiratory effort during apnea visible in the active signals. Many examples do not exhibit snoring. However the signature of gasping/loud breathing can be detected from spectrograms. This can be complemented by confirming the gasping/loud breathing from the passive signal. Classification of central apneas can be achieved by leveraging the active signal in conjunction with lack of irregular snoring in the passive signal. In certain rarer cases, loud, regular snoring can be detected before the actual central apnea event (e.g., training cases may be provided to a deep neural network or rulesets may be employed to permit classification of both cases). FIGS. 26 to 30 illustrate graphic displays of signals of passive and active sensing in a classification of moderate OSA, primarily based on central apnea events, on a common time scale showing indications (see lower graph panel) of the classified events (e.g., obstructive apnea, mixed obstructive/central apnea, central apnea, and hypopnea). FIG. 31 illustrates a graphic display of signals of passive and active sensing in a classification of severe OSA, primarily based on central apnea events, on a common time scale showing indications (see lower graph panel) of the classified events (e.g., obstructive apnea, mixed obstructive/central apnea, central apnea, and hypopnea).

Figure 32:
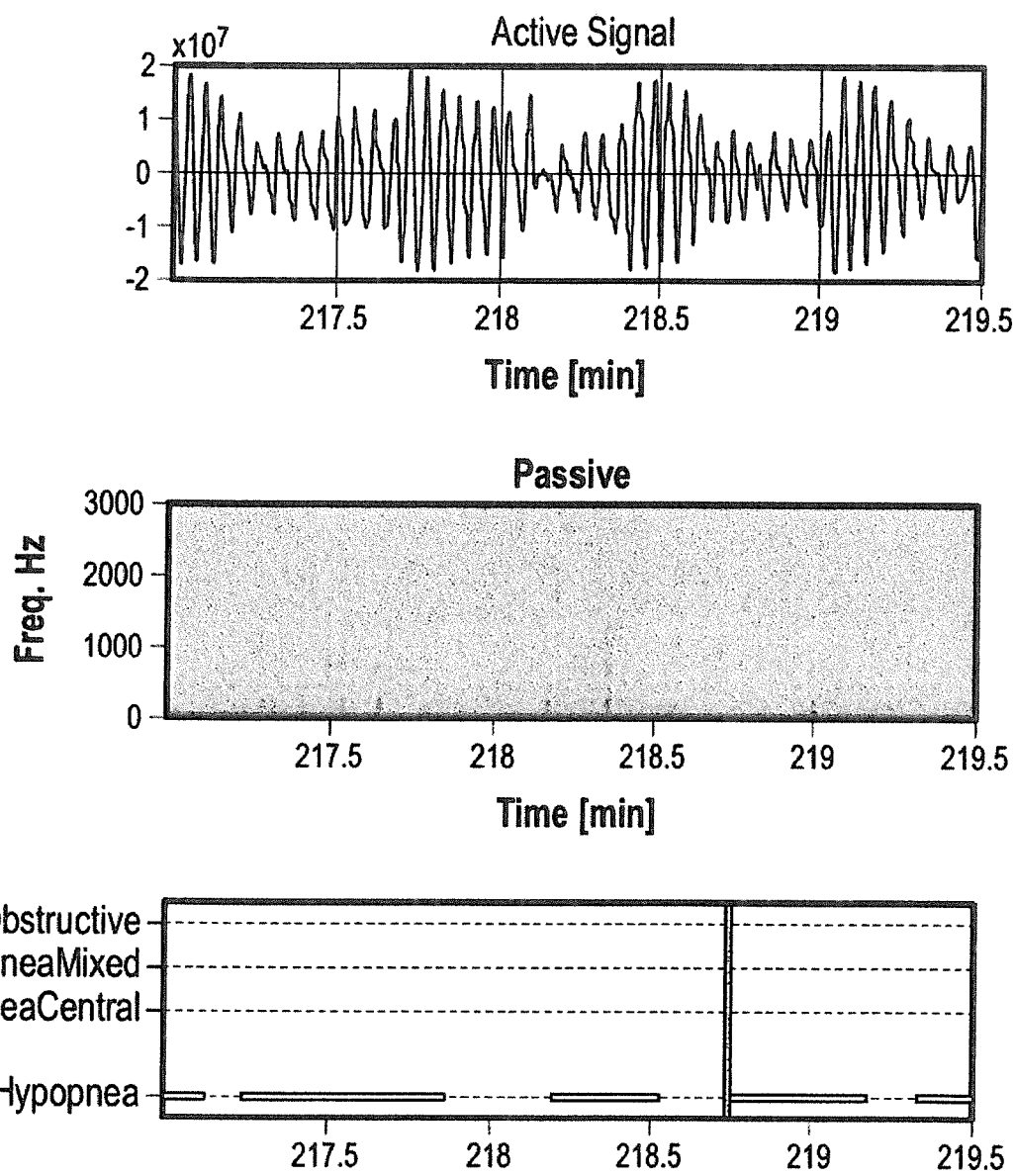

Manifestation of Hypopneas in the Data:

Hypopneas can be more difficult to classify using the passive signal alone. In this section, examples of hypopnea events for one severe subject are shown. For example, visual examples of a sequence of hypopneas with no clear signature in the passive stream, whereas in another example, snoring/loud breathing is visible in the passive spectrogram (this particular subject displays signs of Cheyne-Stokes breathing and probably primary snoring (34% of total record time according to the snore detection algorithm)). FIGS. 32 to 33 illustrate graphic displays of signals of passive and active sensing in a classification of severe OSA, primarily based on hypopnea events, on a common time scale showing indications (see lower graph panel) of the classified events (e.g., obstructive apnea, mixed obstructive/central apnea, central apnea, and hypopnea).

Snoring and Link to Obstructive Apnea

The snoring detection algorithm can provide useful features for SDB detection, and in particular for event typification. There may be a clear correlation between total snoring time and the AHI for example. Records with a dominant obstructive component have a high proportion of the total sleep time (TST) with snoring. Most records with dominant central component have low levels of snoring, however there are exceptions. It might be the case that for these exceptions, the detected snoring is in fact primary snoring. This can be further analyzed by the system by looking at a more granular level (i.e., relating the snoring flag to the SDB events).

The Physician

The physician can get insight into the health of patients that are suffering from COPD or other chronic condition, and potentially connect to patients that need care, but do not yet realize that they have the symptoms of a chronic disease. Thus, the processing device and its application (app) may be configured to produce/communicate cough related information to clinical systems for remote monitoring of the cough related information.

Elderly Care/Independent Living

As background, a connected care value proposition for this system exists in the elderly care market—with the goal of reducing the burden of care, particularly in independent living, by incorporating active SONAR and/or passive acoustic technology, such as previously described, in elderly care digital assistive living tools. The system has wide potential—e.g., those in independent living may also suffer from asthma, COPD, CHF, Dementia, Alzheimer's etc. In 2015, one out of eight people worldwide was aged 60 years or over. By 2030, one in six people will be 60+ years old.

Current Independent Living solutions are typically disparate pieces of often expensive hardware with basic sensors (e.g., door sensors, water flow, bed occupancy, PIR motion, pressure pads, pill boxes, louder telephones, wearable movement). In contrast, a more complete solution can be delivered by incorporating passive audio and active sonar into a smartphone and/or smart speakers around the home. The active sonar and passive acoustic analysis outline herein can fill this gap by enabling the following in the living environment (e.g., home, assisted living facility, nursing home/elder care facility etc.):

Movement and Activity Tracking:

This can be done on the macro scale of detecting any movement in the room with active sensing (e.g., using CW or FMCW SONAR [processing any available range "bins"—e.g., all ranges] and/or by passively sensing/listening for characteristics sounds of movement.

For the latter (passive only), a quiet environment is desirable with limited numbers of environmental interferers (e.g., a desk or ceiling fan or open window with some external noise is OK, but loud speech or a nearby TV at high volume (not uncommon with Seniors with reduced hearing) makes a pure passive acoustic analysis difficult. In contrast, and ultrasonic FMCW or UWB acoustic system can better tolerate such interference.

FMCW or UWB techniques are also able to localize range, so in addition to detecting any movement, the system can classify the activity based on intensity and duration of the movement, and classify the characteristic signature of an activity.

Breath(ing) while Sitting Down or Lying Down:

Seniors may spend a lot of time sitting in front of the TV, and indeed may spend even more time there (i.e., trying to sleep in a chair) if their condition is worsening (such as difficulty breathing when lying down due to heart failure, or in people with COPD).

This uses FMCW, (A)FHRG, UWB etc. to localize the likely breathing frequencies in space, and tracking the user.

Sleep Staging Insights:

Tracking sleep fragmentation metrics, such as by detecting degradation in sleep metrics as an indication of worsening dementia and Alzheimer's.

Passive Audio Disease Progression Insights:

This is related to detecting in changes over time in acoustic signatures, such as prevalence and intensity of coughing, periods of unusual breathing rates.

This can be done where one or more smart speakers are placed in the home environment (e.g., commercial smart devices such as Amazon Echo Dot placed beside the bed, a Google Home Mini in the living room/TV room, a Google mini near or in the kitchen area etc.)

Adding Acoustic Signatures to Daily Life (User Environmental Interaction):

The system can "listen" with passive analysis for the characteristic sounds of a fridge door being opened, microwave, oven, front door, and communicate these events to a monitoring station. Other characteristic sounds that indicate an event include microwave oven timer "ding" or door bell. Such user environmental interaction signatures, such as relating to appliance use, can provide an indication of activity of a monitored person, which can then serve as an indication of user condition/health such as in relation to norms or consistency/patterns of activity of the monitored person. An absence of such activity in an expected time frame may be considered an indication of concern or taken as a need for more direct contact to check on the monitored person (e.g., the elderly person).

Alternatively, small ultrasonic "clickers" can be installed on these doors etc. to create a characteristic sounds (that may be audible or inaudible to people) in order that the system may better determine the exact event occurring. In contrast to commonly used sensors, this clicker requires no batteries or electronics as it is a simple mechanical component that "clicks" at a high frequency. This could be a two part device that attaches to door and to frame, or a single inertial device that attaches to the door with an adhesive and/or magnet. Thus, monitoring of many aspects of the home environment can be realised.

An active version of the ultrasonic "clicker" may be used to provide further information. An active clicker transmits a data modulated CW sound, audible or inaudible, to indicate an event, such as the status or the change in status of a window or door.

8.3.4.1.3 Output Module 8830

Example output which may be displayed on a display of a processing device, such as a computer or a mobile phone, based on the aforementioned assessments and signals may be considered in reference to the example graphic indicators of FIGS. 14 to 17 and 34 to 38. In this regard, any signals/information produced by the assessment module(s) may generated as output by the output module 8830. For example, determinations of the SDB risk (or SDB probability) are output in a graphic risk-o-meter. The risk-o-meter may include a pointer such as a needle and a scale, such as a scale from 1 to 100. Other suitable forms and/or scales may also be provided. The scale may be round or form an arc so as to permit the pointer to indicate a reading along the scale from one pivot point. In some versions, discrete portions (ranges) of the scale may reflect different colors to provide different characterizations along the scale. For example, the scale may present ranges for a normal characterization (e.g., 0 to 15) and a risky sleeper characterization (e.g., 15 to 100). The risky sleeper characterization may be formed by multiple sub-characterizations, such as high and low. In the example, a high risk range for a risky sleeper characterization, which may be coded red, ranges from 30 to 100. The low range for a risky sleeper characterization, which may be coded orange, ranges from 15 to 30. Similarly, the normal sleeper characterization may be formed by multiple sub-characterizations, such as low and nominal. In the example, a low risk range for a normal sleeper characterization, which may be coded yellow, ranges from 5 to 15. The nominal range for a normal sleeper characterization, which may be coded green, ranges from 0 to 5. In the examples of FIGS. 14 to 17 and FIG. 34, the risk probability value as determined in the assessment module 8820, is applied by the output module 8830 to generate indictor with the pointer indicating the determined risk onto the graphic scale. A text label may also optionally provide a label for the identified sleep characterization from the ranges of the scale. In some versions, as illustrated, the graphic indicator may also include a text label with an estimated AHI count as determined by the classifier of the assessment module 8820. In the example risk meter of FIG. 34, a curve (e.g., a circular curve segment) may be filled proportionally with a color indication of the level of risk associated with the calculated probability.

In some versions, such a range or risk assessment (e.g., the count or risk probability) may be forwarded to a medical practitioner or another relevant party, or be applied to a respiratory therapy controller for adjustment of a therapy provided by an RPT device. For example, such a risk assessment indicative of SDB may serve as input to a processor and/or therapy controller of the RPT, such as when the assessment is communicated to the RPT device from an external processing device or when it is determined by a processor of the RPT device. The processor or controller may then change a treatment pressure, a treatment flow rate or other treatment parameters for addressing the SDB risk depending on the value of the SDB risk.

Optionally, as illustrated in FIG. 17, the indictor may present a message that insufficient data has been collected, such as if the sleep session includes sensing signals from a session of less than a threshold (e.g., 1 hour). Another example of such a user interface display is shown in FIG. 35 in association with snore information data and a sleep score of a sleep session.

8.3.5 Potential Benefits of Some Examples of the Technology

Some versions of the present technology may provide any of the following:

(1) Non-contact SDB screening with an RF hardware sensor and/or SONAR sensing apparatus using an application (e.g., software).
(2) Sleep stages may be detected, including to accurately estimate AHI.
(3) Sleep/wake correction may be provided, such as for subjects with severe SDB, to improve accuracy in predicting AHI and sleep stages;
(4) Both active (SONAR or RF) and passive (mic) sensor/feature may be implemented in a synergistic fusion of technologies to produce a result even if the system is not optimally positioned in the most beneficial sensing direction;
(5) Features from both active sensing signals and passive sensing signals may be evaluated to distinguish central from obstructive and other types of events.
(6) An Assessment involving longer timescale periodic modulations in breathing/audio/movement (both intensity and frequency) rather than isolated detection of individual events, such that this system can be more robust to common interferers/confounders.
(7) Captures not only modulation in effort or audio but also movements associated with SDB related arousals/recoveries.
(8) The system may be configured to focus detection of the nearest person in bed so as to avoid sensing of an additional person further from the non-contact sensing apparatus.

Glossary

For the purposes of the present technology disclosure, in certain forms of the present technology, one or more of the following definitions may apply. In other forms of the present technology, alternative definitions may apply.

8.3.6 General

Air: In certain forms of the present technology, air may be taken to mean atmospheric air, and in other forms of the present technology air may be taken to mean some other combination of breathable gases, e.g. atmospheric air enriched with oxygen.

Continuous Positive Airway Pressure (CPAP): CPAP treatment will be taken to mean the application of a supply of air to the entrance to the airways at a pressure that is continuously positive with respect to atmosphere, and preferably approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

8.3.7 Aspects of the Respiratory Cycle

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: Preferably, a hypopnea will be taken to be a reduction in flow, but not a cessation of flow. In one form, a hypopnea may be said to have occurred when there is a reduction in flow below a threshold for a duration. A central hypopnea will be said to have occurred when a hypopnea is detected that is due to a reduction in breathing effort.

Hyperpnea: An increase in flow to a level higher than normal flow.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the RPT device's estimate of respiratory airflow, as opposed to "true respiratory flow" or "true respiratory airflow", which is the actual respiratory flow experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

8.3.8 RPT Device Parameters

Flow rate (or flow): The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. Total flow, Qt, is the flow rate of air leaving the RPT device. Vent flow, Qv, is the flow rate of air leaving a vent to allow washout of exhaled gases. Leak flow, Ql, is the flow rate of unintentional leak from a patient interface system. Respiratory flow, Qr, is the flow rate of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face. In one example leak may occur in a swivel elbow.

8.4 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology. For example, additional versions of the present technology may also be understood upon consideration of the following descriptive paragraphs and examples. To this end, the technology may also involve:

EXAMPLE 1. A method of one or more processors for monitoring a sleep disordered breathing state of a person, the method in the one or more processors comprising:
  extracting one or more respiratory signals from one or more motion signals, the one or more motion signals generated by active non-contact sensing;
  extracting one or more energy band signals from a passive signal, the passive signal generated by passive non-contact sensing, the passive signal representing acoustic information detected by a sound sensor;
  assessing the one or more energy band signals and/or the one or more respiratory signals to generate one or more intensity signals representing intensity of sleep disorder breathing modulation; and
  classifying one or more features derived from the one or more intensity signals to generate one or more measures of sleep disordered breathing.

EXAMPLE 2. The method of EXAMPLE 1 further comprising
  generating a sleep disordered breathing indicator based on the one or more measures of sleep disordered breathing.

EXAMPLE 3. The method of EXAMPLE 2 further comprising displaying, on a display, and/or forwarding the sleep disordered breathing indicator.

EXAMPLE 4. The method of any one of EXAMPLES 1 to 3 further comprising displaying, on a display, and/or forwarding the one or more measures of sleep disordered breathing.

EXAMPLE 5. The method of any one of EXAMPLES 1 to 4 wherein the one or more respiratory signals comprises a respiratory effort signal.

EXAMPLE 6. The method of any one of EXAMPLES 1 to 5 wherein the one or more measures of sleep disordered breathing comprises a probability of sleep disordered breathing.

EXAMPLE 7. The method of any one of EXAMPLES 1 to 6 wherein the classifying comprises identifying one of an affirmation and a negation of a presence of a number of sleep disordered breathing events exceeding a threshold for a sleep session, and wherein the one or more measures of sleep disordered breathing comprises a binary flag representing a result of the identifying.

EXAMPLE 8. The method of EXAMPLE 7, when dependent on EXAMPLE 6, wherein the binary flag represents the affirmation when the probability exceeds a threshold.

EXAMPLE 9. The method of EXAMPLE 7 wherein the sleep disordered breathing events comprises at least one of apnea and hypopnea events.

EXAMPLE 10. The method of any one of EXAMPLES 1 to 9 wherein the one or more measures of sleep disordered breathing comprises an apnea-hypopnea index representing an estimate of a total number of apnea events and hypopnea events.

EXAMPLE 11. The method of any one of EXAMPLES 1 to 10, when dependent on EXAMPLE 6, further comprising generating a sleep stage adjustment factor based on the probability.

EXAMPLE 12. The method of EXAMPLE 11 further comprising adjusting a sleep stage time as a function of the adjustment factor.

EXAMPLE 13. The method of any one of EXAMPLES 1 to 12 further comprising generating a cluster flag signal based one or more intensity signals, the cluster flag signal representing a time series identifying presence and absence of SDB modulation.

EXAMPLE 14. The method of EXAMPLE 13 wherein the cluster flag signal is generated based comparisons between values of the one or more intensity signals and a threshold.

EXAMPLE 15. The method of EXAMPLE 14 wherein a flag of the cluster flag signal is set to true when a value the one or more intensity signals is greater than a first intensity threshold.

EXAMPLE 16. The method of EXAMPLE 15, wherein the cluster flag signal is further set according to an evaluation of values of a filtered signal when compared to a second intensity threshold, the filtered signal being derived by filtering the one or more intensity signals.

EXAMPLE 17. The method of any one of EXAMPLES 1 to 16 wherein the one or more features comprise one or more proportions of total sleep time having SDB clusters.

EXAMPLE 18. The method of any one of EXAMPLES 1 to 17 wherein the one or more features comprise a peak intensity or peak mean intensity.

EXAMPLE 19. The method of any one of EXAMPLES 1 to 18 further comprising generating a sleep-wake correction mask signal based on a generated cluster flag signal that characterizes a presence of detected SDB clusters.

EXAMPLE 20. The method of EXAMPLE 19 further comprising applying the sleep-wake correction mask signal to a sleep staging process wherein instances of wake classification are corrected to instances of sleep according to the sleep-wake correction mask signal.

EXAMPLE 21. The method of any one of EXAMPLES 1 to 20 wherein the generated sleep disordered breathing indicator comprises a graphic risk-o-meter displayed on a display device, the graphic risk-o-meter comprising a pointer and scale.

EXAMPLE 22. The method of EXAMPLE 21 wherein the scale is presented with indications of discrete ranges of sleep disordered breathing risk.

EXAMPLE 23. The method of any one of EXAMPLES 1 to 22 wherein the assessing the one or more respiratory signals to generate one or more intensity signals representing intensity of sleep disorder breathing modulation comprises:
  generating an envelope signal;
  normalizing the envelope signal; and
  generating spectral characteristics from the normalized envelope signal.

EXAMPLE 24. The method of EXAMPLE 23 wherein the spectral characteristics comprise peak frequencies of power spectral density operations in a sleep disordered breathing frequency range.

EXAMPLE 25. The method of any one of EXAMPLES 23 and 24 wherein the spectral characteristics comprise an in-band metric comprising a ratio of: (a) a peak frequency of a power spectral density operation, and (b) power in the sleep disordered breathing frequency range from the power spectral density operation.

EXAMPLE 26. The method of any one of EXAMPLES 23 and 24 wherein the spectral characteristics comprise an in-band metric comprising a ratio of: (a) power in a narrow band around a peak frequency of a power spectral density operation, and (b) a difference between a total power of the spectrum of the power spectral density operation and the power in the narrow band around the peak frequency.

EXAMPLE 27. The method of any one of EXAMPLES 25 and 26 wherein the in-band metric is an average metric derived from in-band metric values from an I channel motion signal and a Q channel motion signal.

EXAMPLE 28. The method of any one of EXAMPLES 1 to 27 wherein the assessing the one or more energy band signals to generate one or more intensity signals representing intensity of sleep disorder breathing modulation comprises:
  combining the one or more energy band signals;
  generating an envelope signal from the combined energy band signals;
  filtering and normalizing the envelope signal from the combined energy band signals; and
  generating spectral characteristics from the filtered and normalized envelope signal.

EXAMPLE 29. The method of EXAMPLE 28 wherein the spectral characteristics from the filtered and normalized envelope signal comprise an in-band metric comprising a ratio of: (a) a peak frequency of a power spectral density operation, and (b) power in a sleep disordered breathing frequency range from the power spectral density operation.

EXAMPLE 30. The method of EXAMPLE 28 wherein the spectral characteristics from the filtered and normalized envelope signal comprise an in-band metric comprising a ratio of: (a) power in a narrow band around a peak frequency of a power spectral density operation, and (b) a difference between a total power of the spectrum of the power spectral density operation and the power in the narrow band around the peak frequency.

EXAMPLE 31. The method of any one of EXAMPLES 1 to 30 wherein the extracting one or more respiratory signals from one or more motion signals comprises combining a plurality of motion signals, each of the plurality of motion signals being a motion signal representing motion from a detection range that is different from a detection range from other motion signals of the plurality of motion signals.

EXAMPLE 32. The method of EXAMPLE 31 wherein the combining comprises computing weights according to respiratory frequencies from a power spectral density for each of the plurality of motion signals and determining a weighted average of absolute values of the plurality of motion signals.

EXAMPLE 33. The method of any one of EXAMPLES 1 to 32 wherein the extracting of one or more energy band signals from a passive signal comprises:
  separating sound frequencies of the passive signal into band signals by computing transformations of the passive signal;
  computing energy values of the band signals; and
  averaging computed energy values for each band signal.

EXAMPLE 34. The method of any one of EXAMPLES 1 to 33 wherein the active non-contact sensing comprises SONAR sensing with a microphone and speaker.

EXAMPLE 35. The method of any one of EXAMPLES 1 to 33 wherein the active non-contact sensing comprises RADAR sensing with a radio frequency transmitter and receiver.

EXAMPLE 36. The method of any one of EXAMPLES 1 to 35 wherein the active non-contact sensing comprises frequency modulated continuous wave (FMCW) sensing.

EXAMPLE 37. The method of any one of EXAMPLES 1 to 36 wherein the passive non-contact sensing comprises acoustic sensing of breathing related sounds with a microphone.

EXAMPLE 38. The method of EXAMPLE 37 further comprising pre-processing a sound signal generated by the microphone to produce the passive signal, the pre-processing comprising any one or more of filtering with an infinite impulse response filter; baseline removal comprising subtraction of a minimum over a sliding window; artefact removal employing a percentile limit; normalization with a standard deviation over a sliding window; and integration and high-pass filtering.

EXAMPLE 39. The method of EXAMPLE 38 further comprising autocorrelating the pre-processed sound signal.

EXAMPLE 40. The method of EXAMPLE 39 further comprising detecting a peak with a pre-defined respiration range of the autocorrelated, pre-processed sound signal.

EXAMPLE 41. The method of EXAMPLE 40 further comprising determining a respiration rate estimate from peaks of a plurality of signals, each of the plurality of signals being a sound signal of a discrete frequency band and processed by the pre-processing and the autocorrelating.

EXAMPLE 42. The method of any one of EXAMPLE 1 to 41 wherein the one or more features is a plurality of features derived from a plurality of intensity signals from the one or more energy band signals and the one or more respiratory signals, and the generated one or more measures of sleep disordered breathing are generated by classification of the plurality of features.

EXAMPLE 43. The method of any one of EXAMPLES 1 to 42 wherein the one or more processors are in a processing device, the processing device comprising any of a smart phone, a tablet computer, a general computing device, a smart speaker, a smart TV, a smart watch and a respiratory therapy device.

EXAMPLE 44. The method of any one of EXAMPLES 1 to 43 further comprising controlling, with the one or more processors, a change to a setting of a therapy of a respiratory therapy device based on the one or more measures of sleep disordered breathing.

EXAMPLE 45. A processor-readable medium, having stored thereon processor-executable instructions which, when executed by one or more processors, cause the one or more processors to monitor a sleep disordered breathing state of a person, the processor-executable instructions configured to execute the method of any one of EXAMPLES 1 to 44.

EXAMPLE 46. A server with access to the processor-readable medium of EXAMPLE 45, wherein the server is configured to receive requests for downloading the processor-executable instructions of the processor-readable medium to a processing device over a network.

EXAMPLE 47. A processing device comprising: one or more processors; a speaker coupled to the one or more processors; a microphone coupled to the one or more processors; and a processor-readable medium of EXAMPLE 45.

EXAMPLE 48. The processing device of EXAMPLE 47 wherein the processing device comprises any of a smart phone, a tablet computer, a general computing device, a smart speaker, a smart TV, a smart watch and a respiratory therapy device.

EXAMPLE 49. A processing device comprising one or more processors; a microphone coupled to the one or more processors; a radio frequency sensor coupled to the one or more processors; and the processor-readable medium of EXAMPLE 45.

EXAMPLE 50. A method of a server having access to the processor-readable medium of EXAMPLE 45, the method comprising receiving, at the server, a request for downloading the processor-executable instructions of the processor-readable medium to a processing device over a network; and transmitting the processor-executable instructions to the processing device in response to the request.

EXAMPLE 51. Apparatus for monitoring a sleep disordered breathing state of a person, the apparatus comprising:
one or more sensors configured for active non-contact sensing and passive non-contact sensing; and
one or more processors configured to:
extract one or more respiratory signals from one or more motion signals, the one or more motion signals generated by active non-contact sensing with the one or more sensors;
extract one or more energy band signals from a passive signal, the passive signal generated by passive non-contact sensing with the one or more sensors, the passive signal representing acoustic information detected by a sound sensor of the one or more sensors;
assess the one or more energy band signals and/or the one or more respiratory signals to generate one or more intensity signals representing intensity of sleep disorder breathing modulation; and
classify one or more features derived from the one or more intensity signals to generate one or more measures of sleep disordered breathing.

EXAMPLE 52. The apparatus of EXAMPLE 51 wherein the one or more processors is further configured to generate a sleep disordered breathing indicator based on the one or more measures of sleep disordered breathing.

EXAMPLE 53. The apparatus of EXAMPLE 52 wherein the one or more processors is further configured to display, on a display, and/or forward the sleep disordered breathing indicator.

EXAMPLE 54. The apparatus of any one of EXAMPLES 51 to 53 wherein the one or more processors is further configured to display, on a display, and/or forward the one or more measures of sleep disordered breathing.

EXAMPLE 55. The apparatus of any one of EXAMPLES 51 to 54 wherein the one or more respiratory signal comprises a respiratory effort signal.

EXAMPLE 56. The apparatus of any one of EXAMPLES 51 to 55 wherein the one or more measures of sleep disordered breathing comprises a probability of sleep disordered breathing.

EXAMPLE 57. The apparatus of any one of EXAMPLES 51 to 56 wherein the classifying comprises identifying one of an affirmation and a negation of a presence of a number of sleep disordered breathing events exceeding a threshold for a sleep session, and wherein the one or more measures of sleep disordered breathing comprises a binary flag representing a result of the identifying.

EXAMPLE 58. The apparatus of EXAMPLE 57, when dependent on EXAMPLE 56, wherein the binary flag represents the affirmation when the probability exceeds a threshold.

EXAMPLE 59. The apparatus of EXAMPLE 57 wherein the sleep disordered breathing events comprises at least one of apnea and hypopnea events.

EXAMPLE 60. The apparatus of any one of EXAMPLES 51 to 59 wherein the one or more measures of sleep disordered breathing comprises an apnea-hypopnea index representing an estimate of a total number of apnea events and hypopnea events.

EXAMPLE 61. The apparatus of any one of EXAMPLES 51 to 60, when dependent on EXAMPLE 54, wherein the one or more processors is further configured to generate a sleep stage adjustment factor based on the probability.

EXAMPLE 62. The apparatus of EXAMPLE 61 wherein the one or more processors are further configured to adjust a sleep stage time as a function of the adjustment factor.

EXAMPLE 63. The apparatus of any one of EXAMPLES 51 to 62 wherein the one or more processors are further configured to generate a cluster flag signal based one or more intensity signals, the cluster flag signal representing a time series identifying presence and absence of SDB modulation.

EXAMPLE 64. The apparatus of EXAMPLE 63 wherein the cluster flag signal is generated based comparisons between values of the one or more intensity signals and a threshold.

EXAMPLE 65. The apparatus of EXAMPLE 64 wherein a flag of the cluster flag signal is set to true when a value the one or more intensity signals is greater than a first intensity threshold.

EXAMPLE 66. The apparatus of EXAMPLE 65, wherein the cluster flag signal is further set according to an evaluation of values of a filtered signal in comparison with a second intensity threshold, the filtered signal being derived by filtering the one or more intensity signals.

EXAMPLE 67. The apparatus of any one of EXAMPLES 51 to 66 wherein the one or more features comprise one or more proportions of total sleep time having SDB clusters.

EXAMPLE 68. The apparatus of any one of EXAMPLES 51 to 67 wherein the one or more features comprise a peak intensity or peak mean intensity.

EXAMPLE 69. The apparatus of any one of EXAMPLES 51 to 68 wherein the one or more processors are further configured to generate a sleep-wake correction mask signal based on a generated cluster flag signal that characterizes a presence of detected SDB clusters.

EXAMPLE 70. The apparatus of EXAMPLE 69 wherein the one or more processors is further configured to apply the sleep-wake correction mask signal to a sleep staging process wherein instances of wake classification are corrected to instances of sleep according to the sleep-wake correction mask signal.

EXAMPLE 71. The apparatus of any one of EXAMPLES 51 to 70 wherein the generated sleep disordered breathing indicator comprises a graphic risk-o-meter displayed on a display device, the graphic risk-o-meter comprising a pointer and scale.

EXAMPLE 72. The apparatus of EXAMPLE 71 wherein the scale is presented with indications of discrete ranges of sleep disordered breathing risk.

EXAMPLE 73. The apparatus of any one of EXAMPLES 51 to 72 wherein to assess the one or more respiratory signals to generate one or more intensity signals representing intensity of sleep disorder breathing modulation, the one or more processors are configured to:
  generate an envelope signal;
  normalize the envelope signal; and
  generate spectral characteristics from the normalized envelope signal.

EXAMPLE 74. The apparatus of EXAMPLE 73 wherein the spectral characteristics comprise peak frequencies of power spectral density operations in a sleep disordered breathing frequency range.

EXAMPLE 75. The apparatus of any one of EXAMPLES 73 and 74 wherein the spectral characteristics comprise an in-band metric comprising a ratio of: (a) a peak frequency of a power spectral density operation, and (b) power in the sleep disordered breathing frequency range from the power spectral density operation.

EXAMPLE 76. The apparatus of any one of EXAMPLES 73 and 74 wherein the spectral characteristics comprise an in-band metric comprising a ratio of: (a) power in a narrow band around a peak frequency of a power spectral density operation, and (b) a difference between a total power of the spectrum of the power spectral density operation and the power in the narrow band around the peak frequency.

EXAMPLE 77. The apparatus of any one of EXAMPLES 73 and 76 wherein the in-band metric is an average metric derived from in-band metric values from an I channel motion signal and a Q channel motion signal.

EXAMPLE 78. The apparatus of any one of EXAMPLES 51 to 77 wherein to assess the one or more energy band signals to generate one or more intensity signals representing intensity of sleep disorder breathing modulation, the one or more processors are configured to:
  combine the one or more energy band signals;
  generate an envelope signal from the combined energy band signals; and
  filter and normalize the envelope signal from the combined energy band signals; and
  generate spectral characteristics from the filtered and normalized envelope signal.

EXAMPLE 79. The apparatus of EXAMPLE 78 wherein the spectral characteristics from the filtered and normalized envelope signal comprise an in-band metric comprising a ratio of: (a) a peak frequency of a power spectral density operation, and (b) power in a sleep disordered breathing frequency range from the power spectral density operation.

EXAMPLE 80. The apparatus of EXAMPLE 78 wherein the spectral characteristics from the filtered and normalized envelope signal comprise an in-band metric comprising a ratio of: (a) power in a narrow band around a peak frequency of a power spectral density operation, and (b) a difference between a total power of the spectrum of the power spectral density operation and the power in the narrow band around the peak frequency.

EXAMPLE 81. The apparatus of any one of EXAMPLES 51 to 80 wherein to extract one or more respiratory effort signals from one or more motion signals, the one or more processors is configured to combine a plurality of motion signals, each of the plurality of motion signals being a motion signal representing motion from a detection range that is different from a detection range from other motion signals of the plurality of motion signals.

EXAMPLE 82. The apparatus of EXAMPLE 81 wherein to combine the plurality of motion signals, the one or more processors is configured to compute weights according to respiratory frequencies from a power spectral density for each of the plurality of motion signals and to determine a weighted average of absolute values of the plurality of motion signals.

EXAMPLE 83. The apparatus of any one of EXAMPLES 51 to 82 wherein to extract the one or more energy band signals from a passive signal, the one or more processors are configured to:
  separate sound frequencies of the passive signal into band signals by computing transformations of the passive signal;
  compute energy values of the band signals; and
  average computed energy values for each band signal.

EXAMPLE 84. The apparatus of any one of EXAMPLES 51 to 83 wherein the active non-contact sensing comprises SONAR sensing wherein the one or more sensors comprises a microphone and speaker.

EXAMPLE 85. The apparatus of any one of EXAMPLES 51 to 83 wherein the active non-contact sensing comprises RADAR sensing wherein the one or more sensors comprises a radio frequency transmitter and receiver.

EXAMPLE 86. The apparatus of any one of EXAMPLES 51 to 85 wherein the active non-contact sensing comprises frequency modulated continuous wave (FMCW) sensing.

EXAMPLE 87. The apparatus of any one of EXAMPLES 51 to 86 wherein the passive non-contact sensing comprises acoustic sensing of breathing related sounds wherein the one or more sensors comprises a microphone.

EXAMPLE 88. The apparatus of EXAMPLE 87 wherein the one or more processors are configured to pre-process a sound signal generated by the microphone to produce the passive signal, wherein the pre-processing comprises any one or more of: filtering with an infinite impulse response filter; baseline removal comprising subtraction of a minimum over a sliding window; artefact removal employing a percentile limit; normalization with a standard deviation over a sliding window; and integration and high-pass filtering.

EXAMPLE 89. The apparatus of EXAMPLE 88 wherein the one or more processors are configured to autocorrelate the pre-processed sound signal.

EXAMPLE 90. The apparatus of EXAMPLE 89 wherein the one or more processors are configured to detect a peak with a pre-defined respiration range of the autocorrelated, pre-processed sound signal.

EXAMPLE 91. The apparatus of EXAMPLE 90 wherein the one or more processors are configured to determine a respiration rate estimate from peaks of a plurality of signals, each of the plurality of signals being a sound signal of a discrete frequency band and processed by the pre-processing and the autocorrelating.

EXAMPLE 92. The apparatus of any one of EXAMPLE 51 to 91 wherein the one or more features is a plurality of features derived from a plurality of intensity signals from the one or more energy band signals and the one or more respiratory efforts signals, and the generated one or more measures of sleep disordered breathing are generated by classification of the plurality of features.

EXAMPLE 93. The apparatus of any one of EXAMPLES 51 to 92 wherein the one or more processors are in a processing device, the processing device comprising any of a general computing device, a smart phone, a tablet computer, a smart speaker, a smart TV, a smart watch and a respiratory therapy device.

EXAMPLE 94. The apparatus of any one of EXAMPLES 51 to 93 wherein the one or more processors are configured to control a change to a setting of a therapy of a respiratory therapy device based on the one or more measures of sleep disordered breathing.

EXAMPLE 95. The apparatus of EXAMPLE 51 further comprising a processor-readable medium of EXAMPLE 45.

EXAMPLE 96. A method of one or more processors for identifying coughing by a person, the method in the one or more processors comprising:
 accessing a signal generated with a microphone, the signal generated by passive non-contact sensing in a vicinity of a person, the signal representing acoustic information detected by the microphone;
 deriving one or more cough related features from the signal; and
 classifying the one or more features to generate an indication of one or more events of coughing by the person.

EXAMPLE 97. The method of EXAMPLE 96 the one more features concern an absence or presence of coughing of the person.

EXAMPLE 98. The method of any one of EXAMPLES 96 to 97 wherein the classifying the one or more features comprises identifying a cough type.

EXAMPLE 99. The method of EXAMPLE 98 wherein the coughing type comprises any one or more of (a) dry coughing type, (b) productive coughing type, (c) wheezing related coughing type, and (d) spasm related coughing type.

EXAMPLE 100. The method of any one of EXAMPLES 96 to 99 wherein classifying the one or more features comprises identifying a cough attribution type.

EXAMPLE 101. The method of EXAMPLE 100 wherein the cough attribution type comprises any one or more of (a) asthmatic coughing type, (b) Chronic obstructive pulmonary (COPD) coughing type, (c) bronchitis coughing type, (d) tuberculosis (TB) coughing type, (e) pneumonia coughing type, (f) lung cancer coughing type, (g) gastroesophageal reflux disease (GERD), and (h) upper airway cough syndrome.

EXAMPLE 102. The method of any one of EXAMPLES 96 to 101 wherein the one or more processors further generates a coughing intensity metric indicative of a level of intensity of an event of the one or more events of coughing.

EXAMPLE 103. The method of EXAMPLE 102 wherein the coughing intensity metric comprises an acoustic amplitude value and/or a loudness value.

EXAMPLE 104. The method of any one of EXAMPLES 102 to 103 wherein the one or more processors determines variability of the coughing intensity metric.

EXAMPLE 105. The method of any one of EXAMPLES 96 to 104 wherein the one or more features derived from the acoustic signal comprises any one, more or all of: a frequency feature, a temporal feature, a spectrogram feature and a wavelet feature.

EXAMPLE 106. The method of any one of EXAMPLES 96 to 105 wherein a frequency related feature of the one or more features derived from the acoustic signal comprises any one, more or all of: (1) a local peak, (2) a ratio of a dominant peak to one or more surrounding peaks, (3) a local maxima, (4) a global maxima; (5) harmonics, (6) an integration of one or more frequency components, (8) a ratio of different frequency energy estimates, (7) one or more Mel-frequency cepstral coefficients (MFCCs), (9) spectral flux, (10) a spectral centroid, (11) a harmonic product spectrum, (12) a spectral spread, (13) one or more spectral autocorrelation coefficients, (14) a spectral kurtosis, and (15) a linear Predictive Coding (LPC).

EXAMPLE 107. The method of any one of EXAMPLES 96 to 106 wherein a temporal related feature of the one or more features derived from the acoustic signal comprises any one, more or all of: (1) a root mean square (RMS) value, (2) a zero-crossing rate, (3) an envelope; and (4) a pitch based on an auto correlation function.

EXAMPLE 108. The method of any one of EXAMPLES 96 to 107 further comprising processing the acoustic signal by voice activation detection to reject background noise in the acoustic signal.

EXAMPLE 109. The method of any one of EXAMPLES 96 to 108 further comprising estimating a cough rate from the acoustic signal.

EXAMPLE 110. The method of EXAMPLE 109 further comprising estimating a variation of cough rate.

EXAMPLE 111. The method of any one of EXAMPLES 96 to 111 wherein the one or more processors are configured to extract respiratory features from a detected breathing waveform and wherein the classifying of the one or more features to generate an indication of one or more events of coughing by the person, is based on one or more respiratory waveform features extracted from the breathing waveform.

EXAMPLE 112. The method of EXAMPLE 111 wherein the one or more respiratory features comprises one, more or all of: (1) inspiration time, (2) inspiration depth, (3) expiration time, (4) expiration depth, (5) an inspiration-to-expiration ratio, (6) one or more notches in the breathing waveform due to cough, and (7) breathing rate.

EXAMPLE 113. The method of EXAMPLE 112 wherein the one or more respiratory features is derived with one or more of passive non-contact sensing and active non-contact sensing.

EXAMPLE 114. The method of any one of EXAMPLES 96 to 113 wherein the one or more processors generates one or more motion signals by active non-contact sensing with active non-contact sensing apparatus; and
 wherein the one or more processors generates the indication of one or more events of coughing by the person based on an evaluation of the generated one or more motion signals.

EXAMPLE 115. The method of EXAMPLE 114 further comprising detection of body position of the person.

EXAMPLE 116. The method of any one of EXAMPLES 114 to 115 wherein the evaluation of the generated one or more motion signals comprises detection of biometrics particular to the person.

EXAMPLE 117. The method of any one of EXAMPLES 113 to 116 wherein the evaluation of the generated one or more motion signals comprises a detection of sleep stage information from the one or more motion signals.

EXAMPLE 118. The method of EXAMPLE 117 wherein the one or more processors reject an acoustically sensed cough event based on the detection of sleep stage information.

EXAMPLE 119. The method of any one of EXAMPLES 117 to 118 wherein the one or more processors attribute an acoustically sensed cough event to the person based on the detection of sleep stage information.

EXAMPLE 120. The method of any one of EXAMPLES 114 to 119 wherein the active non-contact sensing comprises one or more of an acoustic-type sensing, an optical-type sensing, and a RADAR-type sensing.

EXAMPLE 121. The method of any one of EXAMPLES 96 to 120 wherein the one or more processors is further configured to communicate data concerning the indication of the one or more events of coughing by the person to recommend further investigation of the condition and/or to control one or more of; an environmental parameter, a setting on a treatment device, a behavioural change and/or a treatment parameter.

EXAMPLE 122. The method of any one of EXAMPLES 96 to 121 wherein the one or more processors is further configured to generate a reminder to change or wash bedclothes.

EXAMPLE 123. The method of any one of EXAMPLES 96 to 122 wherein the classifying involves a classifier derived by any one or more of supervised machine learning, deep learning, a convolutional neural network, and a recurrent neural network.

EXAMPLE 124. The method of any one of EXAMPLES 96 to 123 further comprising monitoring sound to detect user environmental interaction.

EXAMPLE 125. The method of EXAMPLE 124 wherein the user environmental interaction comprises detection of user environmental interaction signatures comprising any one of more of a clicker, an appliance and a door.

EXAMPLE 126. The method of any one of EXAMPLES 124 and 125 wherein the monitoring sound to detect user environmental interaction comprises assessing a pattern of activity of a monitored person to generate an indication of a need for contact with the monitored person.

EXAMPLE 127. A processor-readable medium, having stored thereon processor-executable instructions which, when executed by one or more processors, cause the one or more processors to identify coughing by a person, the processor-executable instructions configured to execute the method of any one of EXAMPLES 96 to 126.

EXAMPLE 128. A server with access to the processor-readable medium of EXAMPLE 127, wherein the server is configured to receive requests for downloading the processor-executable instructions of the processor-readable medium to a processing device over a network.

EXAMPLE 129. A processing device comprising: one or more processors; a speaker coupled to the one or more processors; a microphone coupled to the one or more processors; and a processor-readable medium of EXAMPLE 127 or wherein the one or more processors are configured to access the processor-executable instructions with the server of EXAMPLE 128.

EXAMPLE 130. The processing device of EXAMPLE 129 wherein the processing device comprises any of a smart phone, a tablet computer, a general computing device, a smart speaker, a smart TV, a smart watch and a respiratory therapy device.

EXAMPLE 131. A processing device comprising one or more processors; a microphone coupled to the one or more processors; a radio frequency sensor coupled to the one or more processors; and the processor-readable medium of EXAMPLE 127.

EXAMPLE 132. A method of a server having access to the processor-readable medium of EXAMPLE 127, the method comprising receiving, at the server, a request for downloading the processor-executable instructions of the processor-readable medium to a processing device over a network; and transmitting the processor-executable instructions to the processing device in response to the request.

EXAMPLE 133. A processing device for identifying coughing by a person comprising:
one or more microphones configured for passive non-contact sensing, wherein the one or more microphones generates a signal by passive non-contact sensing in a vicinity of a person, the signal representing acoustic information detected by the one or more microphones; and
one or more processors coupled to the one or more microphones, the one or more processors comprising:
a module configured to access the signal generated with the one or more microphones;
a module configured to derive one or more features from the signal; and
a module configured to classify the one or more features to generate an indication of one or more events of coughing by the person.

EXAMPLE 134. The processing device of EXAMPLE 133 wherein the processing device comprises any of a smart phone, a tablet computer, a general computing device, a smart speaker, a smart TV, a smart watch and a respiratory therapy device.

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

8.5 Reference Signs List sleeping patient 1000
contactless sensor unit 1200
ground electrode ISOG 2010
EOG electrode 2015
EEG electrode 2020
ECG electrode 2025
submental EMG electrode 2030
snore sensor 2035
respiratory inductance plethysmogram respiratory effort sensor 2040
respiratory inductance plethysmogram respiratory effort sensor 2045
oro-nasal cannula 2050
photoplethysmograph pulse oximeter 2055
body position sensor 2060
patient interface 3000
seal-forming structure 3100
plenum chamber 3200
structure 3300
vent 3400
connection port 3600
forehead support 3700
RPT device 4000
external housing 4010
upper portion 4012
portion 4014
panels 4015
chassis 4016
handle 4018
pneumatic block 4020
inlet air filter 4112
inlet muffler 4122
outlet muffler 4124
pressure generator 4140
blower 4142
air circuit 4170
electrical components 4200
PCBA 4202
electrical power supply 4210
input devices 4220
central controller 4230
therapy device controller 4240 protection circuits 4250
memory 4260
transducers 4270
pressure sensors 4272
flow rate sensors 4274
data communication interface 4280
output devices 4290
humidifier 5000
humidifier inlet 5002
humidifier outlet 5004
humidifier base 5006
humidifier reservoir 5110
heating element 5240
monitoring apparatus 7000
microcontroller unit MCU 7001
memory 7002
movement signal 7003
communications circuitry 7004
external computing device 7005
processor 7006
connection 7008
contactless motion sensor 7010
display device 7015
audio output 7017
transmitter 7020
receiver 7030
local oscillator 7040
(directional) antenna 7050
transmitted signal 7060
reflected signals 7070
mixer 7080
processing device 7100
application 7200
process 7202
process 7204
process 7206
process 7208
sound sensor 7302
processor 7304
display interface 7306
user control/input interface 7308
speaker 7310
memory/data storage 7312
extraction module 8810
active sensing signal extraction sub-module 8812
passive sensing signal extraction sub-module 8814
assessment module 8820
SDB modulation assessment sub-module 8822
sleep staging module 8824
SDB synopsis module 8826
output module 8830
Cough assessment module 8833
active sensing process/module 8902
passive sensing process/module 8904
sleep staging process/module 8906
assessment process/module 8908
respiratory effort process/module 8910
process/module 8912
feature extraction process/module 8914
learned features process/module 8916
cough related fingerprinting process/module 8918
snore classification process/module 8920
SDB assessment process/module 8922
sleep stages output process/module 8924
sleep scoring output process/module 8926
Output process/module 8928

The invention claimed is:

1. A method of one or more processors for monitoring a sleep disordered breathing state of a person, the method in the one or more processors comprising:
 extracting one or more respiratory signals from one or more motion signals, the one or more motion signals generated by active non-contact sensing;
 extracting one or more energy band signals from a passive signal, the passive signal generated by passive non-contact sensing, the passive signal representing acoustic information detected by a sound sensor;
 assessing the one or more energy band signals and/or the one or more respiratory signals to generate one or more intensity signals representing intensity of sleep disorder breathing modulation that comprises a modulation frequency characteristic in a sleep disordered breathing frequency range;
 classifying one or more features derived from the one or more intensity signals to generate one or more measures of sleep disordered breathing; and
 controlling, with the one or more processors, a change to a setting of a therapy for operating a respiratory therapy device to provide the therapy based on the one or more measures of sleep disordered breathing.

2. The method of claim 1 further comprising any one or more of:
 (a) generating a sleep disordered breathing indicator based on the one or more measures of sleep disordered breathing; (b) displaying, on a display, and/or forwarding the sleep disordered breathing indicator; and (c) displaying, on a display, and/or forwarding the one or more measures of sleep disordered breathing.

3. The method of claim 2 wherein the generated sleep disordered breathing indicator comprises a graphic risk-o-meter displayed on a display device, the graphic risk-o-meter comprising a pointer and scale.

4. The method of claim 1 wherein the classifying comprises identifying one of an affirmation and a negation of a presence of a number of sleep disordered breathing events exceeding a threshold for a sleep session, and wherein the one or more measures of sleep disordered breathing comprises a binary flag representing a result of the identifying.

5. The method of claim 4, wherein:
 (a) the one or more measures of sleep disordered breathing comprises a probability of sleep disordered breathing, and wherein the binary flag represents the affirmation when the probability exceeds a threshold; or
 (b) the one or more measures of sleep disordered breathing comprises an apnea-hypopnea index representing an estimate of a total number of apnea events and hypopnea events.

6. The method of claim 1, wherein the one or more measures of sleep disordered breathing comprises a probability of sleep disordered breathing, and the method further comprising: (a) generating a sleep stage adjustment factor based on the probability, and (b) adjusting a sleep stage time as a function of the sleep stage adjustment factor.

7. The method of claim 1 further comprising generating a cluster flag signal based one or more intensity signals, the cluster flag signal representing a time series identifying presence and absence of sleep disordered breathing (SDB) modulation.

8. The method of claim 7 wherein the cluster flag signal is generated based on comparisons between values of the one or more intensity signals and a threshold.

9. The method of claim 8 wherein a flag of the cluster flag signal is set to true when a value of the one or more intensity signals is greater than a first intensity threshold, and wherein the cluster flag signal is further set according to an evaluation of values of a filtered signal when compared to a second intensity threshold, the filtered signal being derived by filtering the one or more intensity signals.

10. The method of claim 1 wherein the one or more features comprise:
   (a) one or more proportions of total sleep time having sleep disordered breathing (SDB) clusters;
   (b) a peak intensity or peak mean intensity; and/or
   (c) a plurality of features derived from a plurality of intensity signals from the one or more energy band signals.

11. The method of claim 1 further comprising generating a sleep-wake correction mask signal based on a generated cluster flag signal that characterizes a presence of detected SDB clusters, and applying the sleep-wake correction mask signal to a sleep staging process wherein instances of wake classification are corrected to instances of sleep according to the sleep-wake correction mask signal.

12. The method of claim 1 wherein the assessing the one or more respiratory signals to generate one or more intensity signals representing intensity of sleep disorder breathing modulation comprises:
   generating an envelope signal;
   normalizing the envelope signal; and
   generating spectral characteristics from the normalized envelope signal.

13. The method of claim 12 wherein the spectral characteristics comprise any one or more of:
   (1) peak frequencies of power spectral density operations in a sleep disordered breathing frequency range;
   (2) an in-band metric comprising a ratio of: (a) a peak frequency of a power spectral density operation, and (b) power in the sleep disordered breathing frequency range from the power spectral density operation; and
   (3) an in-band metric comprising a ratio of: (a) power in a narrow band around a peak frequency of a power spectral density operation, and (b) a difference between a total power of the spectrum of the power spectral density operation and the power in the narrow band around the peak frequency.

14. The method of claim 1 wherein the assessing the one or more energy band signals to generate one or more intensity signals representing intensity of sleep disorder breathing modulation comprises:
   combining energy band signals of the one or more energy band signals;
   generating an envelope signal from the combined energy band signals;
   filtering and normalizing the envelope signal from the combined energy band signals; and
   generating spectral characteristics from the filtered and normalized envelope signal.

15. The method of claim 14 wherein the spectral characteristics from the filtered and normalized envelope signal comprise any one or both of:
   (1) an in-band metric comprising a ratio of: (a) a peak frequency of a power spectral density operation, and (b) power in a sleep disordered breathing frequency range from the power spectral density operation; and
   (2) an in-band metric comprising a ratio of: (a) power in a narrow band around a peak frequency of a power spectral density operation, and (b) a difference between a total power of the spectrum of the power spectral density operation and the power in the narrow band around the peak frequency.

16. The method of claim 1 wherein the extracting one or more respiratory signals from one or more motion signals comprises combining a plurality of motion signals, each of the plurality of motion signals being a motion signal representing motion from a detection range that is different from a detection range from other motion signals of the plurality of motion signals.

17. The method of claim 1 wherein the extracting one or more energy band signals from the passive signal comprises:
   separating sound frequencies of the passive signal into band signals by computing transformations of the passive signal;
   computing energy values of the band signals; and
   averaging computed energy values for each band signal.

18. The method of claim 1 wherein (1) the active non-contact sensing comprises any of: (a) active sound (SONAR) sensing with a microphone and speaker; (b) radio frequency (RADAR) sensing with a radio frequency transmitter and receiver; and (c) frequency modulated continuous wave (FMCW) sensing; and (2) the passive non-contact sensing comprises acoustic sensing of breathing related sounds with a microphone.

19. The method of claim 1 wherein the one or more processors are in a processing device, the processing device comprising any of a smart phone, a tablet computer, a general computing device, a smart speaker, a smart TV, a smart watch and the respiratory therapy device.

20. The method of claim 1 further comprising, in the one or more processors, receiving the generated one or more measures of sleep disordered breathing; and
   (a) displaying the received one or more measures of sleep disordered breathing on a display; or (b) transmitting, via data communications transmission, the received one or more measures of sleep disordered breathing to a local processing device.

21. The method of claim 1, wherein the sleep disordered breathing of said intensity of sleep disorder breathing modulation consists of determined clusters of apneic events.

22. The method of claim 1, wherein the respiratory therapy device comprises a respiratory pressure therapy device and the therapy is a positive airway pressure.

23. A processor-readable medium, having stored thereon processor-executable instructions which, when executed by one or more processors, cause the one or more processors to monitor a sleep disordered breathing state of a person, the processor-executable instructions configured to execute the method of claim 1.

24. Apparatus for monitoring a sleep disordered breathing state of a person, the apparatus comprising:
   one or more processors configured to:
      extract one or more respiratory signals from one or more motion signals, the one or more motion signals generated by active non-contact sensing with one or more sensors;
      extract one or more energy band signals from a passive signal, the passive signal generated by passive non-contact sensing with the one or more sensors, the passive signal representing acoustic information detected by a sound sensor of the one or more sensors;
      assess the one or more energy band signals and/or the one or more respiratory signals to generate one or more intensity signals representing intensity of sleep disorder breathing modulation that comprises a modulation frequency characteristic in a sleep disordered breathing frequency range; and classify one or more features derived from the one or more intensity signals to generate one or more measures of sleep disordered breathing; and control a change to a setting of a therapy for operating a respiratory therapy device to provide the therapy based on the one or more measures of sleep disordered breathing.

25. The apparatus of claim 24, wherein the sleep disordered breathing of said intensity of sleep disorder breathing modulation consists of determined clusters of apneic events.

\* \* \* \* \*